US008648182B2

(12) United States Patent
Sprecher et al.

(10) Patent No.: US 8,648,182 B2

(45) Date of Patent: Feb. 11, 2014

(54) POLYNUCLEOTIDES ENCODING ANTIBODIES TO CYTOKINE RECEPTOR ZCYTOR17

(71) Applicant: ZymoGenetics, Inc., Princeton, NJ (US)

(72) Inventors: Cindy A. Sprecher, Hereford, AR (US); Scott R. Presnell, Tacoma, WA (US); Zeren Gao, Shanghai (CN); Theodore E. Whitmore, Redmond, WA (US); Joseph L. Kuijper, Kenmore, WA (US); Mark F. Maurer, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 28 days.

(21) Appl. No.: 13/649,217

(22) Filed: Oct. 11, 2012

(65) Prior Publication Data

US 2013/0041143 A1 Feb. 14, 2013

Related U.S. Application Data

(60) Division of application No. 13/090,316, filed on Apr. 20, 2011, now Pat. No. 8,309,692, which is a division of application No. 11/511,322, filed on Oct. 20, 2006, now Pat. No. 7,947,474, which is a continuation of application No. 10/982,555, filed on Nov. 5, 2004, now abandoned, and a division of application No. 09/892,949, filed on Jun. 26, 2001, now abandoned.

(60) Provisional application No. 60/267,963, filed on Feb. 8, 2001, provisional application No. 60/214,955, filed on Jun. 29, 2000, provisional application No. 60/214,282, filed on Jun. 26, 2000.

(51) Int. Cl.

| | |
|---|---|
| ***C12N 15/12*** | (2006.01) |
| ***C07H 21/04*** | (2006.01) |
| ***C07K 16/28*** | (2006.01) |
| *C12N 15/64* | (2006.01) |
| *C12N 5/10* | (2006.01) |
| *C12P 21/02* | (2006.01) |
| *C07K 14/47* | (2006.01) |

(52) U.S. Cl.

USPC ....... 536/23.5; 435/320.1; 435/325; 435/471; 435/69.52; 435/70.1; 530/388.1; 530/388.15; 530/388.22

(58) Field of Classification Search

None

See application file for complete search history.

(56) References Cited

U.S. PATENT DOCUMENTS

| | | | |
|---|---|---|---|
| 5,116,964 | A | 5/1992 | Capon et al. |
| 7,064,186 | B2 | 6/2006 | Sprecher et al. |
| 7,494,804 | B2 | 2/2009 | Sprecher et al. |
| 7,871,618 | B2 | 1/2011 | Bilsborough |
| 2003/0096339 | A1 | 5/2003 | Sprecher et al. |
| 2003/0125520 | A1 | 7/2003 | Maeda et al. |
| 2004/0142422 | A1 | 7/2004 | Sprecher et al. |
| 2005/0214801 | A1 | 9/2005 | Sprecher et al. |
| 2007/0048303 | A1 | 3/2007 | Sprecher et al. |
| 2007/0048307 | A1 | 3/2007 | Sprecher et al. |
| 2007/0048308 | A1 | 3/2007 | Sprecher et al. |
| 2007/0048309 | A1 | 3/2007 | Sprecher et al. |
| 2007/0049527 | A1 | 3/2007 | Sprecher et al. |
| 2007/0049528 | A1 | 3/2007 | Sprecher et al. |
| 2007/0105777 | A1 | 5/2007 | Sprecher et al. |
| 2007/0141051 | A1 | 6/2007 | Sprecher et al. |
| 2011/0117052 | A1 | 5/2011 | Bilsborough |

FOREIGN PATENT DOCUMENTS

| | | |
|---|---|---|
| EP | 1188830 | 3/2002 |
| WO | WO 00/75314 | 12/2000 |
| WO | WO 02/00690 | 1/2002 |
| WO | WO 02/00721 | 1/2002 |
| WO | WO 02/08288 | 1/2002 |
| WO | WO 02/29060 | 4/2002 |
| WO | WO 02/077230 | 10/2002 |

OTHER PUBLICATIONS

Bazan, "Structurual design and molecular evolution of a cytokine receptor superfamily," *Proc. Natl. Acad. Sci. USA*, 87:6934-6938 (Sep. 1990).

Ghilardi et al., "A Novel Type I Cytokine Receptor is Expressed on Monocytes, Signals Proliferation, and Activates STAT-3 and STAT-5," *J. Biol. Chem.*, 277(19):16831-16836 (May 10, 2002).

Mahairas et al., "Sequence-tagged connectors: A sequence approach to mapping and scanning the human genome," *Proc. Natl. Acad. Sci. USA*, 96:9739-9744 (Aug. 1999).

Maeda et al., "Human haemopoietin receptor protein NR10.3 encoding cDNA SEQ ID No. 16," GenBank Acc. No. AAC92350, Mar. 2001.

Maeda et al., "Human haemopoietin receptor protein NR10.3 SEQ ID No. 17," GenBank Acc. No. AAB51244, Mar. 2001.

Zhang et al., "Homo sapiens CRL3 protein (CRL3) mRNA, complete cds," GenBank Acc. No. AF106913, 2001.

U.S. Appl. No. 13/405,916, filed Feb. 27, 2012, Sprecher et al.

Ghilardi et al., (J. Biol. Chem., vol. 277, Issue 19, 16831-16836, May 10, 2002).

Diveu et al., (J. Biol. Chem., vol. 278, Issue 50, 49850-49859, Dec. 12, 2003).

(Continued)

*Primary Examiner* — Bridget E Bunner

*Assistant Examiner* — Fozia Hamud

(74) *Attorney, Agent, or Firm* — Brian J. Walsh

(57) ABSTRACT

Novel polypeptides, polynucleotides encoding the polypeptides, and related compositions and methods are disclosed for zcytor17, a novel cytokine receptor. The polypeptides may be used within methods for detecting ligands that stimulate the proliferation and/or development of hematopoietic, lymphoid and myeloid cells in vitro and in vivo. Ligand-binding receptor polypeptides can also be used to block ligand activity in vitro and in vivo. The polynucleotides encoding zcytor17, are located on chromosome 5, and can be used to identify a region of the genome associated with human disease states. The present invention also includes methods for producing the protein, uses therefor and antibodies thereto.

5 Claims, 3 Drawing Sheets

(56) References Cited

OTHER PUBLICATIONS

Declaration of Interference between ZymoGenetics, Inc. (U.S. Appl. No. 11/551,322) and Genentech, Inc. (U.S. 7,303,896). Interference No. 105,664 (Rt). Declared Dec. 8, 2008.

Interference Decision on Priority—Favorable. Interference No. 105,664 (RT). Entered Mar. 22, 2010.

Declaration of Interference between Genentech (U.S. Appl. No. 11/548,639) and ZymoGenetics, Inc. (U.S. 7,495,080 and 7,521,537). Interference No. 105,723 (RT). Declared Oct. 21, 2009.

Interference Decision on Priority—Favorable. Interference No. 105,723 (RT). Entered Apr. 6, 2010.

```
               1                                                     50
SEQ ID NO:46   MMWTWALWML PSLCKFSLAA LPAKPENISC VYYYRKNLTC TWSPGKETSY
SEQ ID NO:18   MMWTWALWML PSLCKFSLAA LPAKPENISC VYYYRKNLTC TWSPGKETSY
SEQ ID NO:2    MMWTWALWML PSLCKFSLAA LPAKPENISC VYYYRKNLTC TWSPGKETSY
SEQ ID NO:22   MMWTWALWML PSLCKFSLAA LPAKPENISC VYYYRKNLTC TWSPGKETSY

               51                                                   100
SEQ ID NO:46   TQYTVKRTYA FGEKHDNCTT NSSTSENRAS CSFFLPRITI PDNYTIEVEA
SEQ ID NO:18   TQYTVKRTYA FGEKHDNCTT NSSTSENRAS CSFFLPRITI PDNYTIEVEA
SEQ ID NO:2    TQYTVKRTYA FGEKHDNCTT NSSTSENRAS CSFFLPRITI PDNYTIEVEA
SEQ ID NO:22   TQYTVKRTYA FGEKHDNCTT NSSTSENRAS CSFFLPRITI PDNYTIEVEA

               101                                                  150
SEQ ID NO:46   ENGDGVIKSH MTYWRLENIA KTEPPKIFRV KPVLGIKRMI QIEWIKPELA
SEQ ID NO:18   ENGDGVIKSH MTYWRLENIA KTEPPKIFRV KPVLGIKRMI QIEWIKPELA
SEQ ID NO:2    ENGDGVIKSH MTYWRLENIA KTEPPKIFRV KPVLGIKRMI QIEWIKPELA
SEQ ID NO:22   ENGDGVIKSH MTYWRLENIA KTEPPKIFRV KPVLGIKRMI QIEWIKPELA

               151                                                  200
SEQ ID NO:46   PVSSDLKYTL RFRTVNSTSW MEVNFAKNRK DKNQTYNLTG LQPFTEYVIA
SEQ ID NO:18   PVSSDLKYTL RFRTVNSTSW MEVNFAKNRK DKNQTYNLTG LQPFTEYVIA
SEQ ID NO:2    PVSSDLKYTL RFRTVNSTSW MEVNFAKNRK DKNQTYNLTG LQPFTEYVIA
SEQ ID NO:22   PVSSDLKYTL RFRTVNSTSW MEVNFAKNRK DKNQTYNLTG LQPFTEYVIA

               201                                                  250
SEQ ID NO:46   LRCAVKESKF WSDWSQEKMG MTEEEAPCGL ELWRVLKPAE ADGRRPVRLL
SEQ ID NO:18   LRCAVKESKF WSDWSQEKMG MTEEEAPCGL ELWRVLKPAE ADGRRPVRLL
SEQ ID NO:2    LRCAVKESKF WSDWSQEKMG MTEEEAPCGL ELWRVLKPAE ADGRRPVRLL
SEQ ID NO:22   LRCAVKESKF WSDWSQEKMG MTEEEGKL.L PAIPVLSALV ~~~~~~~~~~

               251                                                  300
SEQ ID NO:46   WKKARGAPVL EKTLGYNIWY YPESNTNLTE TMNTTNQQLE LHLGGESFWV
SEQ ID NO:18   WKKARGAPVL EKTLGYNIWY YPESNTNLTE TMNTTNQQLE LHLGGESFWV
SEQ ID NO:2    WKKARGAPVL EKTLGYNIWY YPESNTNLTE TMNTTNQQLE LHLGGESFWV
SEQ ID NO:22   ~~~~~~~~~~ ~~~~~~~~~~ ~~~~~~~~~~ ~~~~~~~~~~ ~~~~~~~~~~

               301                                                  350
SEQ ID NO:46   SMISYNSLGK SPVATLRIPA IQEKSFQCIE VMQACVAEDQ LVVKWQSSAL
SEQ ID NO:18   SMISYNSLGK SPVATLRIPA IQEK~~~~~~ ~~~~~~~~~~ ~~~~~~~~~~
SEQ ID NO:2    SMISYNSLGK SPVATLRIPA IQEKSFQCIE VMQACVAEDQ LVVKWQSSAL
SEQ ID NO:22   ~~~~~~~~~~ ~~~~~~~~~~ ~~~~~~~~~~ ~~~~~~~~~~ ~~~~~~~~~~
```

FIG. 1A

```
                351                                                    400
SEQ ID NO:46    DVNTWMIEWF PDVDSEPTTL SWESVSQATN WTIQQDKLKP FWCYNISVYP
SEQ ID NO:18    ~~~~~~~~~~ ~~~~~~~~~~ ~~~~~~~~~~ ~~~~~~~~~~ ~~~~~~~~~~
SEQ ID NO:2     DVNTWMIEWF PDVDSEPTTL SWESVSQATN WTIQQDKLKP FWCYNISVYP
SEQ ID NO:22    ~~~~~~~~~~ ~~~~~~~~~~ ~~~~~~~~~~ ~~~~~~~~~~ ~~~~~~~~~~

                401                                                    450
SEQ ID NO:46    MLHDKVGEPY SIQAYAKEGV PSEGPETKVE NIGVKTVTIT WKEIPKSERK
SEQ ID NO:18    ~~~~~~~~~~ ~~~~~~~~~~ ~~~~~~~~~~ ~~~~~~~~~~ ~~~~~~~~~~
SEQ ID NO:2     MLHDKVGEPY SIQAYAKEGV PSEGPETKVE NIGVKTVTIT WKEIPKSERK
SEQ ID NO:22    ~~~~~~~~~~ ~~~~~~~~~~ ~~~~~~~~~~ ~~~~~~~~~~ ~~~~~~~~~~

                451                                                    500
SEQ ID NO:46    GIICNYTIFY QAEGGKGFSK TVNSSILQYG LESLKRKTSY IVQVMASTSA
SEQ ID NO:18    ~~~~~~~~~~ ~~~~~~~~~~ ~~~~~~~~~~ ~~~~~~~~~~ ~~~~~~~~~~
SEQ ID NO:2     GIICNYTIFY QAEGGKGFSK TVNSSILQYG LESLKRKTSY IVQVMASTSA
SEQ ID NO:22    ~~~~~~~~~~ ~~~~~~~~~~ ~~~~~~~~~~ ~~~~~~~~~~ ~~~~~~~~~~

                501                                                    550
SEQ ID NO:46    GGTNGTSINF KTLSFSVFEI ILITSLIGGG LLILIILTVA YGLKKPNKLT
SEQ ID NO:18    ~~~~~~~~~~ ~~~~~~~~~~ ~~~~~~~~~~ ~~~~~~~~~~ ~~~~~~~~~~
SEQ ID NO:2     GGTNGTSINF KTLSFSVFEI ILITSLIGGG LLILIILTVA YGLKKPNKLT
SEQ ID NO:22    ~~~~~~~~~~ ~~~~~~~~~~ ~~~~~~~~~~ ~~~~~~~~~~ ~~~~~~~~~~

                551                                                    600
SEQ ID NO:46    HLCWPTVPNP AESSIATWHG DDFKDKLNLK ESDDSVNTED RILKPCSTPS
SEQ ID NO:18    ~~~~~~~~~~ ~~~~~~~~~~ ~~~~~~~~~~ ~~~~~~~~~~ ~~~~~~~~~~
SEQ ID NO:2     HLCWPTVPNP AESSIATWHG DDFKDKLNLK ESDDSVNTED RILKPCSTPS
SEQ ID NO:22    ~~~~~~~~~~ ~~~~~~~~~~ ~~~~~~~~~~ ~~~~~~~~~~ ~~~~~~~~~~

                601                                                    650
SEQ ID NO:46    DKLVIDKLVV NFGNVLQEIF TDEARTGQEN NLGGEKNGTR ILSSCPTSI~
SEQ ID NO:18    ~~~~~~~~~~ ~~~~~~~~~~ ~~~~~~~~~~ ~~~~~~~~~~ ~~~~~~~~~~
SEQ ID NO:2     DKLVIDKLVV NFGNVLQEIF TDEARTGQEN NLGGEKNGYV TCPFRPDCPL
SEQ ID NO:22    ~~~~~~~~~~ ~~~~~~~~~~ ~~~~~~~~~~ ~~~~~~~~~~ ~~~~~~~~~~

                651                                                    700
SEQ ID NO:46    ~~~~~~~~~~ ~~~~~~~~~~ ~~~~~~~~~~ ~~~~~~~~~~ ~~~~~~~~~~
SEQ ID NO:18    ~~~~~~~~~~ ~~~~~~~~~~ ~~~~~~~~~~ ~~~~~~~~~~ ~~~~~~~~~~
SEQ ID NO:2     GKSFEELPVS PEIPPRKSQY LRSRMPEGTR PEAKEQLLFS GQSLVPDHLC
SEQ ID NO:22    ~~~~~~~~~~ ~~~~~~~~~~ ~~~~~~~~~~ ~~~~~~~~~~ ~~~~~~~~~~
```

FIG. 1B

```
              701                                      733
SEQ ID NO:46  ~~~~~~~~~~ ~~~~~~~~~~ ~~~~~~~~~~ ~~~
SEQ ID NO:18  ~~~~~~~~~~ ~~~~~~~~~~ ~~~~~~~~~~ ~~~
SEQ ID NO:2   EEGAPNPYLK NSVTAREFLV SEKLPEHTKG EV~
SEQ ID NO:22  ~~~~~~~~~~ ~~~~~~~~~~ ~~~~~~~~~~ ~~~
```

FIG. 1C

POLYNUCLEOTIDES ENCODING ANTIBODIES TO CYTOKINE RECEPTOR ZCYTOR17

The present invention is a divisional of U.S. patent application Ser. No. 13/090,316, filed Apr. 20, 2011, now U.S. Pat. No. 8,309,692, which is a divisional of U.S. patent application Ser. No. 11/551,322, filed Oct. 20, 2006, now U.S. Pat. No. 7,947,474, which is a continuation of U.S. patent application Ser. No. 10/982,555, filed Nov. 5, 2004, now abandoned, which is a continuation of U.S. patent application Ser. No. 09/892,949, filed Jun. 26, 2001, now abandoned, which claims the benefit of U.S. Patent Application Ser. Nos. 60/267,963, filed Feb. 8, 2001, 60/214,955, filed Jun. 29, 2000, and 60/214,282, filed Jun, 26, 2000, all of which are herein incorporated by reference.

BACKGROUND OF THE INVENTION

Hormones and polypeptide growth factors control proliferation and differentiation of cells of multicellular organisms. These diffusable molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors. Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The demonstrated in vivo activities of these cytokines illustrate the enormous clinical potential of, and need for, other cytokines, cytokine agonists, and cytokine antagonists. The present invention addresses these needs by providing new a hematopoietic cytokine receptor, as well as related compositions and methods.

The present invention provides such polypeptides for these and other uses that should be apparent to those skilled in the art from the teachings herein. These and other aspects of the invention will become evident upon reference to the following detailed description of the invention.

BRIEF DESCRIPTION OF THE DRAWINGS

FIG. 1 is depicted in 3 panels (FIG. 1A, FIG. 1B and FIG. 1C) and shows a multiple alignment of zcytor17 polypeptide sequences SEQ ID NO:46, SEQ ID NO:18, SEQ ID NO:2, and SEQ ID NO:22.

DESCRIPTION OF THE INVENTION

Within one aspect, the present invention provides an isolated polynucleotide that encodes a polypeptide comprising a sequence of amino acid residues that is at least 90% identical to an amino acid sequence selected from the group consisting of (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); (c) the amino acid sequence as shown in SEQ ID NO:2 from amino acid number 20 (Ala) to amino acid number 543 (Leu); (d) the amino acid sequence as shown in SEQ ID NO:2 from amino acid number 544 (Lys) to amino acid number 732 (Val); (e) the amino acid sequence as shown in SEQ ID NO:46 from amino acid number 544 (Lys) to amino acid number 649 (Ile); (f) the amino acid sequence as shown in SEQ ID NO:2 from amino acid number 20 (Ala) to amino acid number 732 (Val); (g) the amino acid sequence as shown in SEQ ID NO:46 from amino acid number 20 (Ala) to amino acid number 649 (Ile); (h) the amino acid sequence as shown in SEQ ID NO:2 from amino acid number 1 (Met) to amino acid number 732 (Val); and (i) the amino acid sequence as shown in SEQ ID NO:46 from amino acid number 1 (Met) to amino acid number 649 (Ile). In one embodiment, the isolated polynucleotide disclosed above comprises a sequence of amino acid residues that is selected from the group consisting of: (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); (c) the amino acid sequence as shown in SEQ ID NO:2 from amino acid number 20 (Ala) to amino acid number 543 (Leu); (d) the amino acid sequence as shown in SEQ ID NO:2 from amino acid number 544 (Lys) to amino acid number 732 (Val); (e) the amino acid sequence as shown in SEQ ID NO:46 from amino acid number 544 (Lys) to amino acid number 649 (Ile); (f) the amino acid sequence as shown in SEQ ID NO:2 from amino acid number 20 (Ala) to amino acid number 732 (Val); (g) the amino acid sequence as shown in SEQ ID NO:46 from amino acid number 20 (Ala) to amino acid number 649 (Ile); (h) the amino acid sequence as shown in SEQ ID NO:2 from amino acid number 1 (Met) to amino acid number 732 (Val); and (i) the amino acid sequence as shown in SEQ ID NO:46 from amino acid number 1 (Met) to amino acid number 649 (Ile). In another embodiment, the isolated polynucleotide disclosed above comprises a sequence selected from the group consisting of: (a) a polynucleotide as shown in SEQ ID NO:1 from nucleotide number 228 to amino acid number 851; (b) a polynucleotide as shown in SEQ ID NO:1 from nucleotide number 228 to amino acid number 1727; (c) a polynucleotide as shown in SEQ ID NO:1 from nucleotide number 228 to amino acid number 1799; (d) a polynucleotide as shown in SEQ ID NO:1 from nucleotide number 1800 to amino acid number 2366; (e) a polynucleotide as shown in SEQ ID NO:45 from nucleotide number 1791 to amino acid number 2108; (f) a polynucleotide as shown in SEQ ID NO:1 from nucleotide number 228 to amino acid number 2366; (g) a polynucleotide as shown in SEQ ID NO:45 from nucleotide number 219 to amino acid number 2108; (h) a polynucleotide as shown in SEQ ID NO:1 from nucleotide number 171 to amino acid number 2366; (i) a polynucleotide as shown in SEQ ID NO:45 from nucleotide number 162 to amino acid number 2108; and (j) a polynucleotide sequence complementary to (a) through (i). In another embodiment, the isolated polynucleotide disclosed above encodes a polypeptide that further comprises a transmembrane domain consisting of residues 520 (Ile) to 543 (Leu) of SEQ ID NO:2. In another embodiment, the isolated polynucleotide disclosed above encodes a polypeptide that further comprises an intracellular domain consisting of residues 544 (Lys) to 732 (Val) of SEQ ID NO:2 or 544 (Lys) to 649 (Ile) of SEQ ID NO:46. In another embodiment, the isolated polynucleotide disclosed above encodes a polypeptide that has activity as measured by cell proliferation, activation of transcription of a reporter gene, or wherein the polypeptide encoded by the polynucleotide further binds to an antibody, wherein the antibody is raised to a polypeptide comprising a sequence of amino acids from the group consisting of: (a) the polypeptide comprising amino acid number 20 (Ala) to 227 (Pro) of SEQ ID NO:2; (b) the polypeptide comprising amino acid number 20 (Ala) to 519 (Glu) of SEQ ID NO:2; (c) the polypeptide comprising amino acid number 20 (Ala) to 543 (Leu) of SEQ ID NO:2; (d) the polypeptide comprising amino acid number 544 (Lys) to 732 (Val) of SEQ ID NO:2; (e) the polypeptide comprising amino acid number 544 (Lys) to 649 (Ile) of SEQ ID NO:46; (f) the polypeptide comprising amino acid number 20 (Ala) to 732 (Val) of SEQ ID NO:2; (g) the polypeptide comprising amino acid number 20 (Ala) to 649 (Ile) of SEQ ID NO:46; (h) the polypeptide comprising amino acid number 1 (Met) to 732 (Val) of SEQ ID NO:2; and (i) the polypeptide comprising amino acid number 1 (Met) to 649 (Ile) of SEQ ID NO:46, and wherein the binding of the antibody to the isolated polypeptide is measured by a biological or biochemical assay including radioimmunoassay, radioimmuno-precipitation, Western blot, or enzyme-linked immunosorbent assay.

Within a second aspect, the present invention provides an expression vector comprising the following operably linked elements: a transcription promoter; a DNA segment encoding a polypeptide that is at least 90% identical to an amino acid sequence as shown in SEQ ID NO:2 from amino acid number 20 (Ala) to 732 (Val); or is at least 90% identical to an amino acid sequence as shown in SEQ ID NO:46 from amino acid number 20 (Ala) to 649 (Ile); and a transcription terminator, wherein the promoter is operably linked to the DNA segment, and the DNA segment is operably linked to the transcription terminator. In one embodiment, the expression vector disclosed above further comprises a secretory signal sequence operably linked to the DNA segment.

Within a third aspect, the present invention provides a cultured cell comprising an expression vector as disclosed above, wherein the cell expresses a polypeptide encoded by the DNA segment. In another embodiment, the expression vector disclosed above comprises a DNA segment that encodes a polypeptide comprising an amino acid sequence as shown in SEQ ID NO:2 from amino acid number 20 (Ala) to 227 (Pro); or as shown in SEQ ID NO:2 from amino acid number 20 (Ala) to 519 (Glu); and a transcription terminator, wherein the promoter, DNA segment, and terminator are operably linked. In another embodiment, the expression vector disclosed above further comprises a secretory signal sequence operably linked to the DNA segment. In another embodiment, the expression vector disclosed above further comprises a transmembrane domain consisting of residues 520 (Ile) to 543 (Leu) of SEQ ID NO:2. In another embodiment, the expression vector disclosed above further comprises an intracellular domain consisting of residues 544 (Lys) to 732 (Val) of SEQ ID NO:2, or residues 544 (Lys) to 649 (Ile) of SEQ ID NO:46.

Within another aspect, the present invention provides a cultured cell into which has been introduced an expression vector as disclosed above, wherein the cell expresses a soluble receptor polypeptide encoded by the DNA segment.

Within another aspect, the present invention provides a DNA construct encoding a fusion protein, the DNA construct comprising: a first DNA segment encoding a polypeptide comprising a sequence of amino acid residues selected from the group consisting of: (a) the amino acid sequence of SEQ ID NO:2 from amino acid number 1 (Met), to amino acid number 19 (Ala); (b) the amino acid sequence of SEQ ID NO:54 from amino acid number 1 (Met), to amino acid number 32 (Ala); (c) the amino acid sequence of SEQ ID NO:2 from amino acid number 20 (Ala), to amino acid number 227 (Pro); (d) the amino acid sequence of SEQ ID NO:2 from amino acid number 20 (Ala), to amino acid number 519 (Glu); (e) the amino acid sequence as shown in SEQ ID NO:2 from amino acid number 20 (Ala) to amino acid number 543 (Leu); (f) the amino acid sequence as shown in SEQ ID NO:2 from amino acid number 520 (Ile) to amino acid number 543 (Leu); (g) the amino acid sequence as shown in SEQ ID NO:2 from amino acid number 544 (Lys) to amino acid number 732 (Val); (h) the amino acid sequence as shown in SEQ ID NO:46 from amino acid number 544 (Lys) to amino acid number 649 (Ile); (i) the amino acid sequence as shown in SEQ ID NO:2 from amino acid number 20 (Ala) to amino acid number 732 (Val); and (j) the amino acid sequence as shown in SEQ ID NO:46 from amino acid number 20 (Ala) to amino acid number 649 (Ile); and at least one other DNA segment encoding an additional polypeptide, wherein the first and other DNA segments are connected in-frame; and wherein the first and other DNA segments encode the fusion protein.

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell as disclosed above; and isolating the polypeptide produced by the cell.

Within another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); (c) the amino acid sequence as shown in SEQ ID NO:2 from amino acid number 20 (Ala) to amino acid number 543 (Leu); (d) the amino acid sequence as shown in SEQ ID NO:2 from amino acid number 544 (Lys) to amino acid number 732 (Val); (e) the amino acid sequence as shown in SEQ ID NO:46 from amino acid number 544 (Lys) to amino acid number 649 (Ile); (f) the amino acid sequence as shown in SEQ ID NO:2 from amino acid number 20 (Ala) to amino acid number 732 (Val); (g) the amino acid sequence as shown in SEQ ID NO:46 from amino acid number 20 (Ala) to amino acid number 649 (Ile); (h) the amino acid sequence as shown in SEQ ID NO:2 from amino acid number 1 (Met) to amino acid number 732 (Val); and (i) the amino acid sequence as shown in SEQ ID NO:46 from amino acid number 1 (Met) to amino acid number 649 (Ile). In one embodiment, the isolated polypeptide disclosed above comprises a sequence of amino acid residues that is selected from the group consisting of: (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); (c) the amino acid sequence as shown in SEQ ID NO:2 from amino acid number 20 (Ala) to amino acid number 543 (Leu); (d) the amino acid sequence as shown in SEQ ID NO:2 from amino acid number 544 (Lys) to amino acid number 732 (Val); (e) the amino acid sequence as shown in SEQ ID NO:46 from amino acid number 544 (Lys) to amino acid number 649 (Ile); (f) the amino acid sequence as shown in SEQ ID NO:2 from amino acid number 20 (Ala) to amino acid number 732 (Val); (g) the amino acid sequence as shown in SEQ ID NO:46 from amino acid number 20 (Ala) to amino acid number 649 (Ile); (h) the amino acid sequence as shown in SEQ ID NO:2 from amino acid number 1 (Met) to amino acid number 732 (Val); and (i) the amino acid sequence as shown in SEQ ID NO:46 from amino acid number 1 (Met) to amino acid number 649 (Ile). In another embodiment, the isolated polypeptide disclosed above further comprises a transmembrane domain consisting of residues 520 (Ile) to 543 (Leu) of SEQ ID NO:2. In another embodiment, the isolated polypeptide disclosed above further comprises an intracellular domain consisting of residues 544 (Lys) to 732 (Val) of SEQ ID NO:2 or 544 (Lys) to 649 (Ile) of SEQ ID NO:46. In another embodiment, the isolated polypeptide disclosed above has activity as measured by cell proliferation, activation of transcription of a reporter gene, or wherein the polypeptide encoded by the polynucleotide further binds to an antibody, wherein the antibody is raised to a polypeptide comprising a sequence of amino acids from the group consisting of: (a) the polypeptide comprising amino acid number 20 (Ala) to 227 (Pro) of SEQ ID NO:2; (b) the polypeptide comprising amino acid number 20 (Ala) to 519 (Glu) of SEQ ID NO:2; (c) the polypeptide comprising amino acid number 20 (Ala) to 543 (Leu) of SEQ ID NO:2; (d) the polypeptide comprising amino acid number 544 (Lys) to 732 (Val) of SEQ ID NO:2; (e) the polypeptide comprising amino acid number 544 (Lys) to 649 (Ile) of SEQ ID NO:46; (f) the polypeptide comprising amino acid number 20 (Ala) to 732 (Val) of SEQ ID NO:2; (g) the polypeptide comprising amino acid number 20 (Ala) to 649 (Ile) of SEQ ID NO:46; (h) the polypeptide comprising amino acid number 1 (Met) to 732 (Val) of SEQ ID NO:2; and (i) the polypeptide comprising amino acid number 1 (Met) to 649 (Ile) of SEQ ID NO:46, and wherein the binding of the antibody to the isolated polypeptide is measured by a biological or biochemical assay including radioimmunoassay, radioimmuno-precipitation, Western blot, or enzyme-linked immunosorbent assay.

Within another aspect, the present invention provides a method of producing a zcytor17 polypeptide comprising: culturing a cell as disclosed above; and isolating the zcytor17 polypeptide produced by the cell.

Within another aspect, the present invention provides an isolated polypeptide comprising an amino acid segment selected from the group consisting of: (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); the amino acid sequence as shown in SEQ ID NO:18; the amino acid sequence as shown in SEQ ID NO:22; and (b) sequences that are at least 90% identical to (a) or (b), wherein the polypeptide is substantially free of transmembrane and intracellular domains ordinarily associated with hematopoietic receptors. Within another aspect, the present invention provides a method of producing a zcytor17 polypeptide comprising: culturing a cell as disclosed above; and isolating the zcytor17 polypeptide produced by the cell. Within another aspect, the present invention provides a method of producing an antibody to a zcytor17 polypeptide comprising: inoculating an animal with a polypeptide selected from the group consisting of: (a) a polypeptide consisting of 9 to 713 amino acids, wherein the polypeptide comprises a contiguous sequence of amino acids in SEQ ID NO:2 from amino acid number 20 (Ala), to amino acid number 732 (Val); (b) a polypeptide consisting of 9 to 630 amino acids, wherein the polypeptide comprises a contiguous sequence of amino acids in SEQ ID NO:46 from amino acid number 20 (Ala), to amino acid number 649 (Ile); (c) a polypeptide comprising amino acid number 20 (Ala) to 227 (Pro) of SEQ ID NO:2; (d) a polypeptide comprising amino acid number 20 (Ala) to 519 (Glu) of SEQ ID NO:2; (e) a polypeptide comprising amino acid number 20 (Ala) to 543 (Leu) of SEQ ID NO:2; (f) a polypeptide comprising amino acid number 544 (Lys) to 732 (Val) of SEQ ID NO:2; (g) a polypeptide comprising amino acid number 544 (Lys) to 649 (Ile) of SEQ ID NO:46; (h) a polypeptide comprising amino acid number 20 (Ala) to 732 (Val) of SEQ ID NO:2; (i) a polypeptide comprising amino acid number 20 (Ala) to 649 (Ile) of SEQ ID NO:46; (j) a polypeptide comprising amino acid number 1 (Met) to 732 (Val) of SEQ ID NO:2; (k) a polypeptide comprising amino acid number 1 (Met) to 649 (Ile) of SEQ ID NO:46, (l) a polypeptide comprising amino acid residues 43 through 48 of SEQ ID NO:2; (m) a polypeptide comprising amino acid residues 157 through 162 of SEQ ID NO:2; (n) a polypeptide comprising amino acid residues 158 through 163 of SEQ ID NO:2; (o) a polypeptide comprising amino acid residues 221 through 226 of SEQ ID NO:2; and (p) a polypeptide comprising amino acid residues 426 through 431 of SEQ ID NO:2; and wherein the polypeptide elicits an immune response in the animal to produce the antibody; and isolating the antibody from the animal. Within another aspect, the present invention provides an antibody produced by the method as disclosed above, which specifically binds to a zcytor17 polypeptide. In one embodiment, the antibody disclosed above is a monoclonal antibody.

Within another aspect, the present invention provides an antibody that specifically binds to a polypeptide as disclosed above. In one embodiment, the antibody disclosed above binds to a polypeptide of as disclosed above.

Within another aspect, the present invention provides a method of detecting, in a test sample, the presence of a modulator of zcytor17 protein activity, comprising: culturing a cell into which has been introduced an expression vector as disclosed above, wherein the cell expresses the zcytor17 protein encoded by the DNA segment in the presence and absence of a test sample; and comparing levels of activity of zcytor17 in the presence and absence of a test sample, by a biological or biochemical assay; and determining from the comparison, the presence of modulator of zcytor17 activity in the test sample.

Within another aspect, the present invention provides a method for detecting a zcytor17 receptor ligand within a test sample, comprising: contacting a test sample with a polypeptide comprising an amino acid sequence from the group consisting of (a) the amino acid sequence as shown in SEQ ID NO:2 from amino acid number 20 (Ala) to amino acid number 227 (Pro); (b) the amino acid sequence as shown in SEQ ID NO:2 from amino acid number 20 (Ala) to amino acid number 519 (Glu); the amino acid sequence as shown in SEQ ID NO:18; the amino acid sequence as shown in SEQ ID NO:22; and detecting the binding of the polypeptide to a ligand in the sample. In one embodiment is provided the method disclosed above wherein the polypeptide is membrane bound within a cultured cell, and the detecting step comprises measuring a biological response in the cultured cell. In another embodiment is provided the method disclosed above wherein the biological response is cell proliferation or activation of transcription of a reporter gene.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers, multimers, or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. Cell-surface cytokine receptors are characterized by a multi-domain structure as discussed in more detail below. These receptors are anchored in the cell membrane by a transmembrane domain characterized by a sequence of hydrophobic amino acid residues (typically about 21-25 residues), which is commonly flanked by positively charged residues (Lys or Arg). In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a protein having the structure of a class I cytokine receptor. The deduced amino acid sequence indicated that the encoded receptor belongs to the receptor subfamily that includes gp130, LIF, IL-12, oncostatin M receptor (OSM-R), WSX-1 receptors (Sprecher C A et al., *Biochem. Biophys. Res. Comm*. 246:81-90 (1998), DCRS2 (WIPO Publication No. WO00/73451), the IL-2 receptor β-subunit and the β-common receptor (i.e., IL3, IL-5, and GM-CSF receptor β-subunits. The polypeptide has been designated zcytor17. The zcytor17 polynucleotide sequence encodes the entire coding sequence of the predicted protein. Zcytor17 is a novel cytokine receptor that may be involved in immune regulation, an apoptotic cellular pathway, as a cell-cell signaling molecule, growth factor receptor, or extracellular matrix associated protein with growth factor hormone activity, or the like.

The sequence of the zcytor17 polypeptide was deduced from genomic DNA as well as identified clones that contained its corresponding polynucleotide sequence. The clones were obtained from a prostate library. Other libraries that might also be searched for such sequences include PBL, testes, monocytes, thymus, spleen, lymph node, bone marrow, human erythroleukemia, lung (e.g., WI-38 cells) and acute monocytic leukemia cell lines, other lymphoid and hematopoietic cell lines, and the like.

Nucleotide sequences of representative zcytor17-encoding DNA are described in SEQ ID NO:1 (from nucleotide 171 to 2366), with its deduced 732 amino acid sequence described in SEQ ID NO:2; SEQ ID NO:45 (from nucleotide 162 to 2108), with its deduced 649 amino acid sequence described in SEQ ID NO:46.; and in SEQ ID NO:53 (from nucleotide 497 to 2482), with its deduced 662 amino acid sequence described in SEQ ID NO:54. In its entirety, the zcytor17 polypeptide (SEQ ID NO:2, SEQ ID NO:46 or SEQ ID NO:54) represents a full-length polypeptide segment (residue 1 (Met) to residue 732 (Val) of SEQ ID NO:2; residue 1 (Met) to residue 649 (Ile) of SEQ ID NO:46; residue 1 (Met) to residue 662 (Ile) of SEQ ID NO:54). The domains and structural features of the zcytor17 polypeptides are further described below.

Analysis of the zcytor17 polypeptide encoded by the DNA sequence of SEQ ID NO:1 revealed an open reading frame encoding 732 amino acids (SEQ ID NO:2) comprising a predicted secretory signal peptide of 19 amino acid residues (residue 1 (Met) to residue 19 (Ala) of SEQ ID NO:2), and a mature polypeptide of 713 amino acids (residue 20 (Ala) to residue 732 (Val) of SEQ ID NO:2). Analysis of the zcytor17 polypeptide encoded by the DNA sequence of SEQ ID NO:45 revealed an open reading frame encoding 649 amino acids (SEQ ID NO:46) comprising a predicted secretory signal peptide of 19 amino acid residues (residue 1 (Met) to residue 19 (Ala) of SEQ ID NO:46), and a mature polypeptide of 630 amino acids (residue 20 (Ala) to residue 649 (Ile) of SEQ ID NO:46). Analysis of the zcytor17 polypeptide encoded by the DNA sequence of SEQ ID NO:53 revealed an open reading frame encoding 662 amino acids (SEQ ID NO:54) comprising a predicted secretory signal peptide of 32 amino acid residues (residue 1 (Met) to residue 32 (Ala) of SEQ ID NO:54), and a mature polypeptide of 630 amino acids (residue 33 (Ala) to residue 662 (Ile) of SEQ ID NO:54). In addition to the WSXWS motif (SEQ ID NO:3) (corresponding to residues 211 to 215 of SEQ ID NO:2 and SEQ ID NO:46; and residues 224 to 228 of SEQ ID NO:54), the receptor comprises an extracellular domain (residues 20 (Ala) to 519 (Glu) of SEQ ID NO:2 and SEQ ID NO:46; residues 33 (Ala) to 532 (Glu) of SEQ ID NO:54) which includes a cytokine-binding domain of approximately 200 amino acid residues (residues 20 (Ala) to 227 (Pro) of SEQ ID NO:2 and SEQ ID NO:46; residues 33 (Ala) to 240 (Pro) of SEQ ID NO:54); a domain linker (residues 122 (Thr) to 125 (Pro) of SEQ ID NO:2 and SEQ ID NO:46; residues 135 (Thr) to 138 (Pro) of SEQ ID NO:2); a penultimate strand region (residues 194 (Phe) to 202 (Arg) of SEQ ID NO:2 and SEQ ID NO:46; residues 207 (Phe) to 215 (Arg) of SEQ ID NO:54); a fibronectin type III domain (residues 228 (Cys) to 519 (Glu) of SEQ ID NO:2 and SEQ ID NO:46; residues 241 (Cys) to 532 (Glu) of SEQ ID NO:54); a transmembrane domain (residues 520 (Ile) to 543 (Leu) of SEQ ID NO:2 and SEQ ID NO:46; residues 533 (Ile) to 556 (Leu) of SEQ ID NO:54); complete intracellular signaling domain (residues 544 (Lys) to 732 (Val) of SEQ ID NO:2; residues 544 (Lys) to 649 (Ile) of SEQ ID NO:46; and residues 557 (Lys) to 662 (Ile) of SEQ ID NO:54) which contains a "Box I" signaling site (residues 554 (Trp) to 560 (Pro) of SEQ ID NO:2 and SEQ ID NO:46; residues 567 (Trp) to 573 (Pro) of SEQ ID NO:54), and a "Box II" signaling site (residues 617 (Gln) to 620 (Phe) of SEQ ID NO:2 and SEQ ID NO:46; residues 630 (Gln) to 633 (Phe) of SEQ ID NO:54). Those skilled in the art will recognize that these domain boundaries are approximate, and are based on alignments with known proteins and predictions of protein folding. In addition to these domains, conserved receptor features in the encoded receptor include (as shown in SEQ ID NO:2 and SEQ ID NO:46) a conserved Cys residue at position 30 (position 43 as shown in SEQ ID NO:54), CXW motif (wherein X is any amino acid) at positions 40-42 (positions 53-55 as shown in SEQ ID NO:54), Trp residue at position 170 (position 183 as shown in SEQ ID NO:54), and a conserved Arg residue at position 202 (position 215 as shown in SEQ ID NO:54). The corresponding polynucleotides encoding the zcytor17 polypeptide regions, domains, motifs, residues and sequences described above are as shown in SEQ ID NO:1, SEQ ID NO:45, and SEQ ID NO:53.

Moreover, truncated forms of the zcytor17 polypeptide appear to be naturally expressed. Both forms encode soluble zcytor17 receptors. A polynucleotide encoding a "long-form" of the soluble zcytor17 receptor, truncated within the fibronectin type III domain, is shown in SEQ ID NO:17 and the corresponding polypeptide is shown in SEQ ID NO:18. This truncated form encodes residues 1 (Met) through 324 (Lys) of SEQ ID NO:2 and SEQ ID NO:46), and thus comprises an intact signal sequence, WSXWS (SEQ ID NO:3) motif, linker, cytokine binding domain, penultimate strand, and conserved, Cys, CXW motif, Trp and Arg residues as described above. A polynucleotide encoding a "short-form" of the soluble zcytor17 receptor, truncated at the end of the cytokine binding domain is shown in SEQ ID NO:21 and the corresponding polypeptide is shown in SEQ ID NO:22. This truncated form encodes a 239 residue polypeptide that is identical to residues 1 (Met) through 225 (Glu) of SEQ ID NO:2 and SEQ ID NO:46 and then diverges, and thus comprises an intact signal sequence, WSXWS (SEQ ID NO:3) motif, linker, cytokine binding domain, penultimate strand, and conserved, Cys, CXW motif, Trp and Arg residues as described above. A multiple alignment of the truncated forms compared to the full-length forms of zcytor17 is shown in FIG. 1.

Moreover, the zcytor17 cDNA of SEQ ID NO:1, SEQ ID NO:45, SEQ ID NO:17, and SEQ ID NO:21 encode polypeptides that may use an alternative initiating methionine (at nucleotide 75 of SEQ ID NO:1, at nucleotide 66 of SEQ ID NO:45, at nucleotide 66 of SEQ ID NO:17, and at nucleotide 66 of SEQ ID NO:21) that would encode a polypeptide in the same open reading frame (ORF) as the zcytor17 polypeptides of SEQ ID NO:2, SEQ ID NO:46, SEQ ID NO:18, and SEQ ID NO:22. Use of the alternative initiating methionine would add 32 amino acids (shown in SEQ ID NO:48) in-frame to the N-terminus of SEQ ID NO:2, SEQ ID NO:46, SEQ ID NO: 8, and SEQ ID NO:2. In addition, nucleotide 536 of SEQ ID NO:53 may serve as an alternative initiating methionine, thus generating the same N-terminus (starting at amino acid 14 (Met) of SEQ ID NO:54) and signal polypeptide sequence, as SEQ ID NO:2, SEQ ID NO:46, SEQ ID NO:18, and SEQ ID NO:22. Moreover, the second Met at amino acid number 2 in the SEQ ID NO:2, SEQ ID NO:46, SEQ ID NO:18, and SEQ ID NO:22 sequences (similarly at amino acid number 15 (Met) in SEQ ID NO:54) may also serve as an alternative starting methionine for the polypeptides.

The presence of transmembrane regions, and conserved and low variance motifs generally correlates with or defines important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, cell-cell interaction, tissue localization domains and the like.

The regions of conserved amino acid residues in zcytor17, described above, can be used as tools to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zcytor17 sequences are useful for this purpose. Designing and using such degenerate primers may be readily performed by one of skill in the art.

The present invention provides polynucleotide molecules, including DNA and RNA molecules that encode the zcytor17 polypeptides disclosed herein. Those skilled in the art will recognize that, in view of the degeneracy of the genetic code, considerable sequence variation is possible among these polynucleotide molecules. SEQ ID NO:4, SEQ ID NO:47 and SEQ ID NO:55 are degenerate DNA sequences that encompass all DNAs that encode the zcytor17 polypeptide of SEQ ID NO:2, SEQ ID NO:46 and SEQ ID NO:54 respectively. Those skilled in the art will recognize that the degenerate sequences of SEQ ID NO:4, SEQ ID NO:47 and SEQ ID NO:55 also provide all RNA sequences encoding SEQ ID NO:2, SEQ ID NO:46 and SEQ ID NO:54 by substituting U for T. Thus, zcytor17 polypeptide-encoding polynucleotides comprising nucleotide 1 to nucleotide 2196 of SEQ ID NO:4, nucleotide 1 to nucleotide 1947 of SEQ ID NO:47, and nucleotide 1 to nucleotide 1986 of SEQ ID NO:55 and their RNA equivalents are contemplated by the present invention. Table 1 sets forth the one-letter codes used within SEQ ID NO:4, SEQ ID NO:47 and SEQ ID NO:55 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, SEQ ID NO:47 and SEQ ID NO:55, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | • | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:2, SEQ ID NO:46 and SEQ ID NO:54; or SEQ ID NO:57 and SEQ ID NO:93. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NO:4, SEQ ID NO:47 and SEQ ID NO:55 serve as templates for optimizing expression of zcytor17 polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, SEQ ID NO:45, or SEQ ID NO:54; or SEQ ID NO:57 and SEQ ID NO:93; or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol*. 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20-25° C. below the calculated $T_m$. For smaller probes (e.g., <50 base pairs) hybridization is typically carried out at the $T_m$ or 5-10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40-50% formamide, up to about 6×SSC, about 5× Denhardt's solution, zero up to about 10% dextran sulfate, and about 10-20 μg/ml denatured commercially-available carrier DNA. Generally, such stringent conditions include temperatures of 20-70° C. and a hybridization buffer containing up to 6×SSC and 0-50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zcytor17 RNA. Such tissues and cells are identified by Northern blotting (Thomas, *Proc. Natl. Acad. Sci. USA* 77:5201, 1980), and include PBLs, spleen, thymus, bone marrow, prostate, and lymph tissues, human erythroleukemia cell lines, acute monocytic leukemia cell lines, other lymphoid and hematopoietic cell lines, and the like. Total RNA can be prepared using guanidinium isothiocyanate extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-12, 1972). Complementary DNA (cDNA) is prepared from poly$(A)^+$ RNA using known methods. In the alternative, genomic DNA can be isolated. Polynucleotides encoding zcytor17 polypeptides are then identified and isolated by, for example, hybridization or polymerase chain reaction (PCR) (Mullis, U.S. Pat. No. 4,683,202).

A full-length clone encoding zcytor17 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zcytor17, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

An alternative way to prepare a full-length gene is to synthesize a specified set of overlapping oligonucleotides (40 to 100 nucleotides). After the 3' and 5' short overlapping complementary regions (6 to 10 nucleotides) are annealed, large gaps still remain, but the short base-paired regions are both long enough and stable enough to hold the structure together. The gaps are filled and the DNA duplex is completed via enzymatic DNA synthesis by *E. coli* DNA polymerase I.

After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem*. 53: 323-56, 1984 and Climie et al., *Proc. Natl. Acad. Sci. USA* 87:633-7, 1990. Moreover, other sequences are generally added that contain signals for proper initiation and termination of transcription and translation.

The present invention further provides counterpart polypeptides and polynucleotides from other species (orthologs). These species include, but are not limited to mammalian, avian, amphibian, reptile, fish, insect and other vertebrate and invertebrate species. Of particular interest are zcytor17 polypeptides from other mammalian species, including murine, porcine, ovine, bovine, canine, feline, equine, and other primate polypeptides. Orthologs of human zcytor17 can be cloned using information and compositions provided by the present invention in combination with conventional cloning techniques. For example, a cDNA can be cloned using mRNA obtained from a tissue or cell type that expresses zcytor17 as disclosed herein. Suitable sources of mRNA can be identified by probing Northern blots with probes designed from the sequences disclosed herein. A library is then prepared from mRNA of a positive tissue or cell line. A zcytor17-encoding cDNA can then be isolated by a variety of methods, such as by probing with a complete or partial human cDNA or with one or more sets of degenerate probes based on the disclosed sequences. A cDNA can also be cloned using PCR (Mullis, supra.), using primers designed from the representative human zcytor17 sequence disclosed herein. Within an additional method, the cDNA library can be used to transform or transfect host cells, and expression of the cDNA of interest can be detected with an antibody to zcytor17 polypeptide. Similar techniques can also be applied to the isolation of genomic clones.

A polynucleotide sequence for the mouse ortholog of human zcytor17 has been identified and is shown in SEQ ID NO:56 and the corresponding amino acid sequence shown in SEQ ID NO:57. Analysis of the mouse zcytor17 polypeptide encoded by the DNA sequence of SEQ ID NO:56 revealed an open reading frame encoding 662 amino acids (SEQ ID NO:57) comprising a predicted secretory signal peptide of 45 amino acid residues (residue 1 (Met) to residue 45 (Ala) of SEQ ID NO:57), and a mature polypeptide of 617 amino acids (residue 46 (Val) to residue 662 (Cys) of SEQ ID NO:57). Moreover, an additional Met residue, Met (28) can be used as a starting methionine; comprising a second predicted secretory signal peptide of 18 amino acid residues (residue 28 (Met) to residue 45 (Ala) of SEQ ID NO:57), and the same mature polypeptide of 617 amino acids (residue 46 (Val) to residue 662 (Cys) of SEQ ID NO:57. In addition to the WSXWS motif (SEQ ID NO:3) corresponding to residues 224-228 of SEQ ID NO:57, the receptor comprises an extracellular domain from residues 46 (Val) to 533 (Glu) of SEQ ID NO:57) that includes a cytokine-binding domain of approximately 200 amino acid residues (residues 46 (Val) to 240 (Pro) of SEQ ID NO:57) and a fibronectin III domain (residues 241 (H is) to 533 (Glu) of SEQ ID NO:57); a CXW motif (residues 66 (Cys) to 68 (Trp) of SEQ ID NO:57); a domain linker (residues 142 (Thr) to 145 (Pro) of SEQ ID NO:57); a penultimate strand region (residues 207 (Phe) to 215 (Arg) of SEQ ID NO:57); a transmembrane domain (residues 534 (Ile) to 550 (Ile) of SEQ ID NO:57); complete intracellular signaling domain (residues 551 (Lys) to 662 (Cys) of SEQ ID NO:57) which contains a "Box I" signaling site (residues 568 (Cys) to 574 (Pro) of SEQ ID NO:57), and a "Box II" signaling site (residues 628 (Glu) to 631 (leu) of SEQ ID NO:57). Conserved residues common to class I cytokine receptors, are at residues 56 (Cys), 187 (Trp), and 215 (Arg). A comparison of the human and mouse amino acid sequences reveals that both the human and orthologous polypeptides contain corresponding structural features described above (and, see, FIG. 2). The mature sequence for the mouse zcytor17 begins at $Val_{46}$ (as shown in SEQ ID NO:57), which corresponds to $Ala_{33}$ (as shown in SEQ ID NO:54) in the human sequence. There is about 61% identity between the mouse and human sequences over the entire amino acid sequence corresponding to SEQ ID NO:54 and SEQ ID NO:57. The above percent identity was determined using a FASTA program with ktup=1, gap opening penalty=12, gap extension penalty=2, and substitution matrix=BLOSUM62, with other parameters set as default. The corresponding polynucleotides encoding the mouse zcytor17 polypeptide regions, domains, motifs, residues and sequences described above are as shown in SEQ ID NO:56.

Moreover, a truncated soluble form of the mouse zcytor17 receptor polypeptide appears to be naturally expressed. A polynucleotide sequence for a truncated soluble form of the mouse zcytor17 receptor has been identified and is shown in SEQ ID NO:92 and the corresponding amino acid sequence shown in SEQ ID NO:93. Analysis of the truncated soluble mouse zcytor17 polypeptide encoded by the DNA sequence of SEQ ID NO:92 revealed an open reading frame encoding 547 amino acids (SEQ ID NO:93) comprising a predicted secretory signal peptide of 45 amino acid residues (residue 1 (Met) to residue 45 (Ala) of SEQ ID NO:93), and a mature polypeptide of 502 amino acids (residue 46 (Val) to residue 547 (Val) of SEQ ID NO:93). Moreover, an additional Met residue, Met (28) can be used as a starting methionine; comprising a second predicted secretory signal peptide of 18 amino acid residues (residue 28 (Met) to residue 45 (Ala) of SEQ ID NO:93), and the same mature polypeptide of 502 amino acids (residue 46 (Val) to residue 547 (Val) of SEQ ID NO:93. In addition to the WSXWS motif (SEQ ID NO:3) corresponding to residues 224-228 of SEQ ID NO:93, the receptor comprises an extracellular domain from residues 46 (Val) to 533 (Trp) of SEQ ID NO:93) that includes a cytokine-binding domain of approximately 200 amino acid residues (residues 46 (Val) to 240 (Pro) of SEQ ID NO:93) and a fibronectin III domain (residues 241 (His) to 533 (Trp) of SEQ ID NO:93); a CXW motif (residues 66 (Cys) to 68 (Trp) of SEQ ID NO:93); a domain linker (residues 142 (Thr) to 145 (Pro) of SEQ ID NO:93); a penultimate strand region (residues 207 (Phe) to 215 (Arg) of SEQ ID NO:93); and a C-terminal tail region (residues 534 (Leu) to 547 (Val). Conserved residues common to class I cytokine receptors, are at residues 56 (Cys), 187 (Trp), and 215 (Arg). A comparison of the human and mouse amino acid sequences, including the truncated soluble mouse zcytor17, reveals that both the human and orthologous polypeptides contain corresponding structural features described above (and, see, FIG. 2). The corresponding polynucleotides encoding the truncated soluble mouse zcytor17 polypeptide regions, domains, motifs, residues and sequences described above are as shown in SEQ ID NO:92.

Cytokine receptor subunits are characterized by a multi-domain structure comprising an extracellular domain, a transmembrane domain that anchors the polypeptide in the cell membrane, and an intracellular domain. The extracellular domain may be a ligand-binding domain, and the intracellular domain may be an effector domain involved in signal transduction, although ligand-binding and effector functions may reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of the structure and function. Hematopoietic receptors, for example, are characterized by the presence of a domain containing conserved cysteine residues and the WSXWS motif (SEQ ID NO:3). Cytokine receptor structure has been reviewed by Urdal, *Ann. Reports Med. Chem*. 26:221-228, 1991 and Cosman, *Cytokine* 5:95-106, 1993. Under selective pressure for organisms to acquire new biological functions, new receptor family members likely arise from duplication of existing receptor genes leading to the existence of multi-gene families. Family members thus contain vestiges of the ancestral gene, and these characteristic features can be exploited in the isolation and identification of additional family members. Thus, the cytokine receptor superfamily is subdivided into several families, for example, the immunoglobulin family (including CSF-1, MGF, IL-1, and PDGF receptors); the hematopoietin family (including IL-2 receptor β-subunit, GM-CSF receptor α-subunit, GM-CSF receptor β-subunit; and G-CSF, EPO, IL-3, IL-4, IL-5, IL-6, IL-7, and IL-9 receptors); TNF receptor family (including TNF (p80) TNF (p60) receptors, CD27, CD30, CD40, Fas, and NGF receptor).

Analysis of the zcytor17 sequence suggests that it is a member of the same receptor subfamily as the gp130, LIF, IL-12, WSX-1, IL-2 receptor β-subunit, IL-3, IL-4, and IL-6 receptors. Certain receptors in this subfamily (e.g., G-CSF) associate to form homodimers that transduce a signal. Other members of the subfamily (e.g., gp130, IL-6, IL-11, and LIF receptors) combine with a second subunit (termed a β-subunit) to bind ligand and transduce a signal. Specific β-subunits associate with a plurality of specific cytokine receptor subunits. For example, the β-subunit gp130 (Hibi et al., *Cell* 63:1149-1157, 1990) associates with receptor subunits specific for IL-6, IL-11, and LIF (Gearing et al., *EMBO J.* 10:2839-2848, 1991; Gearing et al., U.S. Pat. No. 5,284,755). Oncostatin M binds to a heterodimer of LIF receptor and gp130. CNTF binds to trimeric receptors comprising CNTF receptor, LIF receptor, and gp 130 subunits.

Those skilled in the art will recognize that the sequences disclosed in SEQ ID NO:1, SEQ ID NO:45 and SEQ ID NO:53 represent alleles of human zcytor17 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, SEQ ID NO:45 or SEQ ID NO:53, including those containing silent mutations and those in which mutations result in amino acid sequence changes, are within the scope of the present invention, as are proteins which are allelic variants of SEQ ID NO:2, SEQ ID NO:46, SEQ ID NO:54 SEQ ID NO:57 or SEQ ID NO:93. cDNAs generated from alternatively spliced mRNAs, which retain the properties of the zcytor17 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. For example, the short-form and long-form soluble zcytor17 receptors described above, and in SEQ ID NO:17 and SEQ ID NO:18 or SEQ ID NO:21 and SEQ ID NO:22 can be considered allelic or splice variants of zcytor17.

The present invention also provides isolated zcytor17 polypeptides that are substantially similar to the polypeptides of SEQ ID NO:2, SEQ ID NO:46 or SEQ ID NO:54 and their orthologs, e.g., SEQ ID NO:57 and SEQ ID NO:93. The term "substantially similar" is used herein to denote polypeptides having at least 70%, more preferably at least 80%, sequence identity to the sequences shown in SEQ ID NO:2, SEQ ID NO:46 or SEQ ID NO:54 or their orthologs, e.g., SEQ ID NO:57 and SEQ ID NO:93. Such polypeptides will more preferably be at least 90% identical, and most preferably 95% or more identical to SEQ ID NO:2, SEQ ID NO:46 and SEQ ID NO:54 or its orthologs.) Percent sequence identity is determined by conventional methods. See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]}\times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |

TABLE 3-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zcytor17. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2, SEQ ID NO:46, SEQ ID NO:54, SEQ ID NO:57 and SEQ ID NO:93) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62, with other parameters set as default. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zcytor17 polypeptides or substantially homologous zcytor17 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag. The present invention thus includes polypeptides that comprise a sequence that is at least 80%, preferably at least 90%, and more preferably 95% or more identical to the corresponding region of SEQ ID NO:2, SEQ ID NO:46, SEQ ID NO:54, SEQ ID NO:57 or SEQ ID NO:93 excluding the tags, extension, linker sequences and the like. Polypeptides comprising affinity tags can further comprise a proteolytic cleavage site between the zcytor17 polypeptide and the affinity tag. Suitable sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a zcytor17 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zcytor17 polypeptide fusions can be expressed in genetically engineered cells to produce a variety of multimeric zcytor17 analogs. Auxiliary domains can be fused to zcytor17 polypeptides to target them to specific cells, tissues, or macromolecules (e.g., collagen). A zcytor17 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zcytor17 amino acid residues.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity (e.g. ligand binding and signal transduction) as disclosed below to identify amino acid residues that are critical to the activity of the molecule. See also, Hilton et al., *J. Biol. Chem.* 271:4699-4708, 1996. Sites of ligand-receptor, protein-protein or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related receptors.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in zcytor17 polypeptides so as to minimize disruption of higher order structure essential to biological activity. For example, when the zcytor17 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same disulfide bonding pattern as the standard molecule folding would be affected. Another well known and accepted method for measuring folding is circular dichroism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961-964, 1992).

A Hopp/Woods hydrophilicity profile of the zcytor17 protein sequence as shown in SEQ ID NO:2, SEQ ID NO:46, SEQ ID NO:54, SEQ ID NO:57 and SEQ ID NO:93 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). See, FIG. 1. The profile is based on a sliding six-residue window. Buried G, S, and T residues and exposed H, Y, and W residues were ignored. For example, in zcytor17, hydrophilic regions include amino acid residues 43 through 48 of SEQ ID NO:2 and SEQ ID NO:46 (residues 56 through 61 of SEQ ID NO:54), amino acid residues 157 through 162 of SEQ ID NO:2 and SEQ ID NO:46 (residues 170 through 175 of SEQ ID NO:54), amino acid residues 158 through 163 of SEQ ID NO:2 and SEQ ID NO:46 (residues 171 through 176 of SEQ ID NO:54), amino acid residues 221 through 226 of SEQ ID NO:2 and SEQ ID NO:46 (residues 234 through 239 of SEQ ID NO:54), and amino acid residues 426 through 431 of SEQ ID NO:2 and SEQ ID NO:46 (residues 439 through 444 of SEQ ID NO:54).

Those skilled in the art will recognize that hydrophilicity or hydrophobicity will be taken into account when designing modifications in the amino acid sequence of a zcytor17 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:2, SEQ ID NO:46, SEQ ID NO:54, SEQ ID NO:57 and SEQ ID NO:93. However, Cysteine residues would be relatively intolerant of substitution.

The identities of essential amino acids can also be inferred from analysis of sequence similarity between class I cytokine receptor family members with zcytor17. Using methods such as "FASTA" analysis described previously, regions of high similarity are identified within a family of proteins and used to analyze amino acid sequence for conserved regions. An alternative approach to identifying a variant zcytor17 polynucleotide on the basis of structure is to determine whether a nucleic acid molecule encoding a potential variant zcytor17 polynucleotide can hybridize to a nucleic acid molecule having the nucleotide sequence of SEQ ID NO:1, SEQ ID NO:45 or SEQ ID NO:53, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996).

The present invention also includes functional fragments of zcytor17 polypeptides and nucleic acid molecules encoding such functional fragments. A "functional" zcytor17 or fragment thereof defined herein is characterized by its proliferative or differentiating activity, by its ability to induce or inhibit specialized cell functions, or by its ability to bind specifically to an anti-zcytor17 antibody or zcytor17 ligand (either soluble or immobilized). Moreover, functional fragments also include the signal peptide, intracellular signaling domain, and the like. As previously described herein, zcytor17 is characterized by a class I cytokine receptor structure. Thus, the present invention further provides fusion proteins encompassing: (a) polypeptide molecules comprising an extracellular domain, cytokine-binding domain, or intracellular domain described herein; and (b) functional fragments comprising one or more of these domains. The other polypeptide portion of the fusion protein may be contributed by another class I cytokine receptor, for example, gp130, LIF, IL-12, WSX-1, IL-2 receptor β-subunit and the β-common receptor (i.e., IL3, IL-5, and GM-CSF receptor β-subunits), or by a non-native and/or an unrelated secretory signal peptide that facilitates secretion of the fusion protein.

Routine deletion analyses of nucleic acid molecules can be performed to obtain functional fragments of a nucleic acid molecule that encodes a zcytor17 polypeptide. As an illustration, DNA molecules having the nucleotide sequence of SEQ ID NO:1, SEQ ID NO:45 or SEQ ID NO:53 or fragments thereof, can be digested with Bal31 nuclease to obtain a series of nested deletions. These DNA fragments are then inserted into expression vectors in proper reading frame, and the expressed polypeptides are isolated and tested for zcytor17 activity, or for the ability to bind anti-zcytor17 antibodies or zcytor17 ligand. One alternative to exonuclease digestion is to use oligonucleotide-directed mutagenesis to introduce deletions or stop codons to specify production of a desired zcytor17 fragment. Alternatively, particular fragments of a zcytor17 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241:53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Variants of the disclosed zcytor17 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized zcytor17 receptor polypeptides in host cells. Preferred assays in this regard include cell proliferation assays and biosensor-based ligand-binding assays, which are described below. Mutagenized DNA molecules that encode active receptors or portions thereof (e.g., ligand-binding fragments, signaling domains, and the like) can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly cytokine receptors, to provide multi-functional molecules. For example, one or more domains from zcytor17 soluble receptor can be joined to other cytokine soluble receptors to enhance their biological properties or efficiency of production.

The present invention thus provides a series of novel, hybrid molecules in which a segment comprising one or more of the domains of zcytor17 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Using the methods discussed herein, one of ordinary skill in the art can identify and/or prepare a variety of polypeptide fragments or variants of SEQ ID NO:2, SEQ ID NO:46, SEQ ID NO:54, SEQ ID NO:57 and SEQ ID NO:93 that retain the signal transduction or ligand binding activity. For example, one can make a zcytor17 "soluble receptor" by preparing a variety of polypeptides that are substantially homologous to the cytokine-binding domain (residues 20 (Ala) to 227 (Pro) of SEQ ID NO:2 and SEQ ID NO:46; residues 33 (Ala) to 240 (Pro) of SEQ ID NO:54), the extracellular domain (residues 20 (Ala) to 519 (Glu) of SEQ ID NO:2 and SEQ ID NO:46; residues 33 (Ala) to 532 (Glu) of SEQ ID NO:54), or allelic variants or species orthologs thereof (e.g., see SEQ ID NO:57 and SEQ ID NO:93 and functional fragments thereof as described herein)) and retain ligand-binding activity of the wild-type zcytor17 protein. Moreover, variant zcytor17 soluble receptors such as those shown in SEQ ID NO:18 and SEQ ID NO:22 can be isolated. Such polypeptides may include additional amino acids from, for example, part or all of the transmembrane and intracellular domains. Such polypeptides may also include additional polypeptide segments as generally disclosed herein such as labels, affinity tags, and the like.

For any zcytor17 polypeptide, including variants, soluble receptors, and fusion polypeptides or proteins, one of ordinary skill in the art can readily generate a fully degenerate polynucleotide sequence encoding that variant using the information set forth in Tables 1 and 2 above.

The zcytor17 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zcytor17 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zcytor17 polypeptide into the secretory pathway of a host cell, a secretory signal sequence (also known as a leader sequence, prepro sequence or pre sequence) is provided in the expression vector. The secretory signal sequence may be that of zcytor17, or may be derived from another secreted protein (e.g., t-PA) or synthesized de novo. The secretory signal sequence is operably linked to the zcytor17 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid 1 (Met) to amino acid 19 (Ala) of SEQ ID NO:2 and SEQ ID NO:46, or wherein a secretory signal sequence derived from amino acid 1 (Met) to amino acid 32 (Ala) of SEQ ID NO:54, or amino acid 1 (Met) to amino acid 45 (Ala) of SEQ ID NO:57 or SEQ ID NO:93), or amino acid 28 (Met) to residue 45 (Ala) of SEQ ID NO:57 or SEQ ID NO:93), is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., Focus 15:73, 1993; Ciecarone et al., *Focus* 15:80, 1993, and viral vectors (Miller and Rosman, BioTechniques 7:980-90, 1989; Wang and Finer, *Nature Med.* 2:714-716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol*. 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Bangalore*) 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zcytor17 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zcytor17 polypeptide into a baculovirus genome maintained in *E. coli* as a large plasmid called a "bacmid." See, Hill-Perkins, M. S, and Possee, R. D., *J Gen Virol* 71:971-6, 1990; Bonning, B. C. et al., *J Gen Virol* 75:1551-6, 1994; and, Chazenbalk, G. D., and Rapoport, B., *J Biol Chem* 270:1543-9, 1995. In addition, transfer vectors can include an in-frame fusion with DNA encoding an epitope tag at the C- or N-terminus of the expressed zcytor17 polypeptide, for example, a Glu-Glu epitope tag (Grussenmeyer, T. et al., *Proc. Natl. Acad. Sci.* 82:7952-4, 1985). Using a technique known in the art, a transfer vector containing zcytor17 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zcytor17 is subsequently produced. Recombinant viral stocks are made by methods commonly used in the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF921™ (Expression Systems) for the Sf9 cells; and Ex-cellO405™ (JRH Biosciences, Lenexa, Kans.) or Express FiveO™ (Life Technologies) for the *T. ni* cells. Procedures used are generally described in available laboratory manuals (King, L. A. and Possee, R. D., ibid.; O'Reilly, D. R. et al., ibid.; Richardson, C. D., ibid.). Subsequent purification of the zcytor17 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zcytor17 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a zcytor17 cytokine receptor (including transmembrane and intracellular domains) is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing the novel receptors of the present invention and transducing a receptor-mediated signal include cells that express a β-subunit, such as gp130, and cells that co-express gp130 and LIF receptor (Gearing et al., *EMBO J.* 10:2839-2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include BaF3 cells (Palacios and Steinmetz, *Cell* 41: 727-734, 1985; Mathey-Prevot et al., *Mol. Cell. Biol.* 6: 4133-4135, 1986), the human TF-1 cell line (ATCC number CRL-2003) and the DA-1 cell line (Branch et al., *Blood* 69:1782, 1987; Broudy et al., *Blood* 75:1622-1626, 1990). In the alternative, suitable host cells can be engineered to produce a β-subunit or other cellular component needed for the desired cellular response. For example, the murine cell line BaF3 (Palacios and Steinmetz, *Cell* 41:727-734, 1985; Mathey-Prevot et al., *Mol. Cell. Biol.* 6: 4133-4135, 1986), a baby hamster kidney (BHK) cell line, or the CTLL-2 cell line (ATCC TIB-214) can be transfected to express the mouse gp130 subunit, or mouse gp130 and LIF receptor, in addition to zcytor17. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a zcytor17 ligand or anti-zcytor17 antibody.

Cells expressing functional zcytor17 are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the reduction or metabolic breakdown of Alymar Blue™ (AccuMed, Chicago, Ill.) or 3-(4,5-dimethylthiazol-2-yl)-2,5-diphenyl tetrazolium bromide (MTT) (Mosman, *J. Immunol. Meth*. 65: 55-63, 1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, STAT or SRE (see, for example, Shaw et al., *Cell* 56:563-572, 1989). A preferred such reporter gene is a luciferase gene (de Wet et al., *Mol. Cell. Biol*. 7:725, 1987). Expression of the luciferase gene is detected by luminescence using methods known in the art (e.g., Baumgartner et al., *J. Biol. Chem*. 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell- or tissue-conditioned media samples can be assayed on a target cell to identify cells that produce ligand. Positive cells are then used to produce a cDNA library in a mammalian cell expression vector, which is divided into pools, transfected into host cells, and expressed. Media samples from the transfected cells are then assayed, with subsequent division of pools, retransfection, subculturing, and re-assay of positive cells to isolate a clonal cell line expressing the ligand. Media samples conditioned by kidney, liver, spleen, thymus, other lymphoid tissues, or T-cells are preferred sources of ligand for use in screening procedures.

A natural ligand for zcytor17 can also be identified by mutagenizing a cytokine-dependent cell line expressing zcytor17 and culturing it under conditions that select for autocrine growth. See WIPO publication WO 95/21930. Within a typical procedure, cells expressing zcytor17 are mutagenized, such as with EMS. The cells are then allowed to recover in the presence of the required cytokine, then transferred to a culture medium lacking the cytokine. Surviving cells are screened for the production of a ligand for zcytor17, such as by adding soluble receptor polypeptide comprising the zcytor17 cytokine-binding domain described herein to the culture medium to compete against the ligand or by assaying conditioned media on wild-type cells compared to transfected cells expressing the zcytor17 receptor. Preferred cell lines for use within this method include cells that are transfected to express gp130 or gp130 in combination with LIF receptor. Preferred such host cell lines include transfected CTLL-2 cells (Gillis and Smith, *Nature* 268:154-156, 1977) and transfected BaF3 cells.

Moreover, a secretion trap method employing zcytor17 soluble receptor polypeptide can be used to isolate a zcytor17 ligand (Aldrich, et al, *Cell* 87: 1161-1169, 1996). A cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled zcytor17 soluble receptor, described herein, is then placed in contact with the cell layer and allowed to bind cells in the monolayer that express an anti-complementary molecule, i.e., a zcytor17 ligand. A cell expressing a ligand will thus be bound with receptor molecules. An anti-tag antibody (anti-Ig for Ig fusions, M2 or anti-FLAG for FLAG-tagged fusions, streptavidin, anti-Glu-Glu tag, and the like) which is conjugated with horseradish peroxidase (HRP) is used to visualize these cells to which the tagged or biotin-labeled zcytor17 soluble receptor has bound. The HRP catalyzes deposition of a tyramide reagent, for example, tyramide-FITC. A commercially-available kit can be used for this detection (for example, Renaissance TSA-Direct™ Kit; NEN Life Science Products, Boston, Mass.). Cells which express zcytor17 receptor ligand will be identified under fluorescence microscopy as green cells and picked for subsequent cloning of the ligand using procedures for plasmid rescue as outlined in Aldrich, et al, supra., followed by subsequent rounds of secretion trap assay, or conventional screening of cDNA library pools, until single clones are identified.

As a receptor, the activity of zcytor17 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol*. 228:84-108, 1997; Arimilli, S. et al., *J. Immunol. Meth*. 212:49-59, 1998; Van Liefde, I. Et al., *Eur. J. Pharmacol*. 346:87-95, 1998. The microphysiometer can be used for assaying eukaryotic, prokaryotic, adherent or non-adherent cells. By measuring extracellular acidification changes in cell media over time, the microphysiometer directly measures cellular responses to various stimuli, including agonists, ligands, or antagonists of the zcytor17 polypeptide. Preferably, the microphysiometer is used to measure responses of a zcytor17-expressing eukaryotic cell, compared to a control eukaryotic cell that does not express zcytor17 polypeptide. Zcytor17-expressing eukaryotic cells comprise cells into which zcytor17 has been transfected or infected via adenovirus vector, and the like, as described herein, creating a cell that is responsive to zcytor17-modulating stimuli, or are cells naturally expressing zcytor17, such as zcytor17-expressing cells derived from lymphoid, spleen, thymus tissue or PBLs. Differences, measured by an increase or decrease in extracellular acidification, in the response of cells expressing zcytor17, relative to a control, are a direct measurement of zcytor17-modulated cellular responses. Moreover, such zcytor17-modulated responses can be assayed under a variety of stimuli. Also, using the microphysiometer, there is provided a method of identifying agonists and antagonists of zcytor17 polypeptide, comprising providing cells expressing a zcytor17 polypeptide, culturing a first portion of the cells in the absence of a test compound, culturing a second portion of the cells in the presence of a test compound, and detecting an increase or a decrease in a cellular response of the second portion of the cells as compared to the first portion of the cells. Antagonists and agonists, including the natural ligand for zcytor17 polypeptide, can be rapidly identified using this method.

Additional assays provided by the present invention include the use of hybrid receptor polypeptides. These hybrid polypeptides fall into two general classes. Within the first class, the intracellular domain of zcytor17, comprising approximately residues 544 (Lys) to 732 (Val) of SEQ ID NO:2, residues 544 (Lys) to 649 (Ile) of SEQ ID NO:46, or residues 557 (Lys) to 662 (Ile) of SEQ ID NO:54, or residues 551 (Lys) to 662 (Cys) of SEQ ID NO:57 is joined to the ligand-binding domain of a second receptor. It is preferred that the second receptor be a hematopoietic cytokine receptor, such as mpl receptor (Souyri et al., *Cell* 63:1137-1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by zcytor17 while using readily available ligands. This system can also be used to determine if particular cell lines are capable of responding to signals transduced by zcytor17. A second class of hybrid receptor polypeptides comprise the extracellular (ligand-binding) domain (approximately residues 20 (Ala) to 519 (Glu) of SEQ ID NO:2 and SEQ ID NO:46; approximately residues 33 (Ala) to 532 (Glu) of SEQ ID NO:54) or cytokine-binding domain of zcytor17 (approximately residues 20 (Ala) to 227 (Pro) of SEQ ID NO:2 and SEQ ID NO:46; or approximately residues 33 (Ala) to 240 (Pro) of SEQ ID NO:54; approximately residues 46 (Val) to 533 (Glu) of SEQ ID NO:57; or approximately residues 46 (Val) to 533 (Trp) of SEQ ID NO:93) with a cytoplasmic domain of a second receptor, preferably a cytokine receptor, and a transmembrane domain. The transmembrane domain may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

Cells found to express a ligand for zcytor17 are then used to prepare a cDNA library from which the ligand-encoding cDNA may be isolated as disclosed above. The present invention thus provides, in addition to novel receptor polypeptides, methods for cloning polypeptide ligands for the receptors.

The zcytor17 structure and tissue expression suggests a role in early hematopoietic or thymocyte development and immune response regulation or inflammation. These processes involve stimulation of cell proliferation and differentiation in response to the binding of one or more cytokines to their cognate receptors. In view of the tissue distribution observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds or antizcytor17 antibodies, are useful as components of defined cell culture media, and may be used alone or in combination with other cytokines and hormones to replace serum that is commonly used in cell culture. Agonists are thus useful in specifically promoting the growth and/or development or activation of monocytes, T-cells, B-cells, and other cells of the lymphoid and myeloid lineages, and hematopoietic cells in culture.

Agonist ligands for zcytor17, or anti-zcytor17 antibodies and binding partners, may be useful in stimulating cell-mediated immunity and for stimulating lymphocyte proliferation, such as in the treatment of infections involving immunosuppression, including certain viral infections. Additional uses include tumor suppression, where malignant transformation results in tumor cells that are antigenic. Agonist ligands or anti-zcytor17 antibodies and binding partners could be used to induce cytotoxicity, which may be mediated through activation of effector cells such as T-cells, NK (natural killer) cells, or LAK (lymphoid activated killer) cells, or induced directly through apoptotic pathways. Agonist ligands, anti-zcytor17 antibodies and binding partners may also be useful in treating leukopenias by increasing the levels of the affected cell type, and for enhancing the regeneration of the T-cell repertoire after bone marrow transplantation; or for enhancing monocyte proliferation or activation, and far diagnostic and other uses described herein.

Antagonist ligands, compounds, or anti-zcytor17 antibodies may find utility in the suppression of the immune system, such as in the treatment of autoimmune diseases, including rheumatoid arthritis, multiple sclerosis, diabetes mellitis, inflammatory bowel disease, Crohn's disease, etc. Immune suppression can also be used to reduce rejection of tissue or organ transplants and grafts and to treat T-cell, B-cell or monocyte-specific leukemias or lymphomas, and other immune cell cancers, by inhibiting proliferation of the affected cell type. Moreover zcytor17 polynucleotides, anti-zcytor17 antibodies and binding partners can be used to detect monocytes, and aid in the diagnosis of such autoimmune disease, particularly in disease states where monocytes are elevated or activated.

Zcytor17 polypeptides may also be used within diagnostic systems for the detection of circulating levels of ligand. Within a related embodiment, antibodies or other agents that specifically bind to zcytor17 receptor polypeptides can be used to detect circulating receptor polypeptides. Zcytor17 appears to be naturally-expressed as a soluble receptor as shown by the soluble receptor forms shown in SEQ ID NO:18 and SEQ ID NO:22. Elevated or depressed levels of ligand or receptor polypeptides may be indicative of pathological conditions, including cancer. Soluble receptor polypeptides may contribute to pathologic processes and can be an indirect marker of an underlying disease. For example, elevated levels of soluble IL-2 receptor in human serum have been associated with a wide variety of inflammatory and neoplastic conditions, such as myocardial infarction, asthma, myasthenia gravis, rheumatoid arthritis, acute T-cell leukemia, B-cell lymphomas, chronic lymphocytic leukemia, colon cancer, breast cancer, and ovarian cancer (Heaney et al., Blood 87:847-857, 1996). Similarly, zcytor17 is elevated in activated monocytes, and hence zcytor17 and/or its soluble receptors may be associated with or serve as a marker for inflammatory and neoplastic conditions associated therewith.

A ligand-binding polypeptide of a zcytor17 receptor, or "soluble receptor," can be prepared by expressing a truncated DNA encoding the zcytor17 cytokine binding domain (approximately residue 20 (Ala) through residue 227 (Pro) of the human receptor SEQ ID NO:2 and SEQ ID NO:46; approximately residue 33 (Ala) through residue 240 (Pro) of the human receptor SEQ ID NO:54), or the extracellular domain (approximately residue 20 (Ala) through residue 519 (Glu) of SEQ ID NO:2 and SEQ ID NO:46; approximately residue 33 (Ala) through residue 532 (Glu) of SEQ ID NO:54), or the corresponding region of a non-human receptor, e.g., such as the corresponding regions described herein for SEQ ID NO:57 and SEQ ID NO:93. It is preferred that the extracellular domain be prepared in a form substantially free of transmembrane and intracellular polypeptide segments. Moreover, ligand-binding polypeptide fragments within the zcytor17 cytokine binding domain, described above, can also serve as zcytor17 soluble receptors for uses described herein. To direct the export of a receptor polypeptide from the host cell, the receptor DNA is linked to a second DNA segment encoding a secretory peptide, such as a t-PA secretory peptide or a zcytor17 secretory peptide. To facilitate purification of the secreted receptor polypeptide, a C-terminal extension, such as a poly-histidine tag, Glu-Glu tag peptide, substance P, Flag™ peptide (Hopp et al., *Bio/Technology* 6:1204-1210, 1988; available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_c$ fragment (e.g., Fc4), which contains two constant region domains and lacks the variable region. Such fusions are typically secreted as multimeric molecules wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a zcytor17-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Collected fractions can be re-fractionated until the desired level of purity is reached.

Moreover, zcytor17 soluble receptors can be used as a "ligand sink," i.e., antagonist, to bind ligand in vivo or in vitro in therapeutic or other applications where the presence of the ligand is not desired. For example, in cancers that are expressing large amount of bioactive zcytor17 ligand, zcytor17 soluble receptors can be used as a direct antagonist of the ligand in vivo, and may aid in reducing progression and symptoms associated with the disease. Moreover, zcytor17 soluble receptor can be used to slow the progression of cancers that over-express zcytor17 receptors, by binding ligand in vivo that would otherwise enhance proliferation of those cancers. Similar in vitro applications for a zcytor17 soluble receptor can be used, for instance, as a negative selection to select cell lines that grow in the absence of zcytor17 ligand.

Moreover, zcytor17 soluble receptor can be used in vivo or in diagnostic applications to detect zcytor17 ligand-expressing cancers in vivo or in tissue samples. For example, the zcytor17 soluble receptor can be conjugated to a radio-label or fluorescent label as described herein, and used to detect the presence of the ligand in a tissue sample using an in vitro ligand-receptor type binding assay, or fluorescent imaging assay. Moreover, a radiolabeled zcytor17 soluble receptor could be administered in vivo to detect ligand-expressing solid tumors through a radio-imaging method known in the art.

The molecules of the present invention have particular use in the monocyte/macrophage arm of the immune system. For example, interferon gamma (IFNγ) is a potent activator of mononuclear phagocytes. The increase in expression of zcytor17 upon activation of THP-1 cells (ATCC No. TIB-202) with interferon gamma suggests that this receptor is involved in monocyte activation. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation. Moreover, monocyte-macrophage function has been shown to be abnormal in a variety of diseased states. For example see, Johnston, R B, *New Eng. J. Med*. 318:747-752, 1998.

One of skill in the art would recognize that agonists of zcytor17 are useful. For example, depressed migration of monocytes has been reported in populations with a predisposition to infection, such as newborn infants, patients receiving corticosteroid or other immunosuppressive therapy, and patients with diabetes mellitus, burns, or AIDS. Agonists for zcytor17, such as anti-zcytor17 antibodies and binding partners, as well as the natural ligand, could result in an increase in ability of monocytes to migrate and possibly prevent infection in these populations. There is also a profound defect of phagocytic killing by mononuclear phagocytes from patients with chronic granulomatous disease. This results in the formation of subcutaneous abscesses, as well as abscesses in the liver, lungs, spleen, and lymph nodes. An agonist of zcytor17 such as anti-zcytor17 antibodies and binding partners, as well as the natural ligand, could correct or improve this phagocytic defect. In addition, defective monocyte cytotoxicity has been reported in patients with cancer and Wiskott-Aldrich syndrome (eczema, thrombocytopenia, and recurrent infections). Activation of monocytes by agonists of zcytor17 such as anti-zcytor17 antibodies and binding partners, as well as the natural ligand, could aid in treatment of these conditions. The monocyte-macrophage system is prominently involved in several lipid-storage diseases (sphingolipidoses) such as Gaucher's disease. Resistance to infection can be impaired because of a defect in macrophage function, which could be treated by agonists to zcytor17 such as anti-zcytor17 antibodies and binding partners, as well as the natural ligand.

Moreover, one of skill in the art would recognize that antagonists of zcytor17 are useful. For example, in atherosclerotic lesions, one of the first abnormalities is localization of monocyte/macrophages to endothelial cells. These lesions could be prevented by use of antagonists to zcytor17. Anti-zcytor17 antibodies and binding partners can also be used as antagonists to the natural ligand of zcytor17. Moreover, monoblastic leukemia is associated with a variety of clinical abnormalities that reflect the release of the biologic products of the macrophage, examples include high levels of lysozyme in the serum and urine and high fevers. Moreover, such leukemias exhibit an abnormal increase of monocytic cells. These effects could possibly be prevented by antagonists to zcytor17, such as described herein. Moreover, anti-zcytor17 antibodies and binding partners can be conjugated to molecules such as toxic moieties and cytokines, as described herein to direct the killing of leukemia monocytic cells.

Using methods known in the art, and disclosed herein, one of skill could readily assess the activity of zcytor17 agonists and antagonists in the disease states disclosed herein, inflammation, cancer, or infection as well as other disease states involving monocytic cells. In addition, as zcytor17 is expressed in a monocyte-specific manner, and these diseases involve abnormalities in monocytic cells, such as cell proliferation, function, localization, and activation, the polynucleotides, polypeptides, and antibodies of the present invention can be used to as diagnostics to detect such monocytic cell abnormalities, and indicate the presence of disease. Such methods involve taking a biological sample from a patient, such as blood, saliva, or biopsy, and comparing it to a normal control sample. Histological, cytological, flow cytometric, biochemical and other methods can be used to determine the relative levels or localization of zcytor17, or cells expressing zcytor17, i.e., monocytes, in the patient sample compared to the normal control. A change in the level (increase or decrease) of zcytor17 expression, or a change in number or localization of monocytes (e.g., increase or infiltration of monocytic cells in tissues where they are not normally present) compared to a control would be indicative of disease. Such diagnostic methods can also include using radiometric, fluorescent, and colorimetric tags attached to polynucleotides, polypeptides or antibodies of the present invention. Such methods are well known in the art and disclosed herein.

Amino acid sequences having Zcytor17 activity can be used to modulate the immune system by binding Zcytor17 ligand, and thus, preventing the binding of Zcytor17 ligand with endogenous Zcytor17 receptor. Zcytor17 antagonists, such as anti-Zcytor17 antibodies, can also be used to modulate the immune system by inhibiting the binding of Zcytor17 ligand with the endogenous Zcytor17 receptor. Accordingly, the present invention includes the use of proteins, polypeptides, and peptides having Zcytor17 activity (such as Zcytor17 polypeptides, Zcytor17 analogs (e.g., anti-Zcytor17 anti-idiotype antibodies), and Zcytor17 fusion proteins) to a subject which lacks an adequate amount of this polypeptide, or which produces an excess of Zcytor17 ligand. Zcytor17 antagonists (e.g., anti-Zcytor17 antibodies) can be also used to treat a subject which produces an excess of either Zcytor17 ligand or Zcytor17. Suitable subjects include mammals, such as humans.

Zcytor17 has been shown to be upregulated in monocyte cells, and may be involved in regulating inflammation. As such, polypeptides of the present invention can be assayed and used for their ability to modify inflammation, or can be used as a marker for inflammation. Methods to determine proinflammatory and antiinflammatory qualities of zcytor17 are known in the art and discussed herein. Moreover, it may be involved in up-regulating the production of acute phase reactants, such as serum amyloid A (SAA), α1-antichymotrypsin, and haptoglobin, and that expression of zcytor17 ligand may be increased upon injection of lipopolysaccharide (LPS) in vivo that are involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, J. *Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand for zcytor17 that acts as a pro-inflammatory molecule and induces production of SAA, antagonists would be useful in treating inflammatory disease and other diseases associated with acute phase response proteins induced by the ligand. Such antagonists are provided by the present invention. For example, a method of reducing inflammation comprises administering to a mammal with inflammation an amount of a composition of soluble zcytor17-comprising receptor, or anti-zcytor17 antibody that is sufficient to reduce inflammation. Moreover, a method of suppressing an inflammatory response in a mammal with inflammation can comprise: (1) determining a level of serum amyloid A protein; (2) administering a composition comprising a soluble zcytor17 cytokine receptor polypeptide as described herein in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

The receptors of the present invention include at least one zcytor17 receptor subunit. A second receptor polypeptide included in the heterodimeric soluble receptor belongs to the receptor subfamily that includes class I cytokine receptor subunits. According to the present invention, in addition to a monomeric or homodimeric zcytor17 receptor polypeptide, a heterodimeric soluble zcytor17 receptor, as exemplified by an embodiment comprising a soluble zcytor17 receptor+soluble Class I receptor heterodimeric component, can act as an antagonist of the natural zcytor17 ligand. Other embodiments include soluble multimeric receptors comprising zcytor17.

Analysis of the tissue distribution of the mRNA corresponding zcytor17 cDNA showed that mRNA level was highest in monocytes and prostate cells, and is elevated in activated monocytes, and activated CD4+, activated CD8+, and activated CD3+ cells. Hence, zcytor17 is implicated in inducing inflammatory and immune response. Thus, particular embodiments of the present invention are directed toward use of soluble zcytor17 heterodimers as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of zcytor178 expression in activated immune cells such as activated CD4+ and CD19+ cells showed that zcytor17 may be involved in the body's immune defensive reactions against foreign invaders: such as microorganisms and cell debris, and could play a role in immune responses during inflammation and cancer formation. As such, antibodies and binding partners of the present invention that are agonistic or antagonistic to zcytor17 function, can be used to modify immune response and inflammation.

Moreover, antibodies or binding polypeptides that bind zcytor17 polypeptides, monomers, homodimers, heterodimers and multimers described herein and/or zcytor17 polypeptides, monomers, homodimers, heterodimers and multimers themselves are useful to:

Antagonize or block signaling via the zcytor17 receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Antagonize or block signaling via the zcytor17 receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via zcytor17 (Hughes C et al., *J. Immunol*

153: 3319-3325, 1994). Alternatively antibodies, such as monoclonal antibodies (MAb) to zcytor17-comprising receptors, can also be used as an antagonist to deplete unwanted immune cells to treat autoimmune disease. Asthma, allergy and other atopic disease may be treated with an MAb against, for example, soluble zcytor17 soluble receptors or zcytor17/CRF2-4 heterodimers, to inhibit the immune response or to deplete offending cells. Blocking or inhibiting signaling via zcytor17, using the polypeptides and antibodies of the present invention, may also benefit diseases of the pancreas, kidney, pituitary and neuronal cells. IDDM, NIDDM, pancreatitis, and pancreatic carcinoma may benefit. Zcytor17 may serve as a target for MAb therapy of cancer where an antagonizing MAb inhibits cancer growth and targets immune-mediated killing. (Holliger P, and Hoogenboom, H: *Nature Biotech*. 16: 1015-1016, 1998). Mabs to soluble zcytor17 monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

Agonize or initiate signaling via the zcytor17 receptors in the treatment of autoimmune diseases such as IDDM, MS, SLE, myasthenia gravis, rheumatoid arthritis, and IBD. Anti-zcytor17, anti-heterodimer and multimer monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol*. 160:4841-4849, 1998). Similarly, agonistic anti-zcytor17, anti-heterodimer and multimer monoclonal antibodies may be used to signal, deplete and deviate immune cells involved in asthma, allergy and atopoic disease. Signaling via zcytor17 may also benefit diseases of the pancreas, kidney, pituitary and neuronal cells. IDDM, NIDDM, pancreatitis, and pancreatic carcinoma may benefit. Zcytor17 may serve as a target for MAb therapy of pancreatic cancer where a signaling MAb inhibits cancer growth and targets immune-mediated killing (Tutt, A L et al., *J. Immunol*. 161: 3175-3185, 1998). Similarly T-cell specific leukemias, lymphomas, and carcinoma may be treated with monoclonal antibodies to zcytor17-comprising soluble receptors of the present invention.

Soluble zcytor17 monomeric, homodimeric, heterodimeric and multimeric polypeptides described herein can be used to neutralize/block zcytor17 ligand activity in the treatment of autoimmune disease, atopic disease, NIDDM, pancreatitis and kidney dysfunction as described above. A soluble form of zcytor17 may be used to promote an antibody response mediated by T cells and/or to promote the production of IL-4 or other cytokines by lymphocytes or other immune cells.

The soluble zcytor17-comprising receptors of the present invention are useful as antagonists of its natural ligand. Such antagonistic effects can be achieved by direct neutralization or binding of its natural ligand. In addition to antagonistic uses, the soluble receptors of the present invention can bind zcytor17 ligand and act as carrier proteins for the ligand, in order to transport the ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, monocytes, or tumor. For example, in acute infection or some cancers, benefit may result from induction of inflammation and local acute phase response proteins. Thus, the soluble receptors of the present invention can be used to specifically direct the action of a pro-inflammatory ligand. See, Cosman, D. *Cytokine* 5: 95-106, 1993; and Fernandez-Botran, R. *Exp. Opin. Invest. Drugs* 9:497-513, 2000.

Moreover, the soluble receptors of the present invention can be used to stabilize the zcytor17 ligand, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Fernandez-Botran, R. supra. Moreover, Zcytor17 may be combined with a cognate ligand such as its ligand to comprise a ligand/soluble receptor complex. Such complexes may be used to stimulate responses from cells presenting a companion receptor subunit. The cell specificity of zcytor17/ligand complexes may differ from that seen for the ligand administered alone. Furthermore the complexes may have distinct pharmacokinetic properties such as affecting half-life, dose/response and organ or tissue specificity. Zcytor17/ligand complexes thus may have agonist activity to enhance an immune response or stimulate mesangial cells or to stimulate hepatic cells. Alternatively only tissues expressing a signaling subunit the heterodimerizes with the complex may be affected analogous to the response to IL6/IL6R complexes (Hirota H. et al., *Proc. Nat'l. Acad. Sci*. 92:4862-4866, 1995; Hirano, T. in Thomason, A. (Ed.) "The Cytokine Handbook", 3$^{rd}$ Ed., p. 208-209). Soluble receptor/cytokine complexes for IL12 and CNTF display similar activities.

Zcytor17 homodimeric, heterodimeric and multimeric receptor polypeptides may also be used within diagnostic systems for the detection of circulating levels of ligand, and in the detection of acute phase inflammatory response. Within a related embodiment, antibodies or other agents that specifically bind to Zcytor17 soluble receptors of the present invention can be used to detect circulating receptor polypeptides; conversely, Zcytor17 soluble receptors themselves can be used to detect circulating or locally-acting ligand polypeptides. Elevated or depressed levels of ligand or receptor polypeptides may be indicative of pathological conditions, including inflammation or cancer. Moreover, detection of acute phase proteins or molecules such as zcytor17 ligand can be indicative of a chronic inflammatory condition in certain disease states (e.g., rheumatoid arthritis). Detection of such conditions serves to aid in disease diagnosis as well as help a physician in choosing proper therapy.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondroeytes, fibroblasts and reticular cells are believed to originate from a common mesenchymal stem cell (Owen et al., *Ciba Fdn. Symp*. 136:42-46, 1988). Markers for mesenchymal stem cells have not been well identified (Owen et al., *J. of Cell Sci*. 87:731-738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate or regulate specific cell types down a pathway towards terminal differentiation or dedifferentiation affect the entire cell population originating from a common precursor or stem cell. Thus, the present invention includes stimulating or inhibiting the proliferation of lymphoid cells, hematopoietic cells and endothelial cells. Thus molecules of the present invention, such as soluble zcytor17 receptors, cytokine-binding fragments, anti-zcytor17 antibodies, sense and antisense polynucleotides may have use in inhibiting tumor cells, and particularly lymphoid, hematopoietic, prostate, endothelial, and thyroid tumor cells.

Assays measuring differentiation include, for example, measuring cell markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference). Alternatively, zcytor17 polypeptide itself can serve as an additional cell-surface or secreted marker associated with stage-specific expression of a tissue. As such, direct measurement of zcytor17 polypeptide, or its loss of expression in a tissue as it differentiates, can serve as a marker for identification or differentiation of, e.g., prostate tissue, or monocyte cells.

Similarly, direct measurement of zcytor17 polypeptide, or its loss of expression in a tissue can be determined in a tissue or cells as they undergo tumor progression. Increases in invasiveness and motility of cells, or the gain or loss of expression of zcytor17 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zcytor17 expression. For example, appearance or disappearance of polypeptides that regulate cell motility can be used to aid diagnosis and prognosis of prostate cancer (Banyard, J. and Zetter, B. R., *Cancer and Metast. Rev*. 17:449-458, 1999). As an effector of cell motility, activation, proliferation, or differentiation, zcytor17 gain or loss of expression may serve as a diagnostic for lymphoid, hematopoietic, prostate, endothelial, and thyroid and other cancers.

In addition, as zcytor17 is monocyte and prostate-specific, polynucleotide probes, anti-zcytor17 antibodies, and detection the presence of zcytor17 polypeptides in tissues can be used to assess whether monocytes or prostate tissue is present, for example, after surgery involving the excision of a diseased or cancerous prostate, or in evaluation of monocyte infiltration in diseased or infected tissues or monocyte cancers. As such, the polynucleotides, polypeptides, and antibodies of the present invention can be used as an aid to determine whether all prostate tissue is excised after surgery, for example, after surgery for prostate cancer. In such instances, it is especially important to remove all potentially diseased tissue to maximize recovery from the cancer, and to minimize recurrence. Moreover, the polynucleotides, polypeptides, and antibodies of the present invention can be used as an aid to determine whether monocyte infiltration is present in diseased tissues (e.g., inflamed or infected) to monitor the recovery from disease or cancers. Preferred embodiments include fluorescent, radiolabeled, or calorimetrically labeled anti-zcytor17 antibodies and zcytor17 polypeptide binding partners, that can be used histologically or in situ.

Moreover, the activity and effect of zcytor17 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zcytor17, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zcytor17, on the ability of the tumor to recruit vasculature and undergo metastasis can thus be assessed. In addition, aside from using adenovirus, the implanted cells can be transiently transfected with zcytor17. Use of stable zcytor17 transfectants as well as use of inducible promoters to activate zcytor17 expression in vivo are known in the art and can be used in this system to assess zcytor17 induction of metastasis. Moreover, purified zcytor17 or zcytor17 conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

The activity of zcytor17 and its derivatives (conjugates) on growth and dissemination of tumor cells derived from human hematologic malignancies can also be measured in vivo in a mouse Xenograft model Several mouse models have been developed in which human tumor cells are implanted into immunodeficient mice, collectively referred to as xenograft models. See Caftan, A R and Douglas, E *Leuk. Res*. 18:513-

22, 1994; and Flavell, D J, *Hematological Oncology* 14:67-82, 1996. The characteristics of the disease model vary with the type and quantity of cells delivered to the mouse. Typically, the tumor cells will proliferate rapidly and can be found circulating in the blood and populating numerous organ systems. Therapeutic strategies appropriate for testing in such a model include antibody induced toxicity, ligand-toxin conjugates or cell-based therapies. The latter method, commonly referred to adoptive immunotherapy, involves treatment of the animal with components of the human immune system (i.e. lymphocytes, NK cells) and may include ex vivo incubation of cells with zcytor17 or other immunomodulatory agents.

The mRNA corresponding to this novel DNA showed expression in lymphoid tissues, including thymus, is expressed in bone marrow and prostate, monocytes, and activated monocytes, CD19+ B-cells, and may be expressed in spleen, lymph nodes, and peripheral blood leukocytes. These data indicate a role for the zcytor17 receptor in proliferation, differentiation, and/or activation of immune cells, and suggest a role in development and regulation of immune responses. The data also suggest that the interaction of zcytor17 with its ligand may stimulate proliferation and development of myeloid cells and may, like IL-2, IL-6, LIF, IL-11, IL-12 and OSM (Baumann et al., *J. Biol. Chem*. 268:8414-8417, 1993), induce acute-phase protein synthesis in hepatocytes.

It is preferred to purify the polypeptides of the present invention to ≥80% purity, more preferably to ≥90% purity, even more preferably ≥95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zcytor17 polypeptides (or zcytor17 chimeric or fusion polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their biochemical, structural, and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem*. 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol., Vol*. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid zcytor17 proteins, are constructed using regions or domains of the inventive zcytor17 in combination with those of other human cytokine receptor family proteins, or heterologous proteins (Sambrook et al., ibid., Altschul et al., ibid., Picard, *Cur. Opin. Biology*, 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion polypeptides or proteins can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zcytor17 of the present invention with the functionally equivalent domain(s) from another cytokine family member. Such domains include, but are not limited to, the secretory signal sequence, extracellular domain, cytokine binding domain, fibronectin type III domain, transmembrane domain, and intracellular signaling domain, Box I and Box II sites, as disclosed herein. Such fusion proteins would be expected to have a biological functional profile that is the same or similar to polypeptides of the present invention or other known family proteins, depending on the fusion constructed. Moreover, such fusion proteins may exhibit other properties as disclosed herein.

Standard molecular biological and cloning techniques can be used to swap the equivalent domains between the zcytor17 polypeptide and those polypeptides to which they are fused. Generally, a DNA segment that encodes a domain of interest, e.g., a zcytor17 domain described herein, is operably linked in frame to at least one other DNA segment encoding an additional polypeptide (for instance a domain or region from another cytokine receptor, such as the gp130, LIF, IL-12, WSX-1, IL-2 or other class I cytokine receptor), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a cytokine binding domain, followed by a transmembrane domain, followed by an intracellular signaling domain. Such fusion proteins can be expressed, isolated, and assayed for activity as described herein. Moreover, such fusion proteins can be used to express and secrete fragments of the zcytor17 polypeptide, to be used, for example to inoculate an animal to generate anti-zcytor17 antibodies as described herein. For example a secretory signal sequence can be operably linked to the cytokine binding domain, transmembrane domain, intracellular signaling domain or subfragment thereof, or a combination thereof (e.g., operably linked polypeptides comprising the extracellular cytokine binding domain fused to a transmembrane domain, or zcytor17 polypeptide fragments described herein), to secrete a fragment of zcytor17 polypeptide that can be purified as described herein and serve as an antigen to be inoculated into an animal to produce anti-zcytor17 antibodies, as described herein.

Zcytor17 polypeptides or fragments thereof may also be prepared through chemical synthesis. zcytor17 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem*. 34:595, 1970. After the entire synthesis of the desired peptide on a solid support, the peptide-resin is with a reagent which cleaves the polypeptide from the resin and removes most of the side-chain protecting groups. Such methods are well established in the art.

The activity of molecules of the present invention can be measured using a variety of assays that measure cell differentiation and proliferation. Such assays are well known in the art.

Proteins of the present invention are useful for example, in treating and diagnosing lymphoid, immune, inflammatory, spleenic, blood or bone disorders, and can be measured in vitro using cultured cells or in vivo by administering molecules of the present invention to the appropriate animal model. For instance, host cells expressing a zcytor17 soluble receptor polypeptide can be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells. These types of non-immunogenic "encapsulations" permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for generating embedded cells.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of the Lactated Ringer's Solution.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol*. 43:161-89, 1994; and J. T. Douglas and D. T. Curiel, *Science* & *Medicine* 4:44-53, 1997). The adenovirus system offers several advantages: (i) adenovirus can accommodate relatively large DNA inserts; (ii) can be grown to high-titer; (iii) infect a broad range of mammalian cell types; and (iv) can be used with a large number of different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol*. 72:2022-2032, 1998; Raper, S. E. et al., *Human Gene Therapy* 9:671-679, 1998). In addition, deletion of E2b is reported to reduce immune responses (Amalfitano, A. et al., *J. Virol*. 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J*. 11:615-623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

In view of the tissue distribution observed for zcytor17, agonists (including the natural ligand/substrate/cofactor/etc.) and antagonists have enormous potential in both in vitro and in vivo applications. Compounds identified as zcytor17 agonists are useful for stimulating growth of immune and hematopoietic cells in vitro and in vivo. For example, zcytor17 soluble receptors, and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages in culture. Moreover, zcytor17 soluble receptor, agonist, or antagonist may be used in vitro in an assay to measure stimulation of colony formation from isolated primary bone marrow cultures. Such assays are well known in the art.

Antagonists are also useful as research reagents for characterizing sites of ligand-receptor interaction. Inhibitors of zcytor17 activity (zcytor17 antagonists) include anti-zcytor17 antibodies and soluble zcytor17 receptors, as well as other peptidic and non-peptidic agents (including ribozymes).

Zcytor17 can also be used to identify modulators (e.g, antagonists) of its activity. Test compounds are added to the assays disclosed herein to identify compounds that inhibit the activity of zcytor17. In addition to those assays disclosed herein, samples can be tested for inhibition of zcytor17 activity within a variety of assays designed to measure zcytor17 binding, oligomerization, or the stimulation/inhibition of zcytor17-dependent cellular responses. For example, zcytor17-expressing cell lines can be transfected with a reporter gene construct that is responsive to a zcytor17-stimulated cellular pathway. Reporter gene constructs of this type are known in the art, and will generally comprise a zcytor17-DNA response element operably linked to a gene encoding an assay detectable protein, such as luciferase. DNA response elements can include, but are not limited to, cyclic AMP response elements (CRE), hormone response elements (BRE) insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. Candidate compounds, solutions, mixtures or extracts or conditioned media from various cell types are tested for the ability to enhance the activity of zcytor17 receptor as evidenced by a increase in zcytor17 stimulation of reporter gene expression. Assays of this type will detect compounds that directly stimulate zcytor17 signal transduction activity through binding the receptor or by otherwise stimulating part of the signal cascade. As such, there is provided a method of identifying agonists of zcytor17 polypeptide, comprising providing cells responsive to a zcytor17 polypeptide, culturing a first portion of the cells in the absence of a test compound, culturing a second portion of the cells in the presence of a test compound, and detecting a increase in a cellular response of the second portion of the cells as compared to the first portion of the cells. Moreover third cell, containing the reporter gene construct described above, but not expressing zcytor17 receptor, can be used as a control cell to assess non-specific, or non-zcytor17-mediated, stimulation of the reporter. Agonists, including the natural ligand, are therefore useful to stimulate or increase zcytor17 polypeptide function.

A zcytor17 ligand-binding polypeptide, such as the extracellular domain or cytokine binding domain disclosed herein, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument may be advantageously employed (e.g., BIAcore™, Pharmacia Biosensor, Piscataway, N.J.; or SELDI™ technology, Ciphergen, Inc., Palo Alto, Calif.). Such receptor, antibody, member of a complement/anti-complement pair or fragment is immobilized onto the surface of a receptor chip. Use of this instrument is disclosed by Karlsson, *J. Immunol. Methods* 145:229-240, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660-672, 1949) and calorimetric assays (Cunningham et al., *Science* 253:545-48, 1991; Cunningham et al., *Science* 245:821-25, 1991).

Zcytor17 polypeptides can also be used to prepare antibodies that bind to zcytor17 epitopes, peptides or polypeptides. The zcytor17 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zcytor17 polypeptide (e.g., SEQ ID NO:54, SEQ ID NO:57, and the like). Polypeptides comprising a larger portion of a zcytor17 polypeptide, i.e., from 30 to 100 residues up to the entire length of the amino acid sequence are included. Antigens or immunogenic epitopes can also include attached tags, adjuvants and carriers, as described herein. Suitable antigens include the zcytor17 polypeptide encoded by SEQ ID NO:2 from amino acid number 20 (Ala) to amino acid number 732 (Val), or a contiguous 9 to 713, or 30 or 50 to 713 amino acid fragment thereof; and SEQ ID NO:46 from amino acid number 20 (Ala) to amino acid number 649 (Ile), or a contiguous 9 to 630, or 30 or 50 to 630 amino acid fragment thereof; and SEQ ID NO:54 from amino acid number 33 (Ala) to amino acid number 662 (Ile), or a contiguous 9 to 630, or 30 or 50 to 630 amino acid fragment thereof. Preferred peptides to use as antigens are the extracellular domain, cytokine binding domain, fibronectin type III domain, intracellular signaling domain, Box I and Box H sites or other domains and motifs disclosed herein, or a combination thereof; and zcytor17 hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored. Zcytor17 hydrophilic peptides include peptides comprising amino acid sequences selected from the group consisting of: (1) amino acid residues 43 through 48 of SEQ ID NO:2 and SEQ ID NO:46 (residues 56 through 61 of SEQ ID NO:54); (2) amino acid residues 157 through 162 of SEQ ID NO:2 and SEQ ID NO:46 (residues 170 through 175 of SEQ ID NO:54); (3) amino acid residues 158 through 163 of SEQ ID NO:2 and SEQ ID NO:46 (171 through 176 of SEQ ID NO:54); (4) amino acid residues 221 through 226 of SEQ ID NO:2 and SEQ ID NO:46 (234 through 239 of SEQ ID NO:54); and (5) amino acid residues 426 through 431 of SEQ ID NO:2 and SEQ ID NO:46 (residues 439 through 444 of SEQ ID NO:54). In addition, hydrophilic epitopes predicted from a Jameson-Wolf plot Jameson-Wolf plot, e.g., using DNASTAR Protean program (DNASTAR, Inc., Madison, Wis.), are also suitable antigens. In addition, conserved motifs, and variable regions between conserved motifs of zcytor17 are suitable antigens. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zcytor17 polypeptide or a fragment thereof. The immunogenicity of a zcytor17 polypeptide may be increased through the use of an adjuvant, such as alum (aluminum hydroxide) or Freund's complete or incomplete adjuvant. Polypeptides useful for immunization also include fusion polypeptides, such as fusions of zcytor17 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Alternative techniques for generating or selecting antibodies useful herein include in vitro exposure of lymphocytes to zcytor17 protein or peptide, and selection of antibody display libraries in phage or similar vectors (for instance, through use of immobilized or labeled zcytor17 protein or peptide). Genes encoding polypeptides having potential zcytor17 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zcytor17 sequences disclosed herein to identify proteins which bind to zcytor17. These "binding peptides" which interact with zcytor17 polypeptides can be used for tagging cells that express the receptor; for isolating homolog polypeptides by affinity purification; they can be directly or indirectly conjugated to drugs, toxins, radionuclides and the like. These binding peptides can also be used in analytical methods such as for screening expression libraries and neutralizing activity. The binding peptides can also be used for diagnostic assays for determining circulating levels of zcytor17 polypeptides; for detecting or quantitating soluble zcytor17 polypeptides as marker of underlying pathology or disease. These binding peptides can also act as zcytor17 "antagonists" to block zcytor17 binding and signal transduction in vitro and in vivo. These anti-zcytor17 binding peptides would be useful for inhibiting the action of a ligand that binds with zcytor17.

Antibodies are considered to be specifically binding if 1) they exhibit a threshold level of binding activity, and 2) they do not significantly cross-react with related polypeptide molecules. A threshold level of binding is determined if anti-zcytor17 antibodies herein bind to a zcytor17 polypeptide, peptide or epitope with an affinity at least 10-fold greater than the binding affinity to control (non-zcytor17) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-zcytor17 antibodies do not significantly cross-react with related polypeptide molecules is shown, for example, by the antibody detecting zcytor17 polypeptide but not known related polypeptides using a standard Western blot analysis (Ausubel et al., ibid.). Examples of known related polypeptides are those disclosed in the prior art, such as known orthologs, and paralogs, and similar known members of a protein family (e.g., gp130, LIF, WSX-1 and IL12 receptors). Screening can also be done using non-human zcytor17, and zcytor17 mutant polypeptides. Moreover, antibodies can be "screened against" known related polypeptides, to isolate a population that specifically binds to the zcytor17 polypeptides. For example, antibodies raised to zcytor17 are adsorbed to related polypeptides adhered to insoluble matrix; antibodies specific to zcytor17 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), *Academic Press Ltd.,* 1996; Benjamin et al., *Ann. Rev. Immunol.* 2: 67-101, 1984. Specifically binding anti-zcytor17 antibodies can be detected by a number of methods in the art, and disclosed below.

A variety of assays known to those skilled in the art can be utilized to detect antibodies which specifically bind to zcytor17 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zcytor17 protein or polypeptide.

Antibodies to zcytor17 may be used for tagging cells that express zcytor17, such as cells that naturally express zcytor17 such as monocyte and prostate cells, as well as cells that are transformed with zcytor17; for isolating zcytor17 by affinity purification; for diagnostic assays for determining circulating levels of zcytor17 polypeptides; for detecting or quantitating soluble zcytor17 as marker of underlying pathology or disease; in analytical methods employing FACS; for screening expression libraries; for generating anti-idiotypic antibodies; and as neutralizing antibodies or as antagonists to block zcytor17 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zcytor17 or fragments thereof may be used in vitro to detect denatured zcytor17 or fragments thereof in assays, for example, Western Blots or other assays known in the art.

Antibodies to zcytor17 are useful for tagging cells that express the receptor and assaying Zcytor17 expression levels, for affinity purification, within diagnostic assays for determining circulating levels of soluble receptor polypeptides, analytical methods employing fluorescence-activated cell sorting. Divalent antibodies may be used as agonists to mimic the effect of a zcytor17 ligand.

Antibodies herein can also be directly or indirectly conjugated to drugs, toxins, radionuclides and the like, and these conjugates used for in vivo diagnostic or therapeutic applications. For instance, antibodies or binding polypeptides which recognize zcytor17 of the present invention can be used to identify or treat tissues or organs that express a corresponding anti-complementary molecule (i.e., a zcytor17 receptor). More specifically, anti-zcytor17 antibodies, or bioactive fragments or portions thereof, can be coupled to detectable or cytotoxic molecules and delivered to a mammal having cells, tissues or organs that express the zcytor17 molecule.

Suitable detectable molecules may be directly or indirectly attached to polypeptides that bind zcytor17 ("binding polypeptides," including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zcytor17 binding polypeptide-cytokine or antibody-cytokine fusion proteins can be used for enhancing in vivo killing of target tissues (for example, blood, lymphoid, colon, and bone marrow cancers), if the binding polypeptide-cytokine or anti-zcytor17 antibody targets the hyperproliferative cell (See, generally, Hornick et al., *Blood* 89:4437-47, 1997). They described fusion proteins enable targeting of a cytokine to a desired site of action, thereby providing an elevated local concentration of cytokine. Suitable anti-zcytor17 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, zcytor17 binding polypeptide or antibody fusion proteins described herein can be used for enhancing in vivo killing of target tissues by directly stimulating a zcytor17-modulated apoptotic pathway, resulting in cell death of hyperproliferative cells expressing zcytor17.

The bioactive binding polypeptide or antibody conjugates described herein can be delivered orally, intravenously, intraarterially or intraductally, or may be introduced locally at the intended site of action.

Four-helix bundle cytokines that bind to cytokine receptors as well as other proteins produced by activated lymphocytes play an important biological role in cell differentiation, activation, recruitment and homeostasis of cells throughout the body. Therapeutic utility includes treatment of diseases which require immune regulation including autoimmune diseases, such as, rheumatoid arthritis, multiple sclerosis, myasthenia gravis, systemic lupus erythomatosis and diabetes. Zcytor17 receptor antagonists or agonists, including soluble receptors, anti-receptor antibodies, and the natural ligand, may be important in the regulation of inflammation, and therefore would be useful in treating rheumatoid arthritis, asthma, ulcerative colitis, inflammatory bowel disease, Crohn's disease, and sepsis. There may be a role of zcytor17 antagonists or agonists, including soluble receptors, anti-receptor antibodies and the natural ligand, in mediating tumorgenesis, and therefore would be useful in the treatment of cancer. Zcytor17 antagonists or agonists, including soluble receptors, anti-receptor antibodies and the natural ligand, may be a potential therapeutic in suppressing the immune system which would be important for reducing graft rejection or in prevention of graft vs. host disease.

Alternatively, zcytor17 antagonists or agonists, including soluble receptors, anti-zcytor17 receptor antibodies and the natural ligand may activate the immune system which would be important in boosting immunity to infectious diseases, treating immunocompromised patients, such as HIV+ patient, or in improving vaccines. In particular, zcytor17 antagonists or agonists, including soluble receptors and the natural ligand can modulate, stimulate or expand NK cells, or their progenitors, and would provide therapeutic value in treatment of viral infection, and as an anti-neoplastic factor. NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998).

Polynucleotides encoding zcytor17 polypeptides are useful within gene therapy applications where it is desired to increase or inhibit zcytor17 activity. If a mammal has a mutated or absent zcytor17 gene, the zcytor17 gene can be introduced into the cells of the mammal. In one embodiment, a gene encoding a zcytor17 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

In another embodiment, a zcytor17 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Antisense methodology can be used to inhibit zcytor17 gene transcription, such as to inhibit cell proliferation in vivo. Polynucleotides that are complementary to a segment of a zcytor17-encoding polynucleotide (e.g., a polynucleotide as set froth in SEQ ID NO:1, SEQ ID NO:45, SEQ ID NO:53, or SEQ ID NO:57) are designed to bind to zcytor17-encoding mRNA and to inhibit translation of such mRNA. Such antisense polynucleotides are used to inhibit expression of zcytor17 polypeptide-encoding genes in cell culture or in a subject.

In addition, as a cell surface molecule, zcytor17 polypeptides can be used as a target to introduce gene therapy into a cell. This application would be particularly appropriate for introducing therapeutic genes into cells in which zcytor17 is normally expressed, such as lymphoid tissue, bone marrow, prostate, thyroid, monocytes and PBLs, or cancer cells which express zcytor17 polypeptide. For example, viral gene therapy, such as described above, can be targeted to specific cell types in which express a cellular receptor, such as zcytor17 polypeptide, rather than the viral receptor. Antibodies, or other molecules that recognize zcytor17 molecules on the target cell's surface can be used to direct the virus to infect and administer gene therapeutic material to that target cell. See, Woo, S. L. C, *Nature Biotech*. 14:1538, 1996; Wickham, T. J. et al, *Nature Biotech*. 14:1570-1573, 1996; Douglas, J. T et al., *Nature Biotech*. 14:1574-1578, 1996; Rihova, B., *Crit. Rev. Biotechnol*. 17:149-169, 1997; and Vile, R. G. et al., *Mol. Med. Today* 4:84-92, 1998. For example, a bispecific antibody containing a virus-neutralizing Fab fragment coupled to a zcytor17-specific antibody can be used to direct the virus to cells expressing the zcytor17 receptor and allow efficient entry of the virus containing a genetic element into the cells. See, for example, Wickham, T. J., et al., *J. Virol*. 71:7663-7669, 1997; and Wickham, T. J., et al., *J. Virol*. 70:6831-6838, 1996.

Moreover, anti-zcytor17 antibodies and binding fragments can be used for tagging and sorting cells that specifically-express Zcytor17, such as mononuclear cells, lymphoid cells, e.g, non-activated and activated monocyte cells, such as activated CD3+, CD4+ and CD8+ cells, CD19+ B-cells, and other cells, described herein. Such methods of cell tagging and sorting are well known in the art (see, e.g., "Molecular Biology of the Cell", 3$^{rd}$ Ed., Albert, B. et al. (Garland Publishing, London & New York, 1994). One of skill in the art would recognize the importance of separating cell tissue types to study cells, and the use of antibodies to separate specific cell tissue types. Basically, antibodies that bind to the surface of a cell type are coupled to various matrices such as collagen, polysaccharide beads, or plastic to form an affinity surface to which only cells recognized by the antibodies will adhere. The bound cells are then recovered by conventional techniques. Other methods involve separating cells by a fluorescence-activated cell sorter (FACS). In this technique one labels cells with antibodies that are coupled to a fluorescent dye. The labeled cells are then separated from unlabeled cells in a FACS machine. In FACS sorting individual cells traveling in single file pass through a laser beam and the fluorescence of each cell is measured. Slightly further down-stream, tiny droplets, most containing either one or no cells, are formed by a vibrating nozzle. The droplets containing a single cell are automatically give a positive or negative charge at the moment of formation, depending on whether the cell they contain is fluorescent, and then deflected by a strong electric field into an appropriate container. Such machines can select 1 cell in 1000 and sort about 5000 cells each second. This produces a uniform population of cells for cell culture.

One of skill in the art would recognize that the antibodies to the Zcytor17 polypeptides of the present invention are useful, because not all tissue types express the Zcytor17 receptor and because it is important that biologists be able to separate specific cell types for further study and/or therapeutic re-implantation into the body. This is particularly relevant in cells such as immune cells, wherein zcytor17 is expressed.

The present invention also provides reagents that will find use in diagnostic applications. For example, the zcytor17 gene, a probe comprising zcytor17 DNA or RNA or a subsequence thereof can be used to determine if the zcytor17 gene is present on chromosome 5 or if a mutation has occurred. Zcytor17 is located at the 5q11 region of chromosome 5 (See, Example 4). Detectable chromosomal aberrations at the zcytor17 gene locus include, but are not limited to, aneuploidy, gene copy number changes, loss of heterogeneity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, fluorescence in situ hybridization methods, short tandem repeat (STR) analysis employing PCR techniques, and other genetic linkage analysis techniques known in the art (Sambrook et al., ibid.; Ausubel et. al., ibid; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zcytor17 gene is located at the 5q11 region of chromosome 5. Several genes of known function map to this region. For example, a closely related class I cytokine receptor, gp130, also maps chromosome 5q11 suggesting that the 5q11 region is an important region for cytokine receptor expression. Zcytor17 maps in the 5q11 chromosomal region (first region distal of the centromere on the q-arm) and gp130 appears to be about 920.7 kb distal of Zcytor 17. Moreover, the closely related class I cytokine receptor LIFR maps just on the other side of the centromere on the p-arm in the 5p13-p12 region. The gp130 cytokine receptor is shared by several other cytokine receptors to form heterodimeric complexes, that enable signaling by cytokines such as IL-6, leukemia inhibitory factor (LIF), oncostatin M (OSM), and ciliary neurotropic factor (CNTF). Moreover, gp130 may form a heterodimeric, trimeric (e.g., with gp130+ LIF receptor), or multimeric complex with the zcytor17 polypeptide in order to signal. Moreover, as discussed herein, cytokine receptors such as zcytor17 and gp130 play important roles in immune cell function, proliferation, migration, inflammation and the like. As such, zcytor17 polynucleotides, polypeptides, and anti-zcytor17 antibodies serve an important use as a diagnostic to detect defects in the zcytor17 gene or protein, or defects in surrounding chromosomal regions at the 5q11 region of chromosome 5.

Moreover, several disease-related genes cluster in the 5q11 region that are associated with human disorders. One of skill in the art would recognize that a marker in 5q11 such as the zcytor17 polynucleotides of the present invention, would be useful in detecting chromosomal aberrations associated with human disease, since aberrations in and around 5q11 are known to be linked to human disease. For example, 5q11-q13.3 duplications, partial trisomy, and translocations, are associated with multiple anomalies including schizophrenia, a common psychosis. In addition, Maroteaux-Lamy Syndrome, or mucopolysaccaridosis types VI (5q11-q13) and Klippel-Feil syndrome (5q11.2) are associated with translocation at this locus. In addition, these diseases are linked to large chromosomal rearrangements, such as chromosome duplication, translocation or loss of heterogeneity in the 5q11 region chromosome 5. Using, for example, polynucleotides of the present invention in conjunction with known methods in the art described herein, such rearrangements at or around 5q11 can be detected. Moreover, amongst other genetic loci, those for split-hand/foot malformation, type 1 (SHFM1) (5q), Sandhoff disease (5q13), glucocorticoid receptor (5q31), dihydrofolate reductase (DHFR) (5q11.2-13.2) spinal muscular atrophy (5q12.2-q13.3) and Pituitary Hormone Deficiency (5q) all manifest themselves in human disease states as well as map to this region of the human genome. See the Online Mendellian Inheritance of Man (OMIM™, National Center for Biotechnology Information, National Library of Medicine. Bethesda, Md.) gene map, and references therein, for this region of chromosome 5 on a publicly available WWW server (located on the Internet at ncbi.nlm.nih.gov/htbin-post/Omim/getmap?chromosome=5q11 and surrounding loci). All of these serve as possible candidate genes for an inheritable disease that show linkage to the same chromosomal region as the zcytor17 gene.

Similarly, defects in the zcytor17 locus itself may result in a heritable human disease states as discussed herein. One of skill in the art would appreciate that defects in cytokine receptors are known to cause disease states in humans. For example, growth hormone receptor mutation results in dwarfism (Amselem, S et al., *New Eng. J. Med*. 321: 989-995, 1989), IL-2 receptor gamma mutation results in severe combined immunodeficiency (SCID) (Noguchi, M et al., *Cell* 73: 147-157, 1993), c-Mpl mutation results in thrombocytopenia (Mara, K et al., *Proc. Nat. Acad. Sci*. 96: 3132-3136, 1999), and severe mycobacterial and *Salmonella* infections result in interleukin-12 receptor-deficient patients (de Jong, R et al., *Science* 280: 1435-1438, 1998), amongst others. Thus, similarly, defects in zcytor17 can cause a disease state or susceptibility to disease or infection. As the zcytor17 gene is located at the 5q11 region zcytor17, polynucleotide probes can be used to detect chromosome 5q11 loss, trisomy, duplication or translocation associated with human diseases, such as immune cell cancers, bone marrow cancers, prostate cancer, thyroid, parathyroid or other cancers, or immune diseases. Moreover, molecules of the present invention, such as the polypeptides, antagonists, agonists, polynucleotides and antibodies of the present invention would aid in the detection, diagnosis prevention, and treatment associated with a zcytor17 genetic defect.

Molecules of the present invention, such as the polypeptides, antagonists, agonists, polynucleotides and antibodies of the present invention would aid in the detection, diagnosis prevention, and treatment associated with a zcytor17 genetic defect.

A diagnostic could assist physicians in determining the type of disease and appropriate associated therapy, or assistance in genetic counseling. As such, the inventive anti-zcytor17 antibodies, polynucleotides, and polypeptides can be used for the detection of zcytor17 polypeptide, mRNA or anti-zcytor17 antibodies, thus serving as markers and be directly used for detecting or genetic diseases or cancers, as described herein, using methods known in the art and described herein. Further, zcytor17 polynucleotide probes can be used to detect abnormalities or genotypes associated with chromosome 5q11 deletions and translocations associated with human diseases, other translocations involved with malignant progression of tumors or other 5q11 mutations, which are expected to be involved in chromosome rearrangements in malignancy; or in other cancers, or in spontaneous abortion. Similarly, zcytor17 polynucleotide probes can be used to detect abnormalities or genotypes associated with chromosome 5q11 trisomy and chromosome loss associated with human diseases or spontaneous abortion. Thus, zcytor17 polynucleotide probes can be used to detect abnormalities or genotypes associated with these defects.

As discussed above, defects in the zcytor17 gene itself may result in a heritable human disease state. Molecules of the present invention, such as the polypeptides, antagonists, agonists, polynucleotides and antibodies of the present invention would aid in the detection, diagnosis prevention, and treatment associated with a zcytor17 genetic defect. In addition, zcytor17 polynucleotide probes can be used to detect allelic differences between diseased or non-diseased individuals at the zcytor17 chromosomal locus. As such, the zcytor17 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a zcytor17 polynucleotide probe may comprise an entire exon or more. Exons are readily determined by one of skill in the art by comparing zcytor17 sequences (e.g., SEQ ID NO:54) with the human genomic DNA for zcytor17 (Genbank Accession No. AQ002781). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zcytor17 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zcytor17 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zcytor17 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, SEQ ID NO:45 or SEQ ID NO:53, the complement of SEQ ID NO:1, SEQ ID NO:45 or SEQ ID NO:53, or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zcytor17 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.); *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)). Direct analysis of an zcytor17 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the zcytor17 gene, referred to as "transgenic mice," and mice that exhibit a complete absence of zcytor17 gene function, referred to as "knockout mice," may also be generated (Snouwaert et al., *Science* 257: 1083, 1992; Lowell et al., *Nature* 366:740-42, 1993; Capecchi, M. R., *Science* 244: 1288-1292, 1989; Palmiter, R. D. et al. *Annu Rev Genet*. 20: 465-499, 1986). For example, transgenic mice that over-express zcytor17, either ubiquitously or under a tissue-specific or tissue-restricted promoter can be used to ask whether over-expression causes a phenotype. For example, over-expression of a wild-type zcytor17 polypeptide, polypeptide fragment or a mutant thereof may alter normal cellular processes, resulting in a phenotype that identifies a tissue in which zcytor17 expression is functionally relevant and may indicate a therapeutic target for the zcytor17, its agonists or antagonists. For example, a preferred transgenic mouse to engineer is one that expresses a "dominant-negative" phenotype, such as one that over-expresses the zcytor17 polypeptide comprising an extracellular cytokine binding domain with the transmembrane domain attached (approximately amino acids 20 (Ala) to 543 (Leu) of SEQ ID NO:2 and SEQ ID NO:46; or 33 (Ala) to 556 (Leu) of SEQ ID NO:54). Another preferred transgenic mouse is one that over-expresses zcytor17 soluble receptors, such as those disclosed herein. Moreover, such over-expression may result in a phenotype that shows similarity with human diseases. Similarly, knockout zcytor17 mice can be used to determine where zcytor17 is absolutely required in vivo. The phenotype of knockout mice is predictive of the in vivo effects of a zcytor17 antagonist, such as those described herein, may have. The mouse zcytor17 mRNA, cDNA (SEQ ID NO:56 and/or SEQ ID NO:92) and genomic DNA, are used to generate knockout mice. These transgenic and knockout mice may be employed to study the zcytor17 gene and the protein encoded thereby in an in vivo system, and can be used as in vivo models for corresponding human or animal diseases (such as those in commercially viable animal populations). The mouse models of the present invention are particularly relevant as, immune system models, inflammation or tumor models for the study of cancer biology and progression. Such models are useful in the development and efficacy of therapeutic molecules used in human immune diseases, inflammation and cancers. Because increases in zcytor17 expression, as well as decreases in zcytor17 expression are associated with monocytes, monocyte activation, and prostate cells, and may be associated with inflammation and cancers, both transgenic mice and knockout mice would serve as useful animal models for human disease. Moreover, in a preferred embodiment, zcytor17 transgenic mouse can serve as an animal model for specific diseases, particularly those associated with monocytes. Moreover, transgenic mice expression of zcytor17 antisense polynucleotides or ribozymes directed against zcytor17, described herein, can be used analogously to transgenic mice described above.

For pharmaceutical use, the soluble receptor polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a zcytor17 soluble receptor polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zcytor17 soluble receptor polypeptide is an amount sufficient to produce a clinically significant effect.

Polynucleotides and polypeptides of the present invention will additionally find use as educational tools as a laboratory practicum kits for courses related to genetics and molecular biology, protein chemistry and antibody production and analysis. Due to its unique polynucleotide and polypeptide sequence molecules of zcytor17 can be used as standards or as "unknowns" for testing purposes. For example, zcytor17 polynucleotides can be used as an aid, such as, for example, to teach a student how to prepare expression constructs for bacterial, viral, and/or mammalian expression, including fusion constructs, wherein zcytor17 is the gene to be expressed; for determining the restriction endonuclease cleavage sites of the polynucleotides; determining mRNA and DNA localization of zcytor17 polynucleotides in tissues (i.e., by Northern and Southern blotting as well as polymerase chain reaction); and for identifying related polynucleotides and polypeptides by nucleic acid hybridization.

Zcytor17 polypeptides can be used educationally as an aid to teach preparation of antibodies; identifying proteins by Western blotting; protein purification; determining the weight of expressed zcytor17 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., receptor binding, signal transduction, proliferation, and differentiation) in vitro and in vivo. Zcytor17 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the zcytor17 can be given to the student to analyze. Since the amino acid sequence would be known by the professor, the specific protein can be given to the student as a test to determine the skills or develop the skills of the student, the teacher would then know whether or not the student has correctly analyzed the polypeptide. Since every polypeptide is unique, the educational utility of zcytor17 would be unique unto itself.

Moreover, since zcytor17 has a tissue-specific expression and is a polypeptide with a class I cytokine receptor structure and a distinct chromosomal localization, and expression pattern, activity can be measured using proliferation assays; luciferase and binding assays described herein. Moreover, expression of zcytor17 polynucleotides and polypeptides in monocyte, prostate, lymphoid and other tissues can be analyzed in order to train students in the use of diagnostic and tissue-specific identification and methods. Moreover zcytor17 polynucleotides can be used to train students on the use of chromosomal detection and diagnostic methods, since it's locus is known. Moreover, students can be specifically trained and educated about human chromosome 1, and more specifically the locus 5q11 wherein the zcytor17 gene is localized. Such assays are well known in the art, and can be used in an educational setting to teach students about cytokine receptor proteins and examine different properties, such as cellular effects on cells, enzyme kinetics, varying antibody binding affinities, tissue specificity, and the like, between zcytor17 and other cytokine receptor polypeptides in the art.

The antibodies which bind specifically to zcytor17 can be used as a teaching aid to instruct students how to prepare affinity chromatography columns to purify zcytor17, cloning and sequencing the polynucleotide that encodes an antibody and thus as a practicum for teaching a student how to design humanized antibodies. Moreover, antibodies that bind specifically to zcytor17 can be used as a teaching aid for use in detection e.g., of activated monocyte cells, cell sorting, or lymphoid and prostate cancer tissue using histological, and in situ methods amongst others known in the art. The zcytor17 gene, polypeptide or antibody would then be packaged by reagent companies and sold to universities and other educational entities so that the students gain skill in art of molecular biology. Because each gene and protein is unique, each gene and protein creates unique challenges and learning experiences for students in a lab practicum. Such educational kits containing the zcytor17 gene, polypeptide or antibody are considered within the scope of the present invention.

The invention is further illustrated by the following non-limiting examples.

EXAMPLES

Example 1

Identification and Isolation of Full-length Human zcytor17 cDNA

Zcytor18 was identified as a predicted full-length cDNA from human genomic DNA. The sequence of the predicted full length zcytor17 polynucleotide is shown in SEQ ID NO:1 and the corresponding polypeptide is shown in SEQ ID NO:2. To obtain a full-length cDNA from a tissue source, 5' and 3' RACE were employed. Several oligonucleotide primers were designed from the identified genomic sequence AQ002781 (Genbank). The primers were used for priming internally within the genomic sequence to ultimately isolate a full-length cDNA.

A. 5' RACE for zcytor17

A 5' RACE product was generated using an HPVS cDNA library as a template and oligonucleotides ZC12,701 (SEQ ID NO:5) and ZC27,898 (SEQ ID NO:6) as primers. HPVS is an in-house cDNA library generated from a human prostate epithelial cell line (ATCC No. CRL-2221). The PCR reaction used approximately 1 μg of plasmid DNA prepared from the cDNA library as a template, 5 μl of 10×PCR buffer (GIBCO/BRL), 5 μl of 10 mM dNTPs (Perkin Elmer), 20 pmol each oligonucleotide, and 1 μl (5.0 units) Taq polymerase (GIBCO/BRL) in a 50 ul reaction volume. This first-round 5' RACE PCR reaction was run as follows: 30 cycles at 94° C. for 1 minute, 65° C. for 1 minute, 72° C. for 2 minutes, then 72° C. for 7 minutes; 4° C. soak. An aliquot of 5' RACE PCR product was removed and analyzed on a 1.0% agarose gel. Multiple bands were seen on the gel.

The remaining 5' RACE PCR product was ethanol precipitated and diluted 1:50. A second-round nested 5' RACE PCR reaction was run to amplify template cDNA sequence. This PCR reaction used oligonucleotides ZC14,063 (SEQ ID NO:7) and ZC27,899 (SEQ ID NO:8), which were designed to anneal to sequence internal of ZC12,701 (SEQ ID NO:5) and ZC27,898 (SEQ ID NO:6). This nested PCR reaction was run as per the first-round 5' RACE reaction disclosed above. The resulting DNA products were electrophoresed on a 1.0% agarose gel and a prominent band at approximately 900 bp was seen. The DNA band was gel purified and sequenced using standard methods. Sequence analyses revealed that the DNA product included part of the genomic AQ002781 DNA sequence (Genbank) and appeared to extend the cDNA sequence for zcytor17 on the 5' end to include a translation initiating methionine residue and some 5' untranslated sequence. The polynucleotide sequence of the 5' RACE product is shown in SEQ ID NO:9.

B. 3' RACE for zcytor17

Primers for 3' RACE were designed using the 5' RACE product (SEQ ID NO:9) obtained above. A 3' RACE product was generated using a human prostate in-house cDNA library as a template and oligonucleotides ZC28,481 (SEQ ID NO:10) and ZC6,346 (SEQ ID NO:11) as primers. This first-round 3' RACE PCR reaction was run under the conditions described in Example 1A. An aliquot of 3' RACE PCR product was removed and analyzed on a 1.0% agarose gel. Multiple bands were seen on the gel.

The remaining 3' RACE PCR product was ethanol precipitated and diluted 1:40. A second-round nested 3' RACE PCR reaction was run to amplify template cDNA sequence. This PCR reaction used oligonucleotides ZC28,480 (SEQ ID NO:12) and ZC26,405 (SEQ ID NO:13), which were designed to anneal to sequence internal of ZC28,481 (SEQ ID NO:10) and ZC6,346 (SEQ ID NO:11). This nested PCR reaction was run as disclosed above. The resulting DNA products were electrophoresed on a 1.0% agarose gel and a prominent band at approximately 2100 bp was seen.

The remaining DNA was ethanol precipitated and diluted 1:40. A third-round nested 3' RACE PCR reaction was run to amplify template cDNA sequence. This PCR reaction used oligonucleotides ZC27,895 (SEQ ID NO:14) and ZC5,020 (SEQ ID NO:15), which were designed to anneal to sequence internal of ZC28,480 (SEQ ID NO:12) and ZC26,405 (SEQ ID NO:13). This nested PCR reaction was run as disclosed above. The resulting PCR products were electrophoresed on a 1.0% agarose gel and a prominent band at approximately 2000 bp was seen. The DNA band was gel purified and sequenced. Sequence analyses revealed that the DNA product included part of the 5' RACE product (SEQ ID NO:9) and appeared to extend the cDNA sequence for zcytor17 on the 3' end to include a translation stop codon and some 3' untranslated sequence. The polynucleotide sequence of the 3' RACE product is shown in SEQ ID NO:16. The polynucleotide sequence of the zcytor17 is shown in SEQ ID NO:45 and the corresponding polypeptide sequence is shown in SEQ ID NO:46.

C. A Second 5' Race for zcytor17 Identified an Alternative Full-length zcytor17

A 5' RACE product was generated using a WI-38 cDNA library as a template and oligonucleotides ZC12,701 (SEQ ID NO:5) and ZC27,899 (SEQ ID NO:8) as primers. WI-28 is an in-house cDNA library generated from a human embryonic lung cell line (ATCC No. CRL-75). The PCR reaction used approximately 1 μg of plasmid DNA prepared from the cDNA library as a template, 5 μl of 10×PCR buffer (GIBCO/BRL), 5 μl of 10 mM dNTPs (Perkin Elmer), 20 pmol each oligonucleotide, and 1 (5.0 units) Taq polymerase (GIBCO/BRL) in a 50 μl reaction volume. This first-round 5' RACE PCR reaction was run as follows: 30 cycles at 94° C. for 1 minute, 65° C. for 1 minute, 72° C. for 2 minutes, then 72° C. for 7 minutes; 4° C. soak. An aliquot of 5' RACE PCR product was removed and analyzed on a 1.0% agarose gel. Multiple bands were seen on the gel.

The remaining DNA was ethanol precipitated and diluted 1:50. A second-round nested 5' RACE PCR reaction was run to amplify template cDNA sequence. This PCR reaction used oligonucleotides ZC14,063 (SEQ ID NO:25), and ZC27,900 (SEQ ID NO:51), which were designed to anneal to sequence internal of ZC12,701 (SEQ ID NO:5) and ZC27,899 (SEQ ID NO:8). This nested PCR reaction was run as per the first-round 5' RACE reaction disclosed above. The resulting DNA products were electrophoresed on a 1.0% agarose gel and a prominent band at approximately 1200 bp was seen. The DNA band was gel purified and sequenced. Sequence analyses revealed that the DNA product included part of the genomic DNA sequence AQ002781 (Genbank) and appeared to extend the cDNA sequence for zcytor17 on the 5' end to include a translation initiating methionine residue and some 5' untranslated sequence. DNA sequencing showed that the polypeptide generated from translation from this alternative initiating methionine (shown in SEQ ID NO:53 at nucleotide 497) generates a second full-length form of zcytor17 that differs by an additional 13 amino acids in-frame at the N-terminus (MKLSPQPSCVNLG; SEQ ID NO:52) from that shown in SEQ ID NO:46. The polynucleotide sequence of the second full-length form of zcytor17 is shown in SEQ ID NO:53 and the corresponding polypeptide sequence is shown in SEQ ID NO:54. The second full-length form of zcytor17 (SEQ ID NO:53 and SEQ ID NO:54) is likely the most commonly expressed form.

Example 2

Identification and Isolation of Truncated Forms Human zcytor17 cDNA

A. Isolation of a cDNA Coding for a Variant Form of zcytor17 Truncated at the Fibronectin Domain A 3' RACE product for a truncated soluble form of zcytor17 was generated using a protocol identical to that described above for 3' RACE (Example 1B), except that the starting material was the HPVS cDNA library. HPVS is an in-house cDNA library generated from a human prostate epithelial cell line (ATCC No. CRL-2221). The resulting products from the third round nested 3' RACE were electrophoresed on a 1.0% agarose gel and a prominent band at approximately 700 bp was seen. The DNA band was gel purified and sequenced. Sequence analyses revealed that the DNA product included part of the 5' RACE product (SEQ ID NO:9) and appeared to extend the cDNA sequence for zcytor17 to include a translation stop codon near the end of the cytokine-binding domain. This could represent an expressed soluble form of the receptor truncated within the fibronectin domain. The polynucleotide sequence of the soluble form of zcytor17 truncated within the fibronectin domain is shown in SEQ ID NO:15 and the corresponding polypeptide sequence is shown in SEQ ID NO:18.

B. Isolation of a cDNA Coding for a Form of zcytor17 Truncated at the End of the Cytokine-binding Domain A 3'RACE product for a truncated form of zcytor17 was generated using the HPVS cDNA library as a template and ZC27,895 (SEQ ID NO:14) and ZC6,346 (SEQ ID NO:11) as primers. This first-round 3' RACE PCR reaction was run as follows: 30 cycles at 94° C. for 1 minute, 65° C. for 1 minute, 72° C. for 2 minutes, then 72° C. for 7 minutes; 4° C. soak. An aliquot of 3' RACE PCR product was removed and analyzed on a 1.0% agarose gel. Multiple bands were seen on the gel.

The remaining DNA was ethanol precipitated and diluted 1:40. A second-round nested 3' RACE PCR reaction was run to amplify template cDNA sequence. This PCR reaction used oligonucleotides ZC27,897 (SEQ ID NO:19) and ZC5,020 (SEQ ID NO:15), which were designed to anneal to sequence internal of ZC27,895 (SEQ ID NO:14) and ZC6,346 (SEQ ID NO:11). This nested PCR reaction was run as per the first-round 5' RACE disclosed in Example 1A, above. The resulting DNA products were electrophoresed on a 1.0% agarose gel and a prominent band at approximately 1100 bp was seen. The DNA band was gel purified and sequenced. Sequence analysis revealed that the DNA product included part of the genomic AQ002781 DNA sequence (Genbank) and appeared to extend the cDNA sequence for zcytor17 on the 3' end to include a translation stop codon at the end of the cytokine-binding domain.

To confirm that the above sequence did indeed overlap with the genomic AQ002781 DNA sequence, an additional PCR reaction was performed. A PCR product was generated using the HPVS cDNA library as a template and oligonucleotides ZC28,481 (SEQ ID NO:10) and ZC28,521 (SEQ ID NO:20) as primers. The PCR reaction was run as follows: 30 cycles at 94° C. for 1 minute, 65° C. for 1 minute, 72° C. for 2 minutes, then 72° C. for 7 minutes; 4° C. soak. The resulting DNA products were electrophoresed on a 1.0% agarose gel and a prominent band at approximately 800 bp was seen. The DNA band was gel purified and sequenced. Sequence analyses confirmed that this was a truncated form of zcytor17. This could represent an expressed soluble form of the receptor truncated near the end of the cytokine-binding domain. The polynucleotide sequence of this soluble form of zcytor17 is shown in SEQ ID NO:21 and the corresponding polypeptide sequence is shown in SEQ ID NO:22).

Another truncated 3' RACE product was isolated using the protocol described above for isolation of a cDNA variant truncated at the fibronectin domain (Example 2A). Sequencing of the isolated PCR product verified the sequence of the soluble form of zcytor17 as shown in SEQ ID NO:21.

Example 3

Tissue Distribution of Human zcytor17 in Tissue Panels Using Northern Blot and PCR A. Human zcytor17 Tissue Distribution Using Northern Blot Human Multiple Tissue Northern Blots (Human 12-lane MTN Blot I and II, and Human Immune System MTN Blot II; Human Endocrine MTN, Human Fetal MTN Blot II, Human Multiple Tissue Array) (Clontech) as well as in house blots containing various tissues were probed to determine the tissue distribution of human zcytor17 expression. The in-house prepared blots included the following tissue and cell line mRNA: SK-Hep-1 cells, THP1 cells, Adrenal gland (Clontech); Kidney (Clontech), Liver (Clontech and Invitrogen); Spinal cord (Clontech), Testis (Clontech), Human CD4+ T-cells, Human CD8+ T-cells, Human CD19+ T-cells, human mixed lymphocyte reaction (MLR), THP1 cell line (ATCC No. TIB-202), U937 cell line, p388D1 mouse lymphoblast cell line (ATCC No. CCL-46) with or without stimulation by Ionomycin; and WI-38 human embryonic lung cell line (ATCC No. CRL-2221) with or without stimulation by Ionomycin.

An approximately 500 bp PCR derived probe was amplified using the 5' RACE (Example 1A) (SEQ ID NO:9) as template and oligonucleotides ZC28,575 (SEQ ID NO:23) and ZC27,899 (SEQ ID NO:24) as primers. The PCR amplification was carried out as follows: 30 cycles of 94° C. for 1 minute, 65° C. for 1 minute, and 72° C. for 1 minute; followed by I cycle at 72° C. for 7 minutes. The PCR product was visualized by agarose gel electrophoresis and the approximately 500 bp PCR product was gel purified as described herein. The probe was radioactively labeled using the PRIME IT II™ Random Primer Labeling Kit (Stratagene) according to the manufacturer's instructions. The probe was purified using a NUCTRAP™ push column (Stratagene). EXPRESSHYB™ (Clontech) solution was used for the prehybridization and as a hybridizing solution for the Northern blots. Prehybridization was carried out at 68° C. for 2 hours. Hybridization took place overnight at 68° C. with about 1.5×$10^6$ cpm/ml of labeled probe. The blots were washed three times at room temperature in 2×SSC, 0.05% SDS, followed by 1 wash for 10 minutes in 2×SSC, 0.1% SDS at 50° C. Several faint bands were seen after several days exposure. An approximately 9 kb transcript was seen in trachea, skeletal muscle and thymus; an approximately 2 kb transcript was seen in PBL, HPV, U937 and THP-1 cells; and about a 1.2 kb transcript was seen in placenta, bone marrow and thyroid, and HPV and U937 cells. In all the tissues listed above, the signal intensity was faint. There appeared to be little expression in most normal tissues, suggesting that zcytor17 expression may be dependent on activation of the cell or tissues in which it is expressed.

Northern analysis is also performed using Human Cancer Cell Line MTN™ (Clontech). PCR and probing conditions are as described above. A strong signal in a cancer line suggests that zcytor17 expression may be expressed in activated cells and/or may indicate a cancerous disease state. Moreover, using methods known in the art, Northern blots or PCR analysis of activated lymphocyte cells can also show whether zcytor17 is expressed in activated immune cells.

B. Tissue Distribution in Tissue Panels Using PCR

A panel of cDNAs from human tissues was screened for zcytor17 expression using PCR. The panel was made in-house and contained 94 marathon cDNA and cDNA samples from various normal and cancerous human tissues and cell lines is shown in Table 5, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:49) and ZC21196 (SEQ ID NO:50) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:25) and 3' alpha tubulin specific oligo primer ZC17,574 (SEQ ID NO:26) or 3' G3PDH specific oligo primer ZC17,600 (SEQ ID NO:27); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2-100 pg/μl of cDNA. The PCR reactions were set up using oligos ZC26,358 (SEQ ID NO:28) and ZC26,359 (SEQ ID NO:29), TaKaRa Ex Taq (TAKARA Shuzo Co LTD, Biomedicals Group, Japan), and Rediload dye (Research Genetics, Inc., Huntsville, Ala.). The amplification was carried out as follows: 1 cycle at 94° C. for 2 minutes, 35 cycles of 94° C. for 30 seconds, 66.3° C. for 30 seconds and 72° C. for 30 seconds, followed by 1 cycle at 72° C. for 5 minutes. About 10 μl of the PCR reaction product was subjected to standard Agarose gel electrophoresis using a 4% agarose gel. The correct predicted DNA fragment size was observed in lymph node, prostate, thyroid, HPV (prostate epithelia), HPVS (prostate epithelia, selected), lung tumor, uterus tumor reactions, along with the genomic DNA reaction. One of the primers can anneal to genomic or to the zcytor17 short-form soluble receptor (SEQ ID NO:21), suggesting that the expression pattern seen may be that of this alternative form of zcytor17.

The DNA fragment for prostate tissue (2 samples), HPV (prostate epithelia), HPVS (prostate epithelia, selected), and genomic were excised and purified using a Gel Extraction Kit (Qiagen, Chatsworth, Calif.) according to manufacturer's instructions. Fragments were confirmed by sequencing to show that they were indeed zcytor17.

TABLE 5

| Tissue/Cell line | # samples |
|---|---|
| Adrenal gland | 1 |
| Bladder | 1 |
| Bone Marrow | 1 |
| Brain | 1 |
| Cervix | 1 |
| Colon | 1 |
| Fetal brain | 1 |
| Fetal heart | 1 |
| Fetal kidney | 1 |
| Fetal liver | 1 |
| Fetal lung | 1 |
| Fetal muscle | 1 |
| Fetal skin | 1 |
| Heart | 2 |
| K562 (ATCC # CCL-243) | 1 |
| Kidney | 1 |
| Liver | 1 |
| Lung | 1 |
| Lymph node | 1 |
| Melanoma | 1 |
| Pancreas | 1 |
| Pituitary | 1 |

TABLE 5-continued

| Tissue/Cell line | # samples |
|---|---|
| Placenta | 1 |
| Prostate | 1 |
| Rectum | 1 |
| Salivary Gland | 1 |
| Skeletal muscle | 1 |
| Small intestine | 1 |
| Spinal cord | 1 |
| Spleen | 1 |
| Stomach | 1 |
| Testis | 2 |
| Thymus | 1 |
| Thyroid | 1 |
| Trachea | 1 |
| Uterus | 1 |
| Esophagus tumor | 1 |
| Gastric tumor | 1 |
| Kidney tumor | 1 |
| Liver tumor | 1 |
| Lung tumor | 1 |
| Ovarian tumor | 1 |
| Rectal tumor | 1 |
| Uterus tumor | 1 |
| Bone marrow | 3 |
| Fetal brain | 3 |
| Islet | 2 |
| Prostate | 3 |
| RPMI #1788 (ATCC # CCL-156) | 2 |
| Testis | 4 |
| Thyroid | 2 |
| WI38 (ATCC # CCL-75 | 2 |
| ARIP (ATCC # CRL-1674-rat) | 1 |
| HaCat-human keratinocytes | 1 |
| HPV (ATCC # CRL-2221) | 1 |
| Adrenal gland | 1 |
| Prostate SM | 2 |
| CD3+ selected PBMC's Ionomycin + PMA stimulated | 1 |
| HPVS (ATCC # CRL-2221) - selected | 1 |
| Heart | 1 |
| Pituitary | 1 |
| Placenta | 2 |
| Salivary gland | 1 |
| HL60 (ATCC # CCL-240) | 3 |
| Platelet | 1 |
| HBL-100 | 1 |
| Renal mesangial | 1 |
| T-cell | 1 |
| Neutrophil | 1 |
| MPC | 1 |
| Hut-102 (ATCC # TIB-162) | 1 |
| Endothelial | 1 |
| HepG2 (ATCC # HB-8065) | 1 |
| Fibroblast | 1 |
| E. Histo | 1 |

B. Expression Analysis of zcytoR17 by PCR and Northern

Annotation of the cell types and growth conditions that affect expression of the receptor is a useful means of elucidating its function and predicting a source of ligand. To that end we surveyed a wide variety of tissue and cell types by PCR. The thermostable polymerase Advantage II™ (Clontech, La Jolla, Calif.) was used with the oligonucleotide primers ZC29,180 (SEQ ID NO:73) and ZC29,179 (SEQ ID NO:74) and 1-10 ng of the various cDNA templates listed below for 30 amplification cycles of (94° C., 30 sec.; 66° C., 20 sec.; 68° C., 1 min. 30 sec.). Following this, 20% of each reaction was run out on 0.8% agarose, TAE/ethidium bromide gels and visualized with UV light. Samples were then scored on the basis of band intensity. See Table 6 below.

TABLE 6

| Cells and Conditions | Score 0-5 |
|---|---|
| Hel stimulated with PMA | 0 |
| U937 | 3 |
| MCF-7 | 0 |
| HuH7 | 1 |
| Human follicle | 0 |
| HT-29 | 0 |
| HEPG2 | 0 |
| HepG2 stimulated with IL6 | 0 |
| Human dermal endothelial | 0 |
| Human venous endothelial | 0 |
| Human CD4+ | 0 |
| BEWO | 0 |
| Human CD19+ | 1 |
| Human PBMC stimulated with PHA, PMA, Ionomycin, IL2, IL4, TNFα 24 hours | 0 |
| Human PBMC stimulated with LPS, PWM, IFNγ, TNFα, 24 hours | 0 |
| Human PBMC all of the above conditions for 48 hours | 4 |
| HUVEC p.2 | 4 |
| RPMI1788 | 0 |
| TF1 | 0 |
| Monkey spleen T cells stimulated with PMA, Ionomycin | 0 |
| Human prostate epithelia HPV transformed | 5 |
| Human tonsils, inflamed | 0 |
| HACAT | 0 |
| Human chondrocyte | 1 |
| Human synoviacyte | 1 |
| THP1 | 5 |
| REH | 0 |

Of the strong positive PCR signals, two were from the human monocyte cell lines U937 and THP1.

These two cell lines along with a prostate epithelia line were selected for further analysis by Northern blot. Previous attempts at visualizing a transcript by northern analysis using mRNA from various tissues yielded weak and diffuse signals in the surprisingly large size range of 7-10 kb making this data difficult to interpret. A denaturing formaldehyde/MOPS/0.8% agarose gel was prepared (RNA Methodologies, Farrell, RE Academic Press) and 2 μg of polyA+ mRNA was run for each sample along side an RNA ladder (Life Technologies, Bethesda, Md.). The gel was then transferred to Hybond nylon (Amersham, Buckinghamshire, UK), UV crosslinked, and hybridized in ExpressHyb solution (Clontech, LaJolla, Calif.) at 68° C. overnight using a probe to human zcytoR17 generated by PCR with the oligos ZC28,575 (SEQ ID NO:23), and ZC27,899 (SEQ ID NO:24) and labeled with a Megaprime $^{32}$P kit (Amersham). The northern blot was subsequently washed with 0.2×SSC+0.1% SDS at 65 C for 15 minutes and exposed to film for 7 days with intensifying screens. A prominent 8 kb band was seen in both the prostate epithelia and U937 lanes while a fainter band was present in the THP1 lane.

To optimize the cDNA used as a hybridization probe, four different regions of the full-length human zcytoR17 sequence were amplified by PCR, labeled and hybridized as described above to southern blots containing genomic and amplified cDNA library DNA. The four probes, herein designated probes A-D, were amplified using the following primer pairs: (A) ZC28,575 (SEQ ID NO:23), ZC27,899 (SEQ ID NO:24); (B) ZC27,895 (SEQ ID NO:64), ZC28,917 (SEQ ID NO:73); (C) ZC28,916 (SEQ ID NO:75), ZC28,918 (SEQ ID NO:76); and (D) ZC28,916 (SEQ ID NO:75), ZC29,122 (SEQ ID NO:65). Human genomic DNA along with amplified cDNA libraries demonstrated to contain zcytor17 by PCR were digested with EcoR1 and Xho1 to liberate inserts and run out on duplicate TAE/0.8% agarose gels, denatured with 0.5M NaOH, 1.5 M NaCl, blotted to Hybond, UV crosslinked and each hybridized with a distinct probe. Probe B was found to have the least nonspecific binding and strongest signal. Thus, Probe B was used for all subsequent hybridizations.

Given that the THP1 cells are an excellent model of circulating monocytes and expressed zcytor17 at low levels we treated them with a variety of compounds in an effort to increase expression of zcytoR17. The cells were grown to a density of 2e5/ml, washed and resuspended in various stimulating media, grown for four or thirty hours, and harvested for RNA preparations. Each media was supplemented with one of the following drugs or pairs of cytokines: LPS 2 ug/ml (Sigma Chemicals, StLouis Mo.), hTNFα 2 ng/ml (R&D Systems, Minneapolis, Minn.), hGMCSF 2 ng/ml (R&D Systems, Minneapolis, Minn.), hIFNγ 50 ng/ml (R&D Systems, Minneapolis, Minn.), hMCSF 1 ng/ml (R&D Systems, Minneapolis, Minn.), hIL6 1 ng/ml (R&D Systems, Minneapolis, Minn.), hIL1β 2 ng/ml (R&D Systems, Minneapolis, Minn.), hIFNγ 50 ng/ml+hIL4 0.5 ng/ml (R&D Systems, Minneapolis, Minn.), hIFNγ 50 ng/ml+hIL10 1 ng/ml (R&D Systems, Minneapolis, Minn.), PMA 10 ng/ml (Calbiochem, SanDiego, Calif.) and an untreated control. At the end of the culture period Total RNA was prepared using an RNAeasy Midi-kit (Qiagen, Valencia, Calif.). Poly A+ RNA was selected from the total RNA using an MPG kit (CPG, Lincoln Park, N.J.). 2 ug of polyA+ RNA from each condition was run on formaldehyde/MOPS/agarose gels, transferred to nylon and LV crosslinked as described above. These northern blots were then hybridized, as above, to probe B at 68° C. overnight, washed at high stringency with 0.2×SSC, 0.1% SDS at 65 C, exposed to film overnight then exposed to phosphor screens for signal quantitation (see FIG. 2). A dominant 8 kb mRNA as well a relatively weaker 2.8 kb band were seen in all lanes. A 20-fold increase in zcytor17 mRNA was seen in RNA from cells treated with hIFNγ for 30 hours, this effect was slightly muted with simultaneous treatment with IL4. Minor 3 fold increases in mRNA were seen in RNA from cells treated with LPS, TNFα and GM-CSF while MCSF, IL6, and IL1β had no effect on zcytor17 mRNA levels. Taken together this data suggests a role for the zcytor17 receptor and its ligand in monocyte macrophage biology and by extension any number of disease processes in which these cell participate.

Example 4

PCR-Based Chromosomal Mapping of the zcytor17 Gene

Zcytor17 was mapped to chromosome 5 using the commercially available "GeneBridge 4 Radiation Hybrid (RH) Mapping Panel"(Research Genetics, Inc., Huntsville, Ala.). The GeneBridge 4 RH panel contains DNA from each of 93 radiation hybrid clones, plus two control DNAs (the HFL donor and the A23 recipient). A publicly available WWW server located on the Internet at genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 RH panel.

For the mapping of Zcytor17 with the GeneBridge 4 RH panel, 20 μreactions were set up in a 96-well microtiter plate compatible for PCR (Stratagene, La Jolla, Calif.) and used in a "RoboCycler Gradient 96" thermal cycler (Stratagene). Each of the 95 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC27,895 (SEQ ID NO:14), 1 μl antisense primer, ZC27,899 (SEQ ID NO:24), 2 μl "RediLoad" (Research Genetics, Inc., Huntsville, Ala.), 0.4 μl 50× Advantage KlenTaq Polymerase Mix (Clontech Laboratories, Inc.), 25 ng of DNA from an individual hybrid clone or control and distilled water for a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 54° C. and 1 minute AND 15 seconds extension at 72° C., followed by a final I cycle extension of 7 minutes at 72° C. The reactions were separated by electrophoresis on a 2% agarose gel (EM Science, Gibbstown, N.J.) and visualized by staining with ethidium bromide.

The results showed that Zcytor17 maps 6.72 cR_3000 distal from the framework marker AFM183YB8 on the chromosome 5 WICGR radiation hybrid map. The use of surrounding genes/markers positions Zcytor17 in the 5q11 chromosomal region.

Example 5

Construction of MPL-zcytor17 Polypeptide Chimera: MPL Extracellular and TM Domain Fused to the zcytor17 Intracellular Signaling Domain The 5' extracellular domain of the murine MPL receptor was isolated from a plasmid containing the murine MPL receptor (PHZ1/MPL plasmid) by digestion with EcoRI and BamHI generating a 1164 bp fragment. The digestion was run on a 1% agarose gel and the fragment was isolated using the Qiaquick gel extraction kit (Qiagen) as per manufacturer's instructions. The rest of the MPL extracellular domain and transmembrane domain were generated using PCR with primers ZC6,673 (SEQ ID NO:58) and ZC29,082 (SEQ ID NO:59). The reaction conditions were as follows: 15 cycles at 94° C. for 1 min., 55° C. for 1 min., 72° C. for 2 min.; followed by 72° C. for 7 min.; then a 4° C. soak. The PCR product was run on a 1% agarose gel and the approximately 400 bp MPL receptor fragment was isolated using Qiaquick™ gel extraction kit (Qiagen) as per manufacturer's instructions.

The intracellular domain of human zcytor17 was isolated from a plasmid containing zcytor17 receptor cDNA (#23/pCAP) using PCR with primers ZC29,083 (SEQ ID NO:60) and ZC29,145 (SEQ ID NO:61). The polynucleotide sequence corresponds to the zcytor17 receptor coding sequence is shown in SEQ ID NO:54. The reaction conditions were as per above. The PCR product was run on a 1% agarose gel and the approximately 320 bp zcytor17 fragment isolated using Qiaquick gel extraction kit as per manufacturer's instructions.

Each of the isolated PCR fragments described above were mixed at a 1:1 volumetric ratio and used in a PCR reaction using ZC6673 (SEQ ID NO:58) and ZC29145 (SEQ ID NO:61) to create all but the 5' MPL portion of the MPL-zcytor17 chimera. The reaction conditions were as follows: 15 cycles at 94° C. for 1 min., 55° C. for 1 min., 72° C. for 2 min.; followed by 72° C. for 7 min; then a 4° C. soak. The entire PCR product was run on a 1% agarose gel and the approximately 700 bp MPL-zcytor17 chimera fragment isolated using Qiaquick gel extraction kit (Qiagen) as per manufacturer's instructions. The MPL-zcytor17 chimera fragment was digested with BamHI (BRL) and XbaI (Boerhinger Mannheim) as per manufacturer's instructions. The entire digest was run on a 1% agarose gel and the cleaved MPL-zcytor17 chimera isolated using Qiaquick™ gel extraction kit (Qiagen) as per manufacturer's instructions. The resultant cleaved MPL-zcytor17 chimera plus 5' MPL EcoRI/BamHI fragment described above were inserted into an expression vector to generate the full MPL-zcytor17 chimeric receptor as described below.

Recipient expression vector pZP-7 was digested with EcoRI (BRL) and XbaI (BRL) as per manufacturer's instructions, and gel purified as described above. This vector fragment was combined with the EcoRI and XbaI cleaved MPL-zcytor17 PCR chimera isolated above and the EcoRI and BamHI 5' MPL fragment isolated above in a ligation reaction. The ligation was run using T4 Ligase (Epicentre Technologies), at room temperature for 1 hour as per manufacturer's instructions. A sample of the ligation was electroporated into DH10B ElectroMAX™ electrocompetent *E. coli* cells (25 μF, 200Ω, 1.8V). Transformants were plated on LB+Ampicillin plates and single colonies screened by miniprep (Qiagen) and digestion with EcoRI to check for the MPL-zcytor17 chimera. EcoRI digestion of correct clones yield about a 2 kb fragment. Confirmation of the MPL-zcytor17 chimera sequence was made by sequence analyses. The insert was approximately 3.1 kb, and was full-length.

Example 6

MPL-zcytor17 Chimera Based Proliferation in BAF3 Assay Using Alamar Blue

A. Construction of BaF3 Cells Expressing MPL-zcytor17 Chimera

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol*. 6: 4133-4135, 1986), was maintained in complete media (RPMI medium (JRH Bioscience Inc., Lenexa, Kans.) supplemented with 10% heat-inactivated fetal calf serum, 1 ng/ml murine (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-7/MPL-zcytor17 plasmid DNA (Example 5) was prepared and purified using a Qiagen Maxi Prep kit (Qiagen) as per manufacturer's instructions. BaF3 cells for electroporation were washed twice in RPMI media and then resuspended in RPMI media at a cell density of $10^7$ cells/ml. One ml of resuspended BaF3 cells was mixed with 30 μg of the pZP-7/MPL-zcytor17 plasmid DNA and transferred to separate disposable electroporation chambers (GIBCO BRL). At room temperature cells were given 5×0.1 msec shocks at 800 volts followed by 5×2 ms shocks at 600 volts delivered by an electroporation apparatus (Cyto-Pulse). The electroporated cells were transferred to 50 ml of complete media and placed in an incubator for 15-24 hours (37° C., 5% $CO_2$). Then Geneticin™ (Gibco) selection (1 mg/ml G418) was added to the cells in a T-162 flask to isolate the G418-resistant pool. Pools of the transfected BaF3 cells, hereinafter called BaF3/MPL-zcytor17 cells, were assayed for signaling capability as described below.

B. Testing the Signaling Capability of the BaF3/MPL-Zcytor17 Cells Using an Alamar Blue Proliferation Assay BaF3/MPL-zcytor17 cells were spun down and washed in the complete media, described above, but without mIL-3 (hereinafter referred to as "mIL-3 free media"). The cells were spun and washed 3 times to ensure the removal of the mIL-3 Cells were then counted in a hemacytometer. Cells were plated in a 96-well format at 5000 cells per well in a volume of 100 μl per well using the mIL-3 free media.

Proliferation of the BaF3/MPL-zcytor17 cells was assessed using murine thrombopoietin (mTPO) diluted with mIL-3 free media to 200 ng/ml, 100 ng/ml, 50 ng/ml, 25 ng/ml, 12.5 ng/ml, 6.25 ng/ml, 3.1 mg/ml, 1.5 ng/ml concentrations. 100 μl of the diluted mTPO was added to the BaF3/MPL-zcytor17 cells. The total assay volume is 200 μl. Negative controls were run in parallel using mIL-3 free media only, without the addition of mTPO. The assay plates were incubated at 37° C., 5% $CO_2$ for 3 days at which time Alamar Blue (Accumed, Chicago, Ill.) was added at 20 μl/well. Alamar Blue gives a fluorometric readout based on the metabolic activity of cells, and is thus a direct measurement of cell proliferation in comparison to a negative control. Plates were again incubated at 37° C., 5% $CO_2$ for 24 hours. Plates were read on the Finax™ plate reader (Molecular Devices Sunnyvale, Calif.) using the SoftMax™ Pro program, at wavelengths 544 (Excitation) and 590 (Emission).

Results confirmed the signaling capability of the intracellular portion of the zcytor17 receptor, as the thrombopoietin induced proliferation at approximately 9-13 fold over background at mTPO concentrations of 50 ng/ml and greater.

Example 7

Construction of Zcytor17-mpl Polypeptide Chimera: Zcytor17 Extracellular Domain Fused to the Mpl Intracellular Signaling Domain and TM Domain The extracellular domains of the zcytor17 receptor are isolated from a plasmid containing the zcytor17 receptor using PCR with primers designed to amplify the extracellular domain or portion thereof of zcytor17 shown in SEQ ID NO:1, SEQ ID NO:45, SEQ ID NO:17 or SEQ ID NO:21 or corresponding region of SEQ ID NO:53 or SEQ ID NO:56. Preferred reaction conditions are as follows: 95° C. for 1 min.; 35 cycles at 95° C. for 1 min., 45° C. for 1 min., 72° C. for 2 min.; followed by 72° C. at 10 min.; then a 10° C. soak. The PCR product is run on a 1% low melting point agarose (Boerhinger Mannheim, Indianapolis, Ind.) and the zcytor17 receptor fragment isolated using Qiaquick™ gel extraction kit (Qiagen) as per manufacturer's instructions.

The intracellular and transmembrane domains of MPL are isolated from a plasmid containing MPL receptor cDNA (PHZ1/MPL plasmid) (Example 5) using PCR with primers spanning the 3' end of the zcytor17 extracellular domain and the 5' end of the MPL intracellular and transmembrane domains and ZC17,206 (SEQ ID NO:33). Preferred reaction conditions are run as per above. The PCR product is run on a 1% low melting point agarose (Boerhinger Mannheim) and the approximately 450 bp MPL fragment isolated using Qiaquick gel extraction kit (Qiagen) as per manufacturer's instructions.

Each of the isolated fragments described above are mixed at a 1:1 volumetric ratio and used in a PCR reaction using the 5' primer used to amplify the extracellular domain of zcytor17 and ZC17,206 (SEQ ID NO:33) to create a Zcytor17-mpl chimera. Preferred reaction conditions are as follows: 95° C. for 1 min.; 35 cycles at 95° C. for 1 min., 55° C. for 1 min., 72° C. for 2 min.; followed by 72° C. at 10 min.; then a 10° C. soak. The entire PCR product is run on a 1% low melting point agarose (Boehringer Mannheim) and an approximately 1.2 kb Zcytor17-mpl chimera fragment isolated using Qiaquick gel extraction kit (Qiagen) as per manufacturer's instructions. The Zcytor17-mpl chimera fragment is digested with, e.g., EcoRI (BRL) and XbaI (Boerhinger Mannheim) as per manufacturer's instructions. The entire digest is run on a 1% low melting point agarose (Boehringer Mannheim) and the cleaved Zcytor17-mpl chimera isolated using Qiaquick™ gel extraction kit (Qiagen) as per manufacturer's instructions.

The resultant cleaved Zcytor17-mpl chimera is inserted into an expression vector as described below.

Recipient expression vector pZP-5Z is digested with EcoRI (BRL) and HindIII (BRL) as per manufacturer's instructions, and gel purified as described above. This vector fragment is combined with the EcoRI and XbaI cleaved Zcytor17-mpl chimera isolated above and a XbaI/HindIII linker fragment in a ligation reaction. The ligation is run using T4 Ligase (BRL), at 15° C. overnight. A sample of the ligation is electroporated in to DH10B ElectroMAX™ electrocompetent *E. coli* cells (25 μF, 200Ω, 2.3V). Transformants are plated on LB+Ampicillin plates and single colonies screened by PCR to check for the Zcytor17-mpl chimera using a zcytor17 extracellular domain primer and ZC 17,206 (SEQ ID NO:25) using the PCR conditions as described above. Confirmation of the Zcytor17-mpl chimera sequence is made by sequence analyses.

Example 8

Construction of Expression Vector Expressing Full-length zcytor17: pZp7pX/zcytor17

A. Cloning of Full Length Zcytor17 cDNA for Expression:

To obtain a full-length cDNA, 5' and 3' PCR products were isolated and joined using an internal PstI site. The PCR primers were designed using the nucleotide sequence SEQ ID NO:53 and include BamHI and Xho I restriction sites for cloning purposes.

A 5' PCR product was generated using a WI-38 cDNA library as a template and oligonucleotides ZC 29,359 (SEQ ID NO:62) and ZC 27,899 (SEQ ID NO:63) as primers. WI-38 is an in-house cDNA library generated from a human embryonic lung cell line (ATCC CRL-2221). This 5' PCR reaction was run as follows: 30 cycles at 94° C. for 1 minute, 65° C. for 1 minute, 72° C. for 2 minutes, then 72° C. for 7 minutes; 10° C. soak. The PCR reaction used approximately 3 ug of plasmid prepared from the cDNA library, 20 pmoles of each oligonucleotide, and five units of PWO DNA polymerase (Roche). About 90% of the 5' PCR product was ethanol precipitated, digested with BamHI and PstI and gel purified on a 1.0% agarose gel. The approximately 600 bp band was excised and used for ligation to the cloning vector pUC18 digested with BamHI and PstI. The resulting transformants were sequenced to confirm the zcytor17 cDNA sequence. For one of these transformants, plasmid DNA was prepared and digested with BamHI and PstI. The resulting approximately 600 bp band was gel purified and used for a ligation below to form a full-length cDNA.

A 3' PCR product was generated using a human testes in-house cDNA library as a template and oligonucleotides ZC 27,895 (SEQ ID NO:64) and ZC 29,122 (SEQ ID NO:65) as primers. This 3' PCR reaction was run as follows: 30 cycles at 94° C. for 45 seconds, 65° C. for 45 seconds, 72° C. for 2 minutes, then 72° C. for 7 minutes; 10° C. soak. The entire 3' PCR reaction was gel purified on a 1.0% agarose gel and the major 1500 bp band excised. This band was cloned into the PCR Blunt II TOPO vector using the Zeroblunt TOPO kit (Invitrogen). The resulting transformants were sequenced to confirm the zcytor17 cDNA sequence. For one of these transformants, plasmid DNA was prepared and digested with PstI and XhoI. The resulting approximately 1500 bp band was gel purified. A three-part ligation was performed with the 5' BamHI to Pst I fragment above, the 3' PstI to XhoI fragment, and the expression vector pZp7pX digested with BamHI and XhoI. This generated a pZp7pX plasmid containing a full-length cDNA for zcytor17 (SEQ ID NO:53), designated pZp7p/zcytor17. The full length zcytor17 cDNA in pZp7p/zcytor17 has a silent mutations that change the T to G at position 1888 of SEQ ID NO:53 (encoding a Gly residue at residue 464 of SEQ ID NO:54). As this mutation is silent, the zcytor17 cDNA in pZp7p/zcytor17 encodes the polypeptide as shown in SEQ ID NO:54. Plasmid pZp7pX is a mammalian expression vector containing an expression cassette having the CMV promoter, intron A, multiple restriction sites for insertion of coding sequences, and a human growth hormone terminator. The plasmid also has an *E. coli* origin of replication, a mammalian selectable marker expression unit having an SV40 promoter, enhancer and origin of replication, a puromycin resistance gene and the SV40 terminator.

Example 9

Construction of Cells to Assess zcytor17 Based Proliferation in BAF3 Assay Using Alamar Blue A. Construction of BaF3 Cells Expressing Zcytor17-MPL Receptor BaF3 cells expressing the Zcytor17-MPL receptor are constructed as per Example 6A, using 30 μg of the zcytor17 expression vector, described in Example 7. The BaF3 cells expressing the pZP-5Z/zcytor17 receptor plasmid are designated as BaF3/Zcytor17-mpl. These cells are used to screen for a zcytor17 activity as described below in Examples 10 and 18.

B. Construction of BaF3 Cells Expressing zcytor17 Receptor

BaF3 cells expressing the full-length zcytor17 receptor are constructed as per Example 6A, using 30 μg of the zcytor17 expression vector, described in Example 8. The BaF3 cells expressing the pZp7p/zcytor17 receptor plasmid are designated as BaF3/zcytor17. These cells are used to screen for a zcytor17 activity as described below in Examples 10 and 18.

Example 10

Screening for zcytor17 Activity Using BaF3/zcytor17-MPL Cells and Baf3/zcytor17 Cells Using an Alamar Blue Proliferation Assay Baf3/zcytor17-mpl chimera cells and Baf3/zcytor17 cells (Example 9) are spun down and washed independently in mIL-3 free media (Example 6). The cells are spun and washed 3 times to ensure the removal of the mIL-3. Cells are then counted in a hemacytometer. Cells are plated in a 96-well format at 5000 cells per well in a volume of 100 μl per well using the mIL-3 free media.

To try and identify a source for the zcytor17 ligand, approximately 124 conditioned media and samples from a variety of cell lines and tissues are screened. 100 of each conditioned media sample is added to the BaF3/MPL-zcytor17 chimera cells as well as the Baf3/zcytor17 cells. The total assay volume is 200 μl. All known cytokines are also screened at a concentration of about 100 pg/ml-250 ng/ml on both cell lines. Negative controls are run in parallel using mIL-3 free media only. Mouse IL-3 at a concentration of 250 pg/ml is used as a positive control. The assay plates are incubated at 37° C., 5% $CO_2$ for 3 days at which time Alamar Blue (Accumed, Chicago, Ill.) is added at 200 μl/well. Alamar Blue gives a fluorometric readout based on number of live cells, and is thus a direct measurement of cell proliferation in comparison to a negative control. Plates are again incubated at 37° C., 5% $CO_2$ for 24 hours. Plates are read on the Finax™ plate reader (Molecular Devices Sunnyvale, Calif.) using the SoftMax™ Pro program, at wavelengths 544 (Excitation) and 590 (Emission).

Results that show proliferation of on either the Baf3/zcytor17-mpl chimera cell line or the Baf3/zcytor17 cell line in response to conditioned media samples or the known ligands identify a source for the ligand, and suggest that the zcytor17 receptor may signal as a homodimer, or heterodimerize or multimerize with a receptor present in the BaF3 cells. If no signal is present, the actual receptor-signaling complex may heterodimerize or multimerize with another receptor subunit not present in BaF3 cells. See example 18 and Example 19 below.

Example 11

Construction of Mammalian Expression Vectors that Express zcytor17 Soluble Receptors: zcytor17CEE, zcytor17CFLG, zcytor17CHIS and zcytor17-Fc4

A. Construction of zcytor17 Mammalian Expression Vector Containing zcytor17CEE, zcytor17CFLG and zcytor17CHIS An expression vector was prepared for the expression of the soluble, extracellular domain of the zcytor17 polypeptide, pZp9zcytor17CEE, where the construct is designed to express a zcytor17 polypeptide comprised of the predicted initiating methionine and truncated adjacent to the predicted transmembrane domain, and with a C-terminal GLU-GLU tag (SEQ ID NO:34).

An approximately 1500 bp PCR product was generated using ZC29,451 (SEQ ID NO:66) and ZC29,124 (SEQ ID NO:67) as PCR primers to add EcoR1 and BamHI restriction sites. A human HPVS in-house cDNA library was used as a template and PCR amplification was performed as follows: 30 cycles at 94° C. for 1 minute, 65° C. for 1 minute, 72° C. for 1.5 minutes, then 72° C. for 7 minutes; 10° C. soak. The PCR reaction was ethanol precipitated and digested with EcoRI and BamHI restriction enzymes. The digested PCR product was gel purified on a 1.0% agarose gel and the approximately 1500 bp band excised. This band was then re-amplified using identical primers with the following cycling: 30 cycles at 94° C. for 1 minute, 65° C. for 1 minute, 72° C. for 3 minutes, then 72° C. for 7 minutes; 10° C. soak. The PCR reaction was ethanol precipitated and digested with EcoRI and BamHI restriction enzymes. The digested PCR product was gel purified on a 1.0% agarose gel and the approximately 1500 bp band excised. The excised DNA was subcloned into plasmid CEEpZp9 that had been cut with EcoRI and BamHI, to generate plasmid with a GLU-GLU C-terminally tagged soluble receptor for zcytor17, zcytor17CEEpZp9. The extracellular domain in the zcytor17CEE cDNA in zcytor17CEEpZp9 has a silent mutation that changes the T to C at position 1705 of SEQ ID NO:53 (encoding a Pro residue at residue 403 of SEQ ID NO:54). As this mutation is silent, the zcytor17 cDNA in zcytor17CEEpZp9 encodes the polyepptide as shown in SEQ ID NO:54. Moreover, because of the construct used, a Gly-Ser residue pair is inserted C-terminal to the end of the soluble, extracellular domain of zcytor17 and prior to the C-terminal Glu-Glu Tag (SEQ ID NO:34). As such, the tag at the C-terminus of the zcytor17 extracellular domain, was a modified Glu-Glu tag as shown in (SEQ ID NO:91). Plasmid CEEpZp9 is a mammalian expression vector containing an expression cassette having the mouse metallothionein-1 promoter, multiple restriction sites for insertion of coding sequences, and a human growth hormone terminator. The plasmid also has an *E. coli* origin of replication, a mammalian selectable marker expression unit having an SV40 promoter, enhancer and origin of replication, a DHFR gene and the SV40 terminator. Using standard molecular biological techniques zcytor17CEEpZp9 was electroporated into DH10B competent cells (GIBCO BRL, Gaithersburg, Md.) according to manufacturer's direction and plated onto LB plates containing 100 μg/ml ampicillin, and incubated overnight. Colonies were screened by restriction analysis, or PCR from DNA prepared from individual colonies. The insert sequence of positive clones was verified by sequence analysis. A large scale plasmid preparation was done using a QIAGEN® Maxi prep kit (Qiagen) according to manufacturer's instructions.

The same process is used to prepare the zcytor17 soluble receptors with a C-terminal his tag, composed of 6 His residues in a row; and a C-terminal FLAG® tag (SEQ ID NO:35), zcytor17CFLAG. To construct these constructs, the aforementioned vector has either the HIS or the FLAG® tag in place of the glu-glu tag (SEQ ID NO:34).

B. Mammalian Expression Construction of Soluble Human zcytor17 Receptor: zcytor17-Fc4

An expression vector, pEZE-2 hzcytor17/Fc4, was prepared to express a C-terminally Fc4 tagged soluble version of hzcytor17 (human zcytor17-Fc4) in PF CHO cells. PF CHO cells are an in house CHO cell line adapted for growth in protein-free medium (ExCell 325 PF medium; JRH Biosciences). The in house CHO cell line was originally derived from CHO DG44 cells (G. Urlaub, J. Mitchell, E. Kas, L. A. Chasin, V. L. Funanage, T. T. Myoda and J. L. Hamlin, "The Effect Of Gamma Rays at the Dihydrofolate Reductase Locus: Deletions and Inversions," Somatic Cell and Malec. Genet., 12: 555-566 (1986). A fragment of zcytor17 cDNA that includes the polynucleotide sequence from extracellular domain of the zcytor17 receptor was fused in frame to the Fc4 polynucleotide sequence (SEQ ID NO:36) to generate a zcytor17-Fc4 fusion (SEQ ID NO:68 and SEQ ID NO:69). The pEZE-2 vector is a mammalian expression vector that contains the Fc4 polynucleotide sequence and a cloning site that allows rapid construction of C-terminal Fc4 fusions using standard molecular biology techniques.

A 1566 base pair fragment was generated by PCR, containing the extracellular domain of human zcytor17 and the first two amino acids of Fc4 (Glu and Pro) with FseI and BglII sites coded on the 5' and 3' ends, respectively. This PCR fragment was generated using primers ZC29,157 (SEQ ID NO:70) and ZC29,150 (SEQ ID NO:71) by amplification from a plasmid containing the extracellular domain of human zcytor17 (pZp9zcytor17CEE) (Example 11A). The PCR reaction conditions were as follows: 25 cycles of 94° C. for 1 minute, 60° C. for 1 minute, and 72° C. for 2 minutes; 1 cycle at 72° C. for 10 minutes; followed by a 4° C. soak. The fragment was digested with FseI and BglII restriction endonucleases and subsequently purified by 1% gel electrophoresis and band purification using QiaQuick gel extraction kit (Qiagen). The resulting purified DNA was ligated for 5 hours at room temperature into a pEZE-2 vector previously digested with FseI and BglII containing Fc4 3' of the FseI and BglII sites.

Two μl of the ligation mix was electroporated in 37 μl DH10B electrocompetent *E. coli* (Gibco) according to the manufacturer's directions. The transformed cells were diluted in 400 μl of LB media and plated onto LB plates containing 100 μg/ml ampicillin. Clones were analyzed by restriction digests and positive clones were sent for DNA sequencing to confirm the sequence of the fusion construct. 1 μl of a positive clone was transformed into 37 μl of DH10B electrocompetent *E. coli* and streaked on a LB/amp plate. A single colony was picked from this streaked plate to start a 250 ml LB/amp culture that was then grown overnight at 37° C. with shaking at 250 rpm. This culture was used to generate 750 μg of purified DNA using a Qiagen plasmid Maxi kit (Qiagen).

Example 12

Transfection and Expression of Zcytor17 Soluble Receptor Polypeptides

BHK 570 cells (ATCC No. CRL-10314), DG-44 CHO, or other mammalian cells are plated at about $1.2\times10^6$ cells/well (6-well plate) in 800 μl of appropriate serum free (SF) media (e.g., DMEM, Gibco/BRL High Glucose) (Gibco BRL, Gaithersburg, Md.). The cells are transfected with expression plasmids containing zcytor17CEE, zcytor17CFLG, zcytor17CHIS or zcytor17-Fc4 (Example 11), using Lipofectin™ (Gibco BRL), in serum free (SF) media according to manufacturer's instruction. Single clones expressing the soluble receptors are isolated, screened and grown up in cell culture media, and purified using standard techniques.

A. Mammalian Expression of Soluble Human zcytor17CEE Receptor

BHK 570 cells (ATCC NO: CRL-10314) were plated in T-75 tissue culture flasks and allowed to grow to approximately 50 to 70% confluence at 37° C., 5% $CO_2$, in DMEM/FBS media (DMEM, Gibco/BRL High Glucose, (Gibco BRL, Gaithersburg, Md.), 5% fetal bovine serum, 1 mM L-glutamine (TRH Biosciences, Lenea, Kans.), 1 mM sodium pyruvate (Gibco BRL)). The cells were then transfected with the plasmid containing zcytor17CEE (Example 11A) using Lipofectamine™ (Gibco BRL), in serum free (SF) media formulation (DMEM, 10 mg/ml transferrin, 5 mg/ml 2 mg/ml fetuin, 1% L-glutamine and 1% sodium pyruvate). Ten μg of the plasmid DNA pZp9zcytor17CEE (Example 11A) was diluted into a 15 ml tube to a total final volume of 500 μl with SF media. 50 μl of Lipofectamine was mixed with 450 μl of SF medium. The Lipofectamine mix was added to the DNA mix and allowed to incubate approximately 30 minutes at room temperature. Four ml of SF media was added to the DNA:Lipofectamine mixture. The cells were rinsed once with 5 ml of SF media, aspirated, and the DNA: Lipofectamine mixture was added. The cells were incubated at 37° C. for five hours, and then 5 ml of DMEM/10% FBS media was added. The flask was incubated at 37° C. overnight after which time the cells were split into the selection media (DMEM/FBS media from above with the addition of 1 μM methotrexate or 10 μM Methotrexate (Sigma Chemical Co., St. Louis, Mo.) in 150 mm plates at 1:2, 1:10, and 1:50. Approximately 10 days post-transfection, one 150 mm plate of 1 μM methotrexate resistant colonies was trypsinized, the cells were pooled, and one-half of the cells were replated in 10 μM methotrexate; to further amplify expression of the zcytor17CEE protein. A conditioned-media sample from this pool of amplified cells was tested for expression levels using SDS-PAGE and Western analysis.

B. Mammalian Expression of Soluble Human zcytor17-Fc4 Receptor

Twenty μg of pEZE-2 hzcytor17Fc4 plasmid DNA (Example 11B) was linearized by restriction digestion with FspI, a restriction enzyme that cuts once within the pEZE-2 vector and does not disturb genes necessary for expression. 200 μg of sheared salmon sperm DNA was added as carrier DNA and then the DNA was precipitated by addition of 0.1 volumes of 3M Sodium Acetate pH 5.2 and 2.2 volumes ethanol followed by a 15 minute ice incubation and microcentrifugation at 4° C. The resulting DNA pellet was washed in 70% ethanol and air dried before being resuspended in 100 μl PF CHO non-selection growth media (21 g/L PF CHO Ex Cell 325/200 mM L-glutamine (Gibco)/100 mM sodium pyruvate (Gibco)/1× HT Supplement (Gibco). Five million PF CHO passage 43 cells were added to the DNA in 600 μl of PF CHO non-selection growth media and then electroporated in a Gene Pulser II Electroporation system (BioRad) using 1070 μF capacitance and 380 volts using a 0.4 cm gap Gene Pulser (BioRad) electroporation cuvette. The electroporated cells were allowed to recover for 48 hours in non-selection growth media before selection in −HT media (21 g/L PF CHO Ex Cell 325/200 mM L-glutamine (Gibco)/100 mM sodium pyruvate (Gibco). Cells were selected for 5 days in −HT media before being passaged at $5\times10^5$ ml into 50 nm MTX selection. Cells selected at 50 nm MTX were seeded at $6\times10^5$ ml in a shake flask to generate conditioned media. The resulting 72 hour conditioned media was analyzed by probing western blots with an antibody generated against human Ig. The cells produced hzcytor17/Fc4 protein at approximately 1 mg/L.

C. Larger-scale Mammalian Expression of Soluble Human zcytor17-Fc4 Receptor

Two hundred μg of pEZE-2 hzcytor17Fc4 plasmid DNA (Example 11B) was linearized by restriction digestion with FspI, a restriction enzyme that cuts once within the pEZE-2 vector and does not disturb genes necessary for expression. 200 μg of CHO genomic DNA (prepared in-house) was added as carrier DNA and then the DNA was precipitated by addition of 0.1 volumes of 3M Sodium Acetate pH 5.2 and 2.5 volumes ethanol followed by microcentrifugation at Room temperature. Five replicate DNA pellets were made and transformed. The resulting DNA pellet was washed in 70% ethanol and air dried before being resuspended in 100 μl PF CHO non-selection growth media (21 g/L PF CHO Ex Cell 325/200 mM L-glutamine (Gibco)/100 mM sodium pyruvate (Gibco)/1×HT Supplement (Gibco). Ten million PF CHO cells were added to the DNA in 600 μl of PF CHO non-selection growth media and then electroporated in a Gene Pulser II Electroporation system (BioRad) using 950 μF capacitance and 300 volts using a 0.4 cm gap Gene Pulser (BioRad) electroporation cuvette. The electroporated cells were pooled and put directly into selection in −HT media (21 g/L PF CHO Ex Cell 325/200 mM L-glutamine (Gibco)/100 mM sodium pyruvate (Gibco). Cells were selected for 14 days in −HT media before being passaged at $4\times10^5$/ml into 50 nm MTX selection. Cells were amplified to 200 nM MTX and then to 1 uM MTX. The −HT, 50 nM, and 1 uM pools were seeded at $1\times10^6$ c/ml for 48 hours, and the resulting conditioned media was analyzed by probing western blots with an antibody generated against human Ig.

C. Transient Mammalian Expression and Purification of Soluble Human zcytor17-Fc4 Receptor pEZE-2 hzcytor17Fc4 plasmid DNA (Example 11B) was introduced into 40 maxi plates of MIK cells using Lipofectamine (Gibco BRL) as described herein and in manufacturer's instructions. Cells were allowed to recover overnight, then were rinsed and refed with serum-free medium (SL7V4, made in-house). After 72 hours, the media was collected and filtered, and cells were refed with serum-free medium. After 72 hours, the media was again collected and filtered.

The serum-free conditioned media (2×1.5 L batches) from transiently transfected BHK cells was pumped over a 1.5 ml Protein A-agarose column in 20 mM Tris, pH 7.5, 0.5 M NaCl. The column was washed extensively with this buffer and then the bound protein was eluted with 1 ml of 0.2 M glycine, pH 2.5, 0.5 M NaCl. The eluted protein was collected into 0.1 ml of 2 M Tris, pH 8.5.

Aliquots were collected for SDS-polyacrylamide gel electrophoresis and the bulk zcytor17-Fc was dialyzed overnight against PBS. The soluble receptor was sterile filtered and placed in aliquots at −80° C.

Example 13

Expression of zcytor17 Soluble Receptor in *E. coli*

A. Construction of expression Vector pCZR225 that Expresses huzcytor17/MBP-6H Fusion Polypeptide An expression plasmid containing a polynucleotide encoding a zcytor17 soluble receptor fused C-terminally to maltose binding protein (MBP) was constructed via homologous recombination. The fusion polypeptide contains an N-terminal approximately 388 amino acid MBP portion fused to any of the zcytor17 soluble receptors described herein. A fragment of zcytor17 cDNA (SEQ ID NO:1, SEQ ID NO:45, SEQ ID NO:17 or SEQ ID NO:21) was isolated using PCR as described herein. Two primers were used in the production of the zcytor17 fragment in a standard PCR reaction: (1) one containing about 40 bp of the vector flanking sequence and about 25 bp corresponding to the amino terminus of the zcytor17, and (2) another containing about 40 bp of the 3' end corresponding to the flanking vector sequence and about 25 bp corresponding to the carboxyl terminus of the zcytor17. Two μl of the 100 μl PCR reaction was run on a 1.0% agarose gel with 1×TBE buffer for analysis, and the expected approximately fragment was seen. The remaining PCR reaction was combined with the second PCR tube and precipitated with 400 μl of absolute ethanol. The precipitated DNA used for recombining into the Sma1 cut recipient vector pTAP170 to produce the construct encoding the MBP-zcytor17 fusion, as described below.

Plasmid pTAP170 was derived from the plasmids pRS316 and pMAL-c2. The plasmid pRS316 was a *Saccharomyces cerevisiae* shuttle vector (Hieter P. and Sikorski, R., *Genetics* 122:19-27, 1989). pMAL-C2 (NEB) was an *E. coli* expression plasmid. It carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoRI cut pMAL-c2 was recombined with 1 μg Pvu1 cut pRS316, 1 μg linker, and 1 μg Sca1/EcoR1 cut pRS316 were combined in a PCR reaction. PCR products were concentrated via 100% ethanol precipitation.

Competent yeast cells (*S. cerevisiae*) were combined with about 10 μl of a mixture containing approximately 1 μg of the zcytor17 receptor PCR product above, and 100 ng of SmaI digested pTAP98 vector, and electroporated using standard methods and plated onto URA-D plates and incubated at 30° C.

After about 48 hours, the Ura+ yeast transformants from a single plate were picked, DNA was isolated, and transformed into electrocompetent *E. coli* cells (e.g., MC1061, Casadaban et. al. *J. Mol. Biol.* 138, 179-207), and plated on MM/CA +AMP 100 mg/L plates (Pryor and Leiting, *Protein Expression and Purification* 10:309-319, 1997). using standard procedures. Cells were grown in MM/CA with 100 μg/ml Ampicillin for two hours, shaking, at 37° C. 1 ml of the culture was induced with 1 mM IPTG. 2-4 hours later the 250 μl of each culture was mixed with 250 μl acid washed glass beads and 250 μl Thorner buffer with 5% ME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were designated pCZR225 and subjected to sequence analysis.

One microliter of sequencing DNA was used to transform strain BL21. The cells were electropulsed at 2.0 kV, 25 μF and 400 ohms. Following electroporation, 0.6 ml MM/CA with 100 mg/L Ampicillin. Cells were grown in MM/CA and induced with ITPG as described above. The positive clones were used to grow up for protein purification of the huzcytor17/MBP-6H fusion protein using standard techniques.

B. Purification of huzcytor17/MBP-6H Soluble Receptor from *E. coli* Fermentation Unless otherwise noted, all operations were carried out at 4° C. The following procedure was used for purifying huzcytor17/MBP-6H soluble receptor polypeptide. *E. coli* cells containing the pCZR225 construct and expressing huzcytor17/MBP-6H soluble receptor (Example 13A) were grown up in SuperBroth II (12 g/L Casien, 24 g/L Yeast Extract, 11.4 g/L di-potassium phosphate, 1.7 g/L Mono-potassium phosphate; Becton Dickenson, Cockeysville, Md.), and frozen in 0.5% glycerol. Twenty grams of the frozen cells in SuperBroth II+Glycerol were used to purify the protein. The frozen cells were thawed and diluted 1:10 in a protease inhibitor solution (Extraction buffer) prior to lysing the cells and releasing the huzcytor17/MBP-6H soluble receptor protein. The diluted cells contained final concentrations of 20 mM Iris (JT Baker, Philipsburg, N.J.) 100 mM Sodium Chloride (NaCl, Mallinkrodt, Paris, Ky.), 0.5 mM phenylmethylsulfonyl fluoride (PMSF, Sigma Chemical Co., St. Louis, Mo.), 2 μg/ml Leupeptin (Fluka, Switzerland), and 2 μg/ml Aprotinin (Sigma). A French Press cell breaking system (Constant Systems Ltd., Warwick, UK) with temperature of −7 to −10° C. and 30K PSI was used to lyse the cells. The diluted cells were checked for breakage by $A_{600}$ readings before and after the French Press. The lysed cells were centrifuged @ 18,000 G for 45 minutes to remove the broken cell debris, and the supernatant used to purify the protein.

A 25 ml column of Amylose resin (New England Biolabs, Beverly, Mass.) (prepared as described below) was poured in a Bio-Rad, 2.5 cm D×10 cm H glass column. The column was packed and equilibrated by gravity with 10 column volumes (CVs) of Amylose Equilibration buffer (20 mM Tris, 100 mM NaCl, pH 8.0). The supernatant was batch loaded to the Amylose resin and was rocked overnight. The resin was poured back into the column and was washed with 10 CV's of Amylose Equilibration buffer by gravity. The column was washed for 10 CVs with Amylose equilibration buffer, then eluted with ~2 CV of Amylose equilibration buffer+10 mM Maltose (Fluka Biochemical, Switzerland) by gravity. 5 ml fractions were collected over the entire chromatography and absorbance at 280 and 320 nM were read. The Amylose column was regenerated with 1 CV of distilled $H_2O$, 5 CVs of 0.1% (w/v) SDS (Sigma), 5 CVs of distilled $H_2O$, and then 5 CVs of Amylase equilibration buffer.

Fractions of interest were pooled and dialyzed in a Slide-A-Lyzer (Pierce) with 4×4 L PBS pH 7.4 (Sigma) to remove low molecular weight contaminants, buffer exchange and desalt. After the changes of PBS, the material harvested represented the purified huzcytor17/MBP-6H polypeptide. The purified huzcytor17/MBP-6H polypeptide was analyzed via SDS-PAGE Coomassie staining and Western blot analyses with the anti-rabbit HRP conjugated antibody (Rockland, Gilbertsville, Pa.). The concentration of the huzcytor17/MBP-6H polypeptide was 1.92 mg/ml as determined by BCA analysis.

Purified huzcytor17/MBP-6H polypeptide was prepared for injection into rabbits and sent to R & R Research and Development (Stanwood, Wash.) for antibody production. Rabbits were injected to produce anti anti-huzcytor17/MBP-6H serum (Example 15, below).

Example 14

Zcytor17 Soluble Receptor Polyclonal Antibodies

Polyclonal antibodies were prepared by immunizing 2 female New Zealand white rabbits with the purified huzcytor17/MBP-6H polypeptide (Example 13). The rabbits are each given an initial intraperitoneal (IP) injection of 200 μg of purified protein in Complete Freund's Adjuvant (Pierce, Rockford, Ill.) followed by booster IP injections of 100 ug purified protein in Incomplete Freund's Adjuvant every three weeks. Seven to ten days after the administration of the third booster injection, the animals are bled and the serum is collected. The rabbits are then boosted and bled every three weeks.

The zcytor17-specific polyclonal antibodies are affinity purified from the rabbit serum using an CNBr-SEPHAROSE 4B protein column (Pharmacia LKB) that is prepared using about 10 mg of the purified huzcytor17/MBP-6H polypeptide per gram CNBr-SEPHAROSE, followed by 20× dialysis in PBS overnight. Zcytor17-specific antibodies are characterized by an ELISA titer check using 1 ug/ml of the appropriate protein antigen as an antibody target. The lower limit of detection (LLD) of the rabbit anti-zcytor17 affinity purified antibodies is determined using standard methods.

Example 15

Zcytor17 Receptor Monoclonal Antibodies

Zcytor17 soluble receptor Monoclonal antibodies are prepared by immunizing female BalbC mice with the purified recombinant soluble zcytor17 proteins described herein. The mice are each given an initial intraperitoneal (IP) injection of 20 ug of purified protein in Complete Freund's Adjuvant (Pierce, Rockford, Ill.) followed by booster IP injections of 10 ug purified protein in Incomplete Freund's Adjuvant every two weeks. Seven to ten days after the administration of the third booster injection, the animals are bled and the serum is collected, and antibody titer assessed.

Splenocytes are harvested from high-titer mice and fused to murine SP2/0 myeloma cells using PEG 1500 (Boerhinger Mannheim, UK) using a 4:1 fusion ratio of splenocytes to myeloma cells (*Antibodies: A Laboratory Manual*, E. Harlow and D. Lane, Cold Spring Harbor Press). Following 10 days growth post-fusion, specific antibody-producing hybridomas are identified by ELISA using purified recombinant zcytor17 soluble receptor protein (Example 6C) as an antibody target and by FACS using Baf3 cells expressing the zcytor17 sequence (Example 8) as an antibody target. The resulting hybridomas positive by both methods are cloned three times by limiting dilution.

Example 16

Assessing Zcytor17 Receptor Heterodimerization Using ORIGEN Assay

Soluble zcytor17 receptor zcytor17CFLAG (Example 11), or gp130 (Hibi, M. et al., Cell 63:1149-1157, 1990) are biotinylated by reaction with a five-fold molar excess of sulfo-NHS-LC-Biotin (Pierce, Inc., Rockford, Ill.) according to the manufacturer's protocol. Soluble zcytor17 receptor and another soluble receptor subunit, for example, soluble gp130, LIF, IL-12, WSX-1, IL-7Rα (sIL-7Rα) or IL-2 receptor-γ (sIL-2Rγ) (R&D Systems, Minneapolis, Minn.), or soluble zalpha11 receptor (IL-21R; commonly owned U.S. patent application Ser. No. 09/404,641) are labeled with a five fold molar excess of Ru-BPY-NHS (Igen, Inc., Gaithersburg, Md.) according to manufacturer's protocol. The biotinylated and Ru-BPY-NHS-labeled forms of the soluble zcytor17 receptor can be respectively designated Bio-zcytor17 receptor and Ru-zcytor17; the biotinylated and Ru-BPY-NHS-labeled forms of the other soluble receptor subunit can be similarly designated. Assays can be carried out using conditioned media from cells expressing a ligand that binds zcytor17 heterodimeric receptors, or using purified ligands. Preferred ligands are those that can bind class 1 heterodimeric cytokine receptors such as, gp130, LIF, IL-12, IL-2, IL-4, IL-7, IL-9, IL-15, zalpha11 Ligand (IL-21) (commonly owned U.S. patent application Ser. No. 09/522,217), TSLP (Levine, S D et al., ibid.; Isaksen, D E et al., ibid.; Ray, R J et al., ibid.; Friend, S L et al., ibid.).

For initial receptor binding characterization a panel of cytokines or conditioned medium are tested to determine whether they can mediate homodimerization of zcytor17 receptor and if they can mediate the heterodimerization of zcytor17 receptor with the soluble receptor subunits described above. To do this, 50 μl of conditioned media or TBS-B containing purified cytokine, is combined with 50 μl of TBS-B (20 mM Tris, 150 mM NaCl, 1 mg/ml BSA, pH 7.2) containing e.g., 400 ng/ml of Ru-zcytor17 receptor and Bio-zcytor17, or 400 ng/ml of Ru-zcytor17 receptor and e.g., Bio-gp130, or 400 ng/ml of e.g., Ru-IL2Rγ and Bio-zcytor17. Following incubation for one hour at room temperature, 30 μg of streptavidin coated, 2.8 mm magnetic beads (Dynal, Inc., Oslo, Norway) are added and the reaction incubated an additional hour at room temperature. 200 μl ORIGEN assay buffer (Igen, Inc., Gaithersburg, Md.) is then added and the extent of receptor association measured using an M8 ORIGEN analyzer (Igen, Inc.).

Example 17

Construct for Generating a zcytor17 Receptor Heterodimer

A vector expressing a secreted human zcytor17 heterodimer is constructed. In this construct, the extracellular cytokine-binding domain of zcytor17 is fused to the heavy chain of IgG gamma 1 (IgGγ1) (SEQ ID NO:37 and SEQ ID NO:38), while the extracellular portion of the heteromeric cytokine receptor subunit (E.g., an gp130, LIF, IL-12, WSX-1, or IL-2 receptor component (IL-2Rα, IL-2Rγ), an IL-4/IL-13 receptor family receptor components (IL-4Rα, IL-13Rα, IL-13Rα'), interleukin receptor subunits (e.g., IL-15 Rα, IL-7Rα, IL-9Rα); or zalpha11 receptor (IL-21R)) is fused to a human kappa light chain (human κ light chain) (SEQ ID NO:39 and SEQ ID NO:40).

A. Construction of IgG Gamma 1 and Human κ Light Chain Fusion Vectors

The heavy chain of IgGγ1 (SEQ ID NO:37) is cloned into the Zem229R mammalian expression vector (ATCC deposit No. 69447) such that any desired cytokine receptor extracellular domain having a 5' EcoRI and 3' NheI site can be cloned in resulting in an N-terminal extracellular domain-C-terminal IgGγ1 fusion. The IgGγ1 fragment used in this construct is made by using PCR to isolate the IgGγ1 sequence from a Clontech hFetal Liver cDNA library as a template. PCR products are purified using methods described herein and digested with MluI and EcoRI (Boerhinger-Mannheim), ethanol precipitated and ligated with oligos ZC11,440 (SEQ ID NO:41) and ZC11,441 (SEQ ID NO:42), which comprise an MluI/EcoRI linker, into Zem229R previously digested with and EcoRI using standard molecular biology techniques disclosed herein.

The human κ light chain (SEQ ID NO:39) is cloned in the Zem228R mammalian expression vector (ATCC deposit No. 69446) such that any desired cytokine receptor extracellular domain having a 5' EcoRI site and a 3' KpnI site can be cloned in resulting in a N-terminal cytokine extracellular domain-C-terminal human κ light chain fusion. As a KpnI site is located within the human κ light chain sequence (cleaved by the KpnI enzyme after nucleotide 62 in SEQ ID NO:39), a special primer is designed to clone the 3' end of the desired extracellular domain of a cytokine receptor into this KpnI site: The primer is designed so that the resulting PCR product contains the desired cytokine receptor extracellular domain with a segment of the human κ light chain up to the KpnI site (SEQ ID NO:39). This primer preferably comprises a portion of at least 10 nucleotides of the 3' end of the desired cytokine receptor extracellular domain fused in frame 5' to SEQ ID NO:39. The human κ light chain fragment used in this construct is made by using PCR to isolate the human κ light chain sequence from the same Clontech human Fetal Liver cDNA library used above. PCR products are purified using methods described herein and digested with MluI and EcoRI (Boerhinger-Mannheim), ethanol precipitated and ligated with the MluI/EcoRI linker described above, into Zem228R previously digested with and EcoRI using standard molecular biology techniques disclosed herein.

B. Insertion of Zcytor17 Receptor or Heterodimeric Subunit Extracellular Domains into Fusion Vector Constructs Using the construction vectors above, a construct having zcytor17 fused to IgGγ1 is made. This construction is done by PCRing the extracellular domain or cytokine-binding domain of zcytor17 receptor described herein from a prostate cDNA library (Clontech) or activated lymphocyte cDNA library using standard methods (E.g., Example 7), and oligos that provide EcoRI and NheI restriction sites. The resulting PCR product is digested with EcoRI and NheI, gel purified, as described herein, and ligated into a previously EcoRI and NheI digested and band-purified Zem229R/IgGγ1 described above. The resulting vector is sequenced to confirm that the zcytor17/IgG gamma 1 fusion (zcytor17/Ch1 IgG) is correct.

A separate construct having a heterodimeric cytokine receptor subunit extracellular domain fused to κ light is also constructed as above. The cytokine receptor/human κ light chain construction is performed as above by PCRing from, e.g., a lymphocyte cDNA library (Clontech) using standard methods, and oligos that provide EcoRI and KpnI restriction sites. The resulting PCR product is digested with EcoRI and KpnI and then ligating this product into a previously EcoRI and KpnI digested and band-purified Zem228R/human κ light chain vector described above. The resulting vector is sequenced to confirm that the cytokine receptor subunit/human κ light chain fusion is correct.

D. Co-expression of the zcytor17 and Heterodimeric Cytokine Receptor Subunit Extracellular Domain Approximately 15 μg of each of vectors above, are co-transfected into mammalian cells, e.g., BHK-570 cells (ATCC No. CRL-10314) using LipofectaminePlus™ reagent (Gibco/BRL), as per manufacturer's instructions. The transfected cells are selected for 10 days in DMEM 5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants is selected again in 10 μm of MTX and 0.5 mg/ml G418 for 10 days.

The resulting pool of doubly selected cells is used to generate protein. Three Factories (Nunc, Denmark) of this pool are used to generate 10 L of serum free conditioned medium. This conditioned media is passed over a 1 ml protein-A column and eluted in about 10, 750 microliter fractions. The fractions having the highest protein concentration are pooled and dialyzed (10 kD MW cutoff) against PBS. Finally the dialyzed material is submitted for amino acid analysis (AAA) using routine methods.

Example 18

Determination of Receptor Subunits that Heterodimerize or Multimerize with zcytor17 Receptor Using standard methods described herein, The BaF3/MPL-zcytor17 chimera cells (Example 6) are transfected with an additional heterodimeric cytokine receptor subunit serve as a bioassay cell line to measure signal transduction response of heterodimeric zcytor17 receptor complexes to the luciferase reporter in the presence of TPO (Example 6). Transfection of the BaF3/MPL-zcytor17 cell line with and additional MPL-class 1 cytokine receptor fusion that signals in the presence of the TPO ligand, determines which heterodimeric cytokine receptor subunits are required for zcytor17 receptor signaling. Use of MPL-receptor fusions for this purpose alleviates the requirement for the presence of a natural ligand for the zcytor17 receptor.

MPL-class I cytokine receptor fusions are made as per Example 5 using the extracellular domain and transmembrane domains of the MPL receptor and the intracellular signaling domain of the desired class I cytokine receptor. The BaF3/MPL-zcytor17 bioassay cell line co-transfected with an individual MPL-class I cytokine receptor fusions as per Example 6 to form a BaF3/MPL-zcytor17/MPL-class I cytokine receptor cell line. Receptor complexes include but are not limited to zcytor17 receptor in combination with an MPL-cytokine receptor fusion comprising a gp130, LIF, IL-12, or WSX-1 component, or one or more of the IL-2 receptor components (IL-2Rα, IL 2Rβ, IL-2Rγ), zcytor17 receptor with one or more of the IL-4/IL-13 receptor family receptor components (IL-4Rα, IL-13Rα, IL-13Rα'), as well as other Interleukin receptors (e.g., IL-15 Rα, IL-7Rα, IL-9Rα, IL-21R (Zalpha11 receptor)). Each independent receptor complex cell line is then assayed in the presence of TPO (example 6) and proliferation measured using routine methods (e.g., Alamar Blue assay as described in Example 6). The BaF3/MPL-zcytor17 bioassay cell line serves as a control for the background activity, and is thus used as a baseline to compare signaling by the various receptor complex combinations. Moreover, assay by luciferase reporter assay (activation of transcription of a reporter gene) can also be used as a way to measure signaling regardless of induction of proliferation. In addition, a BaF3/MPL-class I cytokine receptor cell line can be constructed to control for MPL-class I cytokine receptor homodimerization effects for those class I cytokine receptors known to signal upon homodimerization. The TPO in the presence of the correct receptor complex, is expected to increase proliferation of the BaF3/MPL-zcytor17/MPL-class I cytokine receptor cell line approximately 5 fold over background or greater in the presence of TPO.

Example 19

Reconstitution of zcytor17 Receptor In vitro

To identify components involved in the zcytor17-signaling complex, receptor reconstitution studies are performed as follows. For example, BHK 570 cells (ATCC No. CRL-10314) transfected, using standard methods described herein, with a luciferase reporter mammalian expression vector plasmid serve as a bioassay cell line to measure signal transduction response from a transfected zcytor17 receptor complex to the luciferase reporter in the presence of zcytor17 Ligand. BHK cells would be used in the event that BHK cells do not endogenously express the zcytor17 receptor. Other cell lines can be used. An exemplary luciferase reporter mammalian expression vector is the KZ134 plasmid which is constructed with complementary oligonucleotides ZC12,749 (SEQ ID NO:43) and ZC12,748 (SEQ ID NO:44) that contain STAT transcription factor binding elements from 4 genes. A modified c-fos S is inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and are ligated, using standard methods, into a recipient firefly luciferase reporter vector with a c-Fos promoter (Poulsen, L. K. et al., *J. Biol. Chem.* 273:6229-6232, 1998) digested with the same enzymes and containing a neomycin selectable marker. The KZ134 plasmid is used to stably transfect BHK, or BaF3 cells, using standard transfection and selection methods, to make a BHK/KZ134 or BaF3/KZ134 cell line respectively.

The bioassay cell line is transfected with zcytor17 receptor alone, or co-transfected with zcytor17 receptor along with one of a variety of other known receptor subunits. Receptor complexes include but are not limited to zcytor17 receptor only, various combinations of zcytor17 receptor with gp130, LIF, IL-12, or WSX-1 receptor subunits, or one or more of the IL-2 receptor components (IL-2Rα, IL-2Rβ, IL-2Rγ), zcytor17 receptor with one or more of the IL-4/IL-13 receptor family receptor components (IL-4Rα, IL-13Rα, IL-13Rα'), as well as other Interleukin receptors (e.g., IL-15 Rα, IL-7Rα, IL-9Rα, IL-21R (zalpha11)). Each independent receptor complex cell line is then assayed in the presence of cytokine-conditioned media or purified cytokines and luciferase activity measured using routine methods. The untransfected bioassay cell line serves as a control for the background luciferase activity, and is thus used as a baseline to compare signaling by the various receptor complex combinations. The conditioned medium or cytokine that binds the zcytor17 receptor in the presence of the correct receptor complex, is expected to give a luciferase readout of approximately 5 fold over background or greater.

As an alternative, a similar assay can be performed wherein the Baf3/zcytor17-mpl and Baf3/zcytor17 (Example 10) cell lines are co-transfected as described above and proliferation measured.

Example 20

Construction of BaF3 Cells Expressing Full-Length Zcytor17

BaF3, an interleukin-3 (IL-3) dependent prelymphoid cell line derived from murine bone marrow (Palacios and Steinmetz, *Cell* 41: 727-734, 1985; Mathey-Prevot et al., *Mol. Cell. Biol.* 6.: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R+D, Minneapolis, Minn.), 2 mM. L-glutamine (Gibco-BRL), and 1 mM Sodium Pyruvate (Gibco-BRL).

BaF3 cells for electroporation were washed twice in PBS, pH 7.2 (Gibco-BRL) and then resuspended in PBS and a cell density of $10^7$ cells/ml. One ml of resuspended BaF3 cells was mixed with 30 μg of the pZP7PX/zcytor17 plasmid DNA and transferred to separate disposable electroporation chambers (Gibco-BRL). The cells were then given 2 serial shocks (800 lFad/300V.; 1180 lFad/300V.) delivered by an electroporation apparatus (CELL-PORATOR™; Gibco-BRL). The electroporated cells were then transferred to 20 mls of complete media and placed in an incubator for 48 hours (37° C., 5% $CO_2$). The cells were then spun down and resuspended in 20 mis of complete media containing 2 μg/ml Puromycin (ClonTech) Selection in a T75 flask to isolate the puromycin resistant pool. Clonal lines of the transfected BaF3 cells, hereinafter called BaF3/zcytor17 cells, were isolated as described below.

BaF3/zcytor17 cells were counted in a hemocytometer, and plated at 1 cell/well, 0.5 cell/well, 0.1 cell/well, and 0.01 cell/well, in a volume of 100 μl/well in complete media containing 2 μg/ml Puromycin. 15 clones were scaled up to T75 flasks, and 5 clones were assayed for RNA production. Cells were washed once with PBS and counted with a hemocytometer. $5\times10^6$ cells were spun down and the media removed. Untransfected BaF3 cells were also counted and pelleted. Four of the pellets were frozen at −80° C. overnight. RNA was isolated using the S.N.A.P.™ Total RNA Isolation Kit (Invitrogen) as per manufacturer's instructions, and total RNA yield was determined by spectrophotometer. The amount of zcytor17 RNA was then determined by RT-PCR using the RT-PCR Kit (Stratagene) as per manufacturer's instructions, using zcytor17-specific primers ZC29,180 (SEQ ID NO:72) and ZC29,122 (SEQ ID NO:65). One clone that gave a strong band of zcytor17 RNA was selected to use in BaF3 Alamar Blue proliferation assays (Example 6) to test potential ligands.

Example 21

Cloning of Mouse zcytoR17 from a Mouse Testes cDNA Library

A mouse testes cDNA library was screened for a full-length clone of mouse zcytoR17. The library was plated at 65,500 cfu/plate on 24 LB +Amp plates. Filter lifts were prepared using Hybond N (Amersham-Pharmacia Biotech, Inc., Piscataway, N.J.) on a total of approximately 1.6 million colonies. The filters were marked with a hot needle for orientation and then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was affixed to the filters using a UV crosslinker (Stratalinker®, Stratagene, La Jolla, Calif.) at 1200 joules. The filters were then left to dry overnight at room temperature.

The next day, the filters were pre-washed at 65° C. in pre-wash buffer consisting of 0.25×SSC, 0.25% SDS and 1 mM EDTA. Cell debris was manually removed using Kimwipes® (Kimberly-Clark) and the solution was changed 3 times over a period of 1 hour. Filters were air dried and stored at room temperature until needed. The filters were then pre-hybridized for approximately 3 hours at 63° C. in 20 ml of ExpressHyb™ Hybridization Solution (Clontech, Palo Alto, Calif.).

Probe B (Example 3C) was generated by PCR from human zcytoR17 template using oligonucleotide primers ZC27,895 (SEQ ID NO:64) and ZC28,917 (SEQ ID NO:73) and was radioactively labeled with $^{32}P$ using a commercially available kit (Megaprime DNA Labeling System; Amersham Pharmacia Biotech, Piscataway, N.J.) according to the manufacturer's instructions. The probe was purified using a Stratagene™ push column (NucTrap® column; Stratagene, La Jolla, Calif.). The probe was denatured at 100° C. for 15 min and added to ExpressHyb™. Filters were hybridized in 15 ml hybridizing solution containing $1.6\times10^6$ cpm/ml of probe at 63° C. overnight. Filters were washed at 55° C. in 2×SSC, 0.1% SDS and 1 mM EDTA and exposed to X-ray film at −80° C. for 4½ days. Thirteen positives were picked from the plates as plugs and placed in 1 ml LB +amp in 1.7 ml tubes. Tubes were placed at 4° C. overnight. These 13 positives were subjected to two further rounds of purification. The tertiary plates were outgrown at 37° C. after filter lifts were taken and single colonies were picked and sent to sequencing. Three of these were determined to contain sequence of the mouse ortholog of zcytoR17.

In addition, a PCR product was generated using CTLL-2 cDNA as a template and oligonucleotides ZC38,239 (SEQ ID NO:88) and ZC38,245 (SEQ ID NO:89) as primers. CTLL-2 is a mouse cytotoxic T lymphocyte cell line (ATCC No. TIB-214). This PCR reaction was run as follows: 1 cycle at 95° C. for 1 minute, 30 cycles at 95° C. for 15 seconds, 68° C. for 3 minutes, then 68° C. for 10 minutes; 4° C. soak. The PCR reaction used approximately 0.5 ng. of cDNA, 20 pmoles of each oligonucleotide, and 1 μl. of Advantage II polymerase mix (ClonTech). About 6% of the PCR product was used as a template in a new PCR reaction, as above, except with oligonucleotides ZC38,239 (SEQ ID NO:88) and ZC38,238 (SEQ ID NO:90). This PCR reaction was run as follows: 30 cycles at 94° C. for 45 seconds, 65° C. for 45 seconds, 72° C. for 1 minute, then 72° C. for 7 minutes; 10° C. soak. Most of the PCR reaction was loaded on a 1.0% agarose gel and the predominant band at approximately 360 bp was excised, the DNA fragment was eluted, and DNA sequencing was performed.

The sequence of the mouse zcytor17 polynucleotide is shown in SEQ ID NO:56 and the corresponding amino acid sequence shown in SEQ ID NO:57. In addition, a truncated soluble form of the mouse zcytor17 polynucleotide is shown in SEQ ID NO:92 and the corresponding amino acid sequence shown in SEQ ID NO:93.

Example 22

Tissue Distribution of Human zcytor17 in Tissue Panels Using PCR

A panel of cDNAs from murine tissues was screened for mouse zcytor17 expression using PCR. The panel was made in-house and contained 94 marathon cDNA and cDNA samples from various normal and cancerous murine tissues and cell lines are shown in Table 7, below. The cDNAs came from in-house libraries or marathon cDNAs from in-house RNA preps, Clontech RNA, or Invitrogen RNA. The mouse marathon cDNAs were made using the marathon-Ready™ kit (Clontech, Palo Alto, Calif.) and QC tested with mouse transferrin receptor primers ZC10,651 (SEQ ID NO:79) and ZC10,565 (SEQ ID NO:80) and then diluted based on the intensity of the transferrin band. To assure quality of the amplified library samples in the panel, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo: ZC14,063 (SEQ ID NO:7) and 3' alpha tubulin specific oligo primer ZC17,574 (SEQ ID NO:26) or 3' G3PDH specific oligo primer ZC17,600 (SEQ ID NO:27); and (3) a sample was sent to sequencing to check for possible ribosomal or mitochondrial DNA contamination. The panel was set up in a 96-well format that included a mouse genomic DNA (Clontech, Palo Alto, Calif.) positive control sample. Each well contained approximately 0.2-100 pg/μl of cDNA. The PCR was set up using oligos ZC38,065 (SEQ ID NO:77) and ZC38,068 (SEQ ID NO:78), TaKaRa Ex Taq™ (TAKARA Shuzo Co LTD, Biomedicals Group, Japan), and Rediload dye (Research Genetics, Inc., Huntsville, Ala.). The amplification was carried out as follows: 1 cycle at 94° C. for 5 minutes; 5 cycles of 94° C. for 30 seconds, 68° C. for 30 seconds; 35 cycles of 94° C. for 30 seconds, 56° C. for 30 seconds and 72° C. for 30 seconds, followed by 1 cycle at 72° C. for 5 minutes. About 10 μl of the PCR reaction product was subjected to standard Agarose gel electrophoresis using a 4% agarose gel. The correct predicted DNA fragment size was observed in brain, CD90+ cells, dendritic, embryo, MEWt#2, Tuvak-prostate cell line, salivary gland, skin and testis.

The DNA fragment for skin and testis were excised and purified using a Gel Extraction Kit (Qiagen, Chatsworth, Calif.) according to manufacturer's instructions. Fragments were confirmed by sequencing to show that they were indeed mouse zcytor17.

TABLE 7

| Tissue/Cell line | # samples |
|---|---|
| 229 | 1 |
| 7F2 | 1 |
| Adipocytes-Amplified | 1 |
| aTC1.9 | 1 |
| Brain | 4 |
| CCC4 | 1 |
| CD90+ Amplified | 1 |
| OC10B | 1 |
| Dentritic | 1 |
| Embyro | 1 |
| Heart | 2 |
| Kidney | 3 |
| Liver | 2 |
| Lung | 2 |
| MEWt#2 | 1 |
| P388D1 | 1 |
| Pancreas | 1 |
| Placenta | 2 |
| Jakotay-Prostate Cell Line | 1 |
| Nelix-Prostate Cell Line | 1 |
| Paris-Prostate Cell Line | 1 |
| Torres-Prostate Cell Line | 1 |
| Tuvak-Prostate Cell Line | 1 |
| Salivary Gland | 2 |
| Skeletal Muscle | 1 |
| Skin | 2 |
| Small Intestine | 1 |
| Smooth Muscle | 2 |
| Spleen | 2 |
| Stomach | 1 |
| Testis | 3 |
| Thymus | 1 |

Example 23

Zcytor17 Expression in Various Tissues Using Real-Time Quantitative RT/PCR

A. Primers and Probes for Quantitative RT-PCR-

Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by 5' nuclease activity of Taq polymerase which releases the reporter dye from the probe resulting in an increase in fluorescent emission.

The primers and probes used for real-time quantitative RT-PCR analyses of Zcytor17 expression were designed using the primer design software Primer Express™ (PE Applied Biosystems, Foster City, Calif.). Primers for human Zcytor17 were designed spanning an intron-exon junction to eliminate amplification of genomic DNA. The forward primer, ZC37,877 (SEQ ID NO:81) and the reverse primer, ZC37,876 (SEQ ID NO:82) were used in a PCR reaction (below) at about 300 nM concentration to synthesize a 73 bp product. The corresponding Zcytor17 TaqMan® probe, designated ZG37,776 (SEQ ID NO:83) was synthesized and labeled by PE Applied Biosystems. The ZG37,776 probe was labeled at the 5'end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

As a control to test the integrity and quality of RNA samples tested, all RNA samples (below) were screened for rRNA using a primer and probe set ordered from PE Applied Biosystems (cat#4304483). The kit contains the rRNA forward primer (SEQ ID NO:84), the rRNA reverse primer (SEQ ID NO:85), and the rRNA TaqMan® probe (SEQ ID NO:86) The rRNA probe was labeled at the 5' end with a reporter fluorescent dye VIC (PE Applied Biosystems) and at the 3' end with the quencher fluorescent dye TAMRA (PE Applied Biosystems). The rRNA results also serve as an endogenous control and allow for the normalization of the Zcytor17 mRNA expression results seen in the test samples.

Blood was drawn from several anonymous donors and PBMC's isolated. Various immune cell subsets (CD3+, CD4+, CD8+, CD14+, CD19+, CD45RA, CD45RO and CD56+) were then isolated using Microbeads and the Magnetic Cell Separation System from Miltenyi Biotec. RNA was prepared from all of the CD45RA, CD45RO and CD56+ populations in their resting state using an RNeasy Midiprep™ Kit (Qiagen, Valencia, Calif.) as per manufacturer's instruction. The CD3+, CD4+, and CD8+ populations were activated using 200 ng/ml plate-bound anti-CD3 antibody and 5 ug/ml soluble anti-CD28 antibody and cells were collected for RNA isolation at 0, 4 and 16 hours. The CD19+ samples were isolated from human tonsil and activated with 0.5 ug/ml ionomycin and 10 ng/ml PMA. Cells were then collected at 0, 4 hours and 24 hours and RNA isolated. Human CD14+ monocytes were activated with either 0.1 ug/ml LPS or 1.0 ug/ml LPS for 20 hours. Resting and activated cells were then collected and RNA isolated. In addition, RNA was isolated from resting and activated (10.0 ug/ml LPS) human monocyte cell lines HL-60, THP-1 (ATCC No. TIB-202) and U937. THP-1 RNA was used as a control because it was shown to express Zcytor17 by Northern Blot (Example 3).

B. Real-time Quantitative RT-PCR-

Relative levels of Zcytor17 mRNA were determined by analyzing total RNA samples using the one-step RT-PCR method (PE Applied Biosystems). Total RNA from Zcytor17 expressing THP-1 cells was isolated by standard methods and used to generate a standard curve used for quantitation. The curve consisted of 10-fold serial dilutions ranging from 0.25-0.00025 ng/0 for the rRNA screen and 250-0.25 ng/μl for the Zcytor17 screen with each standard curve point analyzed in triplicate. The total RNA samples from the human cells were also analyzed in triplicate for human Zcytor17 transcript levels and for levels of rRNA as an endogenous control. In a total volume of 25 μl, each RNA sample was subjected to a One-Step RT-PCR reaction containing: approximately 50 ng of total RNA in buffer A (50 mM KCL, 10 mM Tris-HCL); the internal standard dye, carboxy-x-rhodamine (ROX)); appropriate primers (approximately 50 nM rRNA primers (SEQ ID NO:84 and SEQ ID NO:85) for the rRNA samples; and approximately 300 nM ZC37,877 (SEQ ID NO:81) and ZC22,276 (SEQ ID NO:87) primers for Zcytor17 samples); the appropriate probe (approximately 50 nM rRNA TaqMan® probe (SEQ ID NO:86) for rRNA samples, approximately 100 nM ZG37,776 (SEQ ID NO:83) probe for Zcytor17 samples); 5.5 mM $MgCl_2$; 300 μM each d-CTP, d-ATP, and d-GTP and 600 μM of d-UTP; MuLV reverse transcriptase (0.25 U/μl); AmpliTaq™ Gold DNA polymerase (0.025 U/μl) (PE Applied Biosystems); and RNase Inhibitor (0.4 U/μl) (PE Applied Biosystems). PCR thermal cycling conditions were as follows: an initial reverse transcription (RT) step of one cycle at 48° C. for 30 minutes; followed by an AmpliTaq Gold™ (PE Applied Biosystems) activation step of one cycle at 95° C. for 10 minutes; followed by 40 cycles of amplification at 95° C. for 15 seconds and 60° C. for 1 minute.

Relative Zcytor17 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The rRNA measurements were used to normalize the Zcytor17 levels. Three experiments were done testing the aforementioned. Data shown in Tables 8 and 9 below are expressed as a ratio of Zcytor17 mRNA to rRNA.

TABLE 8

| Sample | Resting | 4 hr Stimulation | 16 hr Stimulation | 24 hr Stimulation |
|---|---|---|---|---|
| CD19+ PBMC | 0.06 | | | |
| CD19+ Tonsil | 0.003 | 0.02 | | .002 |
| CD3+ | 0 | 0.72 | 0.51 | |
| CD45RA | 0 | | | |
| CD45RO | 0 | | | |
| CD56+ NK | 0 | | | |

TABLE 9

| Sample | Resting | 4 hr Stimulation | 16 hr Stimulation |
|---|---|---|---|
| CD4+ T Cell | 0.003 | 0.55 | 0.41 |
| CD8+ T Cell | 0.00 | 0.37 | 0.13 |

While there was some expression of Zcytor17 message in resting CD19+ B cells from the peripheral blood, both resting and activated CD19+ B cells isolated from human tonsil showed only minimal expression. Resting memory T cells (CD45RO), naïve T Cells (CD45RA) and NK cells (CD56+) all tested negative for Zcytor17 message. However, in CD3+ T cells, Zcytor17 message underwent a dramatic upregulation to a ratio of about 0.72 following a 4 hour activation with anti-CD3 and anti-CD28 antibodies. The ratio then dropped to 0.51 by 16 hours post-activation. Prior to activation, no Zcytor17 mRNA was detected in resting CD3+ T cells.

The results revealed that Zcytor17 was not present in appreciable levels in resting CD4+ or CD8+ T cell subsets. Following a 4 hour activation with anti-CD3 and anti-CD28 antibodies there appears to be a substantial upregulation of Zcytor17 message produced in both CD4+ and CD8+ T cell subsets. By 16 hours post-activation, the Zcytor17 mRNA had decreased to 0.41 in CD4+ T cells and 0.13 in CD8+ T cells.

There was extremely high expression of Zcytor17 message in both the resting and activated monocyte cell lines THP-1 and U937. The activated U937's have the highest level of expression. HL-60's, a pre-differentiated monocyte cell line, showed a decrease in Zcytor17 mRNA expression upon activation. These results support expression results done by northern blot (Example 2). There was very little expression of Zcytor17 message in primary CD14+ monocytes both resting and activated with 0.1 ug/ml and 1.0 ug/ml LPS.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a monoclonal antibody or antigen binding fragment thereof that specifically binds to a fragment of a polypeptide consisting of amino acid residues 20-732 of SEQ ID NO:2, wherein said fragment consists of amino acid residues 228-519 of SEQ ID NO:2.

2. The isolated polynucleotide of claim 1, wherein the antigen binding fragment is a Fab, a $F(ab')_2$ or a single chain antibody.

3. The isolated polynucleotide of claim 1, wherein the monoclonal antibody or antigen binding fragment is chimeric.

4. The isolated polynucleotide of claim 1, wherein the monoclonal antibody or antigen binding fragment is humanized.

5. The isolated polynucleotide of claim 1, wherein the monoclonal antibody or antigen binding fragment is human.

* * * * *

SEQUENCE LISTING

```
<160> NUMBER OF SEQ ID NOS: 93

<210> SEQ ID NO 1
<211> LENGTH: 2402
<212> TYPE: DNA
<213> ORGANISM: Homo sapiens
<220> FEATURE:
<221> NAME/KEY: CDS
<222> LOCATION: (171)...(2366)

<400> SEQUENCE: 1

ggcacgaggt gtgtgtgcag tatgaaaatt gagacaggaa ggcagagtgt cagcttgttc      60

cacctcagct gggaatgtgc atcaggcaac tcaagttttt caccacggca tgtgtctgtg     120

aatgtccgca aaacattctc tctccccagc cttcatgtgt taacctgggg atg atg        176
                                                       Met Met
                                                         1

tgg acc tgg gca ctg tgg atg ctc ccc tca ctc tgc aaa ttc agc ctg       224
Trp Thr Trp Ala Leu Trp Met Leu Pro Ser Leu Cys Lys Phe Ser Leu
        5                  10                  15

gca gct ctg cca gct aag cct gag aac att tcc tgt gtc tac tac tat       272
Ala Ala Leu Pro Ala Lys Pro Glu Asn Ile Ser Cys Val Tyr Tyr Tyr
    20                  25                  30

agg aaa aat tta acc tgc act tgg agt cca gga aag gaa acc agt tat       320
Arg Lys Asn Leu Thr Cys Thr Trp Ser Pro Gly Lys Glu Thr Ser Tyr
 35                  40                  45                  50

acc cag tac aca gtt aag aga act tac gct ttt gga gaa aaa cat gat       368
Thr Gln Tyr Thr Val Lys Arg Thr Tyr Ala Phe Gly Glu Lys His Asp
                 55                  60                  65

aat tgt aca acc aat agt tct aca agt gaa aat cgt gct tcg tgc tct       416
Asn Cys Thr Thr Asn Ser Ser Thr Ser Glu Asn Arg Ala Ser Cys Ser
             70                  75                  80

ttt ttc ctt cca aga ata acg atc cca gat aat tat acc att gag gtg       464
Phe Phe Leu Pro Arg Ile Thr Ile Pro Asp Asn Tyr Thr Ile Glu Val
         85                  90                  95

gaa gct gaa aat gga gat ggt gta att aaa tct cat atg aca tac tgg       512
Glu Ala Glu Asn Gly Asp Gly Val Ile Lys Ser His Met Thr Tyr Trp
    100                 105                 110

aga tta gag aac ata gcg aaa act gaa cca cct aag att ttc cgt gtg       560
Arg Leu Glu Asn Ile Ala Lys Thr Glu Pro Pro Lys Ile Phe Arg Val
115                 120                 125                 130

aaa cca gtt ttg ggc atc aaa cga atg att caa att gaa tgg ata aag       608
Lys Pro Val Leu Gly Ile Lys Arg Met Ile Gln Ile Glu Trp Ile Lys
                135                 140                 145
```

```
cct gag ttg gcg cct gtt tca tct gat tta aaa tac aca ctt cga ttc      656
Pro Glu Leu Ala Pro Val Ser Ser Asp Leu Lys Tyr Thr Leu Arg Phe
            150                 155                 160

agg aca gtc aac agt acc agc tgg atg gaa gtc aac ttc gct aag aac      704
Arg Thr Val Asn Ser Thr Ser Trp Met Glu Val Asn Phe Ala Lys Asn
        165                 170                 175

cgt aag gat aaa aac caa acg tac aac ctc acg ggg ctg cag cct ttt      752
Arg Lys Asp Lys Asn Gln Thr Tyr Asn Leu Thr Gly Leu Gln Pro Phe
    180                 185                 190

aca gaa tat gtc ata gct ctg cga tgt gcg gtc aag gag tca aag ttc      800
Thr Glu Tyr Val Ile Ala Leu Arg Cys Ala Val Lys Glu Ser Lys Phe
195                 200                 205                 210

tgg agt gac tgg agc caa gaa aaa atg gga atg act gag gaa gaa gct      848
Trp Ser Asp Trp Ser Gln Glu Lys Met Gly Met Thr Glu Glu Glu Ala
                215                 220                 225

cca tgt ggc ctg gaa ctg tgg aga gtc ctg aaa cca gct gag gcg gat      896
Pro Cys Gly Leu Glu Leu Trp Arg Val Leu Lys Pro Ala Glu Ala Asp
            230                 235                 240

gga aga agg cca gtg cgg ttg tta tgg aag aag gca aga gga gcc cca      944
Gly Arg Arg Pro Val Arg Leu Leu Trp Lys Lys Ala Arg Gly Ala Pro
        245                 250                 255

gtc cta gag aaa aca ctt ggc tac aac ata tgg tac tat cca gaa agc      992
Val Leu Glu Lys Thr Leu Gly Tyr Asn Ile Trp Tyr Tyr Pro Glu Ser
    260                 265                 270

aac act aac ctc aca gaa aca atg aac act act aac cag cag ctt gaa     1040
Asn Thr Asn Leu Thr Glu Thr Met Asn Thr Thr Asn Gln Gln Leu Glu
275                 280                 285                 290

ctg cat ctg gga ggc gag agc ttt tgg gtg tct atg att tct tat aat     1088
Leu His Leu Gly Gly Glu Ser Phe Trp Val Ser Met Ile Ser Tyr Asn
                295                 300                 305

tct ctt ggg aag tct cca gtg gcc acc ctg agg att cca gct att caa     1136
Ser Leu Gly Lys Ser Pro Val Ala Thr Leu Arg Ile Pro Ala Ile Gln
            310                 315                 320

gaa aaa tca ttt cag tgc att gag gtc atg cag gcc tgc gtt gct gag     1184
Glu Lys Ser Phe Gln Cys Ile Glu Val Met Gln Ala Cys Val Ala Glu
        325                 330                 335

gac cag cta gtg gtg aag tgg caa agc tct gct cta gac gtg aac act     1232
Asp Gln Leu Val Val Lys Trp Gln Ser Ser Ala Leu Asp Val Asn Thr
    340                 345                 350

tgg atg att gaa tgg ttt ccg gat gtg gac tca gag ccc acc acc ctt     1280
Trp Met Ile Glu Trp Phe Pro Asp Val Asp Ser Glu Pro Thr Thr Leu
355                 360                 365                 370

tcc tgg gaa tct gtg tct cag gcc acg aac tgg acg atc cag caa gat     1328
Ser Trp Glu Ser Val Ser Gln Ala Thr Asn Trp Thr Ile Gln Gln Asp
                375                 380                 385

aaa tta aaa cct ttc tgg tgc tat aac atc tct gtg tat cca atg ttg     1376
Lys Leu Lys Pro Phe Trp Cys Tyr Asn Ile Ser Val Tyr Pro Met Leu
            390                 395                 400

cat gac aaa gtt ggc gag cca tat tcc atc cag gct tat gcc aaa gaa     1424
His Asp Lys Val Gly Glu Pro Tyr Ser Ile Gln Ala Tyr Ala Lys Glu
        405                 410                 415

ggc gtt cca tca gaa ggt cct gag acc aag gtg gag aac att ggc gtg     1472
Gly Val Pro Ser Glu Gly Pro Glu Thr Lys Val Glu Asn Ile Gly Val
    420                 425                 430

aag acg gtc acg atc aca tgg aaa gag att ccc aag agt gag aga aag     1520
Lys Thr Val Thr Ile Thr Trp Lys Glu Ile Pro Lys Ser Glu Arg Lys
435                 440                 445                 450

ggt atc atc tgc aac tac acc atc ttt tac caa gct gaa ggt gga aaa     1568
Gly Ile Ile Cys Asn Tyr Thr Ile Phe Tyr Gln Ala Glu Gly Gly Lys
                455                 460                 465
```

```
gga ttc tcc aag aca gtc aat tcc agc atc ttg cag tac ggc ctg gag     1616
Gly Phe Ser Lys Thr Val Asn Ser Ser Ile Leu Gln Tyr Gly Leu Glu
            470                 475                 480

tcc ctg aaa cga aag acc tct tac att gtt cag gtc atg gcc agc acc     1664
Ser Leu Lys Arg Lys Thr Ser Tyr Ile Val Gln Val Met Ala Ser Thr
        485                 490                 495

agt gct ggg gga acc aac ggg acc agc ata aat ttc aag aca ttg tca     1712
Ser Ala Gly Gly Thr Asn Gly Thr Ser Ile Asn Phe Lys Thr Leu Ser
    500                 505                 510

ttc agt gtc ttt gag att atc ctc ata act tct ctg att ggt gga ggc     1760
Phe Ser Val Phe Glu Ile Ile Leu Ile Thr Ser Leu Ile Gly Gly Gly
515                 520                 525                 530

ctt ctt att ctc att atc ctg aca gtg gca tat ggt ctc aaa aaa ccc     1808
Leu Leu Ile Leu Ile Ile Leu Thr Val Ala Tyr Gly Leu Lys Lys Pro
                535                 540                 545

aac aaa ttg act cat ctg tgt tgg ccc acc gtt ccc aac cct gct gaa     1856
Asn Lys Leu Thr His Leu Cys Trp Pro Thr Val Pro Asn Pro Ala Glu
            550                 555                 560

agt agt ata gcc aca tgg cat gga gat gat ttc aag gat aag cta aac     1904
Ser Ser Ile Ala Thr Trp His Gly Asp Asp Phe Lys Asp Lys Leu Asn
        565                 570                 575

ctg aag gag tct gat gac tct gtg aac aca gaa gac agg atc tta aaa     1952
Leu Lys Glu Ser Asp Asp Ser Val Asn Thr Glu Asp Arg Ile Leu Lys
    580                 585                 590

cca tgt tcc acc ccc agt gac aag ttg gtg att gac aag ttg gtg gtg     2000
Pro Cys Ser Thr Pro Ser Asp Lys Leu Val Ile Asp Lys Leu Val Val
595                 600                 605                 610

aac ttt ggg aat gtt ctg caa gaa att ttc aca gat gaa gcc aga acg     2048
Asn Phe Gly Asn Val Leu Gln Glu Ile Phe Thr Asp Glu Ala Arg Thr
                615                 620                 625

ggt cag gaa aac aat tta gga ggg gaa aag aat ggg tat gtg acc tgc     2096
Gly Gln Glu Asn Asn Leu Gly Gly Glu Lys Asn Gly Tyr Val Thr Cys
            630                 635                 640

ccc ttc agg cct gat tgt ccc ctg ggg aaa agt ttt gag gag ctc cca     2144
Pro Phe Arg Pro Asp Cys Pro Leu Gly Lys Ser Phe Glu Glu Leu Pro
        645                 650                 655

gtt tca cct gag att ccg ccc aga aaa tcc caa tac cta cgt tcg agg     2192
Val Ser Pro Glu Ile Pro Pro Arg Lys Ser Gln Tyr Leu Arg Ser Arg
    660                 665                 670

atg cca gag ggg acc cgc cca gaa gcc aaa gag cag ctt ctc ttt tct     2240
Met Pro Glu Gly Thr Arg Pro Glu Ala Lys Glu Gln Leu Leu Phe Ser
675                 680                 685                 690

ggt caa agt tta gta cca gat cat ctg tgt gag gaa gga gcc cca aat     2288
Gly Gln Ser Leu Val Pro Asp His Leu Cys Glu Glu Gly Ala Pro Asn
                695                 700                 705

cca tat ttg aaa aat tca gtg aca gcc agg gaa ttt ctt gtg tct gaa     2336
Pro Tyr Leu Lys Asn Ser Val Thr Ala Arg Glu Phe Leu Val Ser Glu
            710                 715                 720

aaa ctt cca gag cac acc aag gga gaa gtc taaatgcgac catagcatga       2386
Lys Leu Pro Glu His Thr Lys Gly Glu Val
        725                 730

gaccctcggg gcctca                                                   2402
```

<210> SEQ ID NO 2
<211> LENGTH: 732
<212> TYPE: PRT
<213> ORGANISM: Homo sapiens

<400> SEQUENCE: 2

```
Met Met Trp Thr Trp Ala Leu Trp Met Leu Pro Ser Leu Cys Lys Phe
```

-continued

```
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430
```

```
Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
    610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
    690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
                725                 730


<210> SEQ ID NO 3
<211> LENGTH: 5
<212> TYPE: PRT
<213> ORGANISM: Artificial Sequence
<220> FEATURE:
<223> OTHER INFORMATION: WSXWS peptide motif
<220> FEATURE:
<221> NAME/KEY: VARIANT
<222> LOCATION: (1)...(5)
<223> OTHER INFORMATION: Xaa = Any Amino Acid

<400> SEQUENCE: 3

Trp Ser Xaa Trp Ser
 1               5


<210> SEQ ID NO 4
<211> LENGTH: 2196
<212> TYPE: DNA
<213> ORGANISM: Artificial Sequence
<220> FEATURE:
```

```
<223> OTHER INFORMATION: Degenerate polynucleotide sequence of SEQ ID
      NO:2
<220> FEATURE:
<221> NAME/KEY: misc_feature
<222> LOCATION: (1)...(2196)
<223> OTHER INFORMATION: n = A,T,C or G

<400> SEQUENCE: 4

atgatgtgga cntgggcnyt ntggatgytn ccnwsnytnt gyaarttyws nytngcngcn     60

ytnccngcna arccngaraa yathwsntgy gtntaytayt aymgnaaraa yytnacntgy    120

acntggwsnc cnggnaarga racnwsntay acncartaya cngtnaarmg nacntaygcn    180

ttyggngara arcaygayaa ytgyacnacn aaywsnwsna cnwsngaraa ymgngcnwsn    240

tgywsnttyt tyytnccnmg nathacnath ccngayaayt ayacnathga rgtngargcn    300

garaayggng ayggngtnat haarwsncay atgacntayt ggmgnytnga raayathgcn    360

aaracngarc cnccnaarat httymgngtn aarccngtny tnggnathaa rmgnatgath    420

carathgart ggathaarcc ngarytngcn ccngtnwsnw sngayytnaa rtayacnytn    480

mgnttymgna cngtnaayws nacnwsntgg atggargtna ayttygcnaa raaymgnaar    540

gayaaraayc aracntayaa yytnacnggn ytncarccnt tyacngarta ygtnathgcn    600

ytnmgntgyg cngtnaarga rwsnaartty tggwsngayt ggwsncarga raaratgggn    660

atgacngarg argargcncc ntgyggnytn garytntggm gngtnytnaa rccngcngar    720

gcngayggnm gnmgnccngt nmgnytnytn tggaaraarg cnmgnggngc nccngtnytn    780

garaaracny tnggntayaa yathtggtay tayccngarw snaayacnaa yytnacngar    840

acnatgaaya cnacnaayca rcarytngar ytncayytng gnggngarws nttytgggtn    900

wsnatgathw sntayaayws nytnggnaar wsnccngtng cnacnytnmg nathccngcn    960

athcargara arwsnttyca rtgyathgar gtnatgcarg cntgygtngc ngargaycar   1020

ytngtngtna artggcarws nwsngcnytn gaygtnaaya cntggatgat hgartggtty   1080

ccngaygtng aywsngarcc nacnacnytn wsntgggarw sngtnwsnca rgcnacnaay   1140

tggacnathc arcargayaa rytnaarccn ttytggtgyt ayaayathws ngtntayccn   1200

atgytncayg ayaargtngg ngarccntay wsnathcarg cntaygcnaa rgarggngtn   1260

ccnwsngarg gnccngarac naargtngar aayathggng tnaaracngt nacnathacn   1320

tggaargara thccnaarws ngarmgnaar ggnathatht gyaaytayac nathttytay   1380

cargcngarg gnggnaargg nttywsnaar acngtnaayw snwsnathyt ncartayggn   1440

ytngarwsny tnaarmgnaa racnwsntay athgtncarg tnatggcnws nacnwsngcn   1500

ggnggnacna ayggnacnws nathaaytty aaracnytnw snttywsngt nttygarath   1560

athytnatha cnwsnytnat hggnggnggn ytnytnathy tnathathyt nacngtngcn   1620

tayggnytna araarccnaa yaarytnacn cayytntgyt ggccnacngt nccnaayccn   1680

gcngarwsnw snathgcnac ntggcayggn gaygayttya argayaaryt naayytnaar   1740

garwsngayg aywsngtnaa yacngargay mgnathytna arccntgyws nacnccnwsn   1800

gayaarytng tnathgayaa rytngtngtn aayttyggna aygtnytnca rgarathtty   1860

acngaygarg cnmgnacngg ncargaraay aayytnggng gngaraaraa yggntaygtn   1920

acntgyccnt tymgnccnga ytgyccnytn ggnaarwsnt tygargaryt nccngtnwsn   1980

ccngarathc cnccnmgnaa rwsncartay ytnmgnwsnm gnatgccnga rggnacnmgn   2040

ccngargcna argarcaryt nytnttywsn ggncarwsny tngtnccnga ycayytntgy   2100

gargarggng cnccnaaycc ntayytnaar aaywsngtna cngcnmgnga rttyytngtn   2160
```

wsngaraary tnccngarca yacnaarggn gargtn 2196

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer ZC12701

<400> SEQUENCE: 5
tcagaggtaa ctcccgttgc 20

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide primer ZC27898

<400> SEQUENCE: 6
ttagcgcaga gcagccatac acc 23

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 7
caccagacat aatagctgac agact 25

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer ZC27899

<400> SEQUENCE: 8
ccagaacttt gactccttga ccg 23

<210> SEQ ID NO 9
<211> LENGTH: 765
<212> TYPE: DNA
<213> ORGANISM: Homo sapiens

<400> SEQUENCE: 9
tgtgtgtgca gtatgaaaat tgagacagga aggcagagtg tcagcttgtt ccacctcagc 60
tgggaatgtg catcaggcaa ctcaagtttt tcaccacggc atgtgtctgt gaatgtccgc 120
aaaacattct ctctccccag ccttcatgtg ttaacctggg gatgatgtgg acctgggcac 180
tgtggatgct cccttcactc tgcaaattca gcctggcagc tctgccagct aagcctgaga 240
acatttcctg tgtctactac tataggaaaa atttaacctg cacttggagt ccaggaaagg 300
aaaccagtta tacccagtac acagttaaga gaacttacgc ttttggagaa aaacatgata 360
attgtacaac caatagttct acaagtgaaa atcgtgcttc gtgctctttt ttccttccaa 420
gaataacgat cccagataat tataccattg aggtggaagc tgaaaatgga gatggtgtaa 480
ttaaatctca tatgacatac tggagattag agaacatagc gaaaactgaa ccacctaaga 540
ttttccgtgt gaaaccagtt ttgggcatca aacgaatgat tcaaattgaa tggataaagc 600
ctgagttggc gcctgtttca tctgatttaa aatacacact tcgattcagg acagtcaaca 660
gtaccagctg gatggaagtc aacttcgcta agaaccgtaa ggataaaaac caaacgtaca 720
acctcacggg gctgcagcct tttacagaat atgtcatagc tctgc 765

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer ZC28481

<400> SEQUENCE: 10
gaatggataa agcctgagtt ggcg 24

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer ZC6346

<400> SEQUENCE: 11
ggccccttgc tccataccac 20

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer ZC28480

<400> SEQUENCE: 12
cgattcagga cagtcaacag tacc 24

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer ZC26405

<400> SEQUENCE: 13
tatagaagga cacctagtca gaca 24

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer ZC27895

<400> SEQUENCE: 14
gaagtcaact tcgctaagaa ccg 23

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer ZC5020

<400> SEQUENCE: 15
cactggagtg gcaacttcca g 21

<210> SEQ ID NO 16
<211> LENGTH: 1853

<212> TYPE: DNA
<213> ORGANISM: Homo sapiens

<400> SEQUENCE: 16

```
agtcaacttc gctaagaacc gtaaggataa aaaccaaacg tacaacctca cggggctgca     60
gccttttaca gaatatgtca tagctctgcg atgtgcggtc aaggagtcaa agttctggag    120
tgactggagc caagaaaaaa tgggaatgac tgaggaagaa gctccatgtg gcctggaact    180
gtggggagtc ctgaaaccag ctgaggcgga tggaagaagg ccagtgcggt tgttatggaa    240
gaaggcaaga ggagccccag tcctagagaa aacacttggc tacaacatat ggtactatcc    300
agaaagcaac actaacctca cagaaacaat gaacactact aaccagcagc ttgaactgca    360
tctgggaggc gagagctttt gggtgtctat gatttcttat aattctcttg ggaagtctcc    420
agtggccacc ctgaggattc cagctattca agaaaaatca tttcagtgca ttgaggtcat    480
gcaggcctgc gttgctgagg accagctagt ggtgaagtgg caaagctctg ctctagacgt    540
gaacacttgg atgattgaat ggtttccgga tgtggactca gagcccacca ccctttcctg    600
ggaatctgtg tctcaggcca cgaactggac gatccagcaa gataaattaa aacctttctg    660
gtgctataac atctctgtgt atccaatgtt gcatgacaaa gttggcgagc catattccat    720
ccaggcttat gccaaagaag gcgttccatc agaaggtcct gagaccaagg tggagaacat    780
tggcgtgaag acggtcacga tcacatggag agagattccc aagagtgaga gaaagggtat    840
catctgcaac tacaccatct ttaccaagc tgaaggtgga aaaggattct ccaagacagt    900
caattccagc atcttgcagt acggcctgga gtccctgaaa cgaaagacct cttacattgt    960
tcaggtcatg gccagcacca gtgctggggg aaccaacggg accagcataa atttcaagac   1020
attgtcattc agtgtctttg agattatcct cataacttct ctgattggtg gaggccttct   1080
tattctcatt atcctgacag tggcatatgg tctcaaaaaa cccaacaaat tgactcatct   1140
gtgttggccc accgttccca accctgctga gagtagtata gccacacggc atggagatga   1200
tttcaaggat aagctaaacc tgaaggagtc tgatgactct gtgaacacag aagacaggat   1260
cttaaaacca tgttccaccc ccagtgacaa gttggtgatt gacaagttgg tggtgaactt   1320
tgggaatgtt ctgcaagaaa ttttcacaga tgaagccaga acgggtcagg aaaacaattt   1380
aggaggggaa aagaatggga ctagaattct gtcttcctgc ccaacttcaa tataagtgtg   1440
gactaaaatg cgagaaaggt gtcctgtggt ctatgcaaat tagaaaggac atgcagagtt   1500
ttccaactag gaagactgaa tctgtggccc caagagaacc atctctgaag actgggtatg   1560
tggtcttttc cacacatgga ccacctacgg atgtaatctg taatgcatgt gcatgagaag   1620
tctgttatta agtagagtgt gaaaacatgg ttatggtaat aggaacagct tttaaaatgc   1680
ttttgcattt gggcctttca tacaaaaaag ccataatacc attttcatgt aatgctatac   1740
ttctatacta ttttcatgta atactatact tctatactat tttcatgtaa tactatactt   1800
ctatactatt ttcatgtaat actatacttc tatattaaag ttttacccac tca           1853
```

<210> SEQ ID NO 17
<211> LENGTH: 1299
<212> TYPE: DNA
<213> ORGANISM: Homo sapiens
<220> FEATURE:
<221> NAME/KEY: CDS
<222> LOCATION: (162)...(1133)

<400> SEQUENCE: 17

```
tgtgtgtgca gtatgaaaat tgagacagga aggcagagtg tcagcttgtt ccacctcagc     60
```

```
tgggaatgtg catcaggcaa ctcaagtttt tcaccacggc atgtgtctgt gaatgtccgc    120

aaaacattct ctctccccag ccttcatgtg ttaacctggg g atg atg tgg acc tgg    176
                                              Met Met Trp Thr Trp
                                              1               5

gca ctg tgg atg ctc ccc tca ctc tgc aaa ttc agc ctg gca gct ctg      224
Ala Leu Trp Met Leu Pro Ser Leu Cys Lys Phe Ser Leu Ala Ala Leu
                10                  15                  20

cca gct aag cct gag aac att tcc tgt gtc tac tac tat agg aaa aat      272
Pro Ala Lys Pro Glu Asn Ile Ser Cys Val Tyr Tyr Tyr Arg Lys Asn
            25                  30                  35

tta acc tgc act tgg agt cca gga aag gaa acc agt tat acc cag tac      320
Leu Thr Cys Thr Trp Ser Pro Gly Lys Glu Thr Ser Tyr Thr Gln Tyr
        40                  45                  50

aca gtt aag aga act tac gct ttt gga gaa aaa cat gat aat tgt aca      368
Thr Val Lys Arg Thr Tyr Ala Phe Gly Glu Lys His Asp Asn Cys Thr
    55                  60                  65

acc aat agt tct aca agt gaa aat cgt gct tcg tgc tct ttt ttc ctt      416
Thr Asn Ser Ser Thr Ser Glu Asn Arg Ala Ser Cys Ser Phe Phe Leu
70                  75                  80                  85

cca aga ata acg atc cca gat aat tat acc att gag gtg gaa gct gaa      464
Pro Arg Ile Thr Ile Pro Asp Asn Tyr Thr Ile Glu Val Glu Ala Glu
                90                  95                  100

aat gga gat ggt gta att aaa tct cat atg aca tac tgg aga tta gag      512
Asn Gly Asp Gly Val Ile Lys Ser His Met Thr Tyr Trp Arg Leu Glu
            105                 110                 115

aac ata gcg aaa act gaa cca cct aag att ttc cgt gtg aaa cca gtt      560
Asn Ile Ala Lys Thr Glu Pro Pro Lys Ile Phe Arg Val Lys Pro Val
        120                 125                 130

ttg ggc atc aaa cga atg att caa att gaa tgg ata aag cct gag ttg      608
Leu Gly Ile Lys Arg Met Ile Gln Ile Glu Trp Ile Lys Pro Glu Leu
    135                 140                 145

gcg cct gtt tca tct gat tta aaa tac aca ctt cga ttc agg aca gtc      656
Ala Pro Val Ser Ser Asp Leu Lys Tyr Thr Leu Arg Phe Arg Thr Val
150                 155                 160                 165

aac agt acc agc tgg atg gaa gtc aac ttc gct aag aac cgt aag gat      704
Asn Ser Thr Ser Trp Met Glu Val Asn Phe Ala Lys Asn Arg Lys Asp
                170                 175                 180

aaa aac caa acg tac aac ctc acg ggg ctg cag cct ttt aca gaa tat      752
Lys Asn Gln Thr Tyr Asn Leu Thr Gly Leu Gln Pro Phe Thr Glu Tyr
            185                 190                 195

gtc ata gct ctg cga tgt gcg gtc aag gag tca aag ttc tgg agt gac      800
Val Ile Ala Leu Arg Cys Ala Val Lys Glu Ser Lys Phe Trp Ser Asp
        200                 205                 210

tgg agc caa gaa aaa atg gga atg act gag gaa gaa gct cca tgt ggc      848
Trp Ser Gln Glu Lys Met Gly Met Thr Glu Glu Glu Ala Pro Cys Gly
    215                 220                 225

ctg gaa ctg tgg aga gtc ctg aaa cca gct gag gcg gat gga aga agg      896
Leu Glu Leu Trp Arg Val Leu Lys Pro Ala Glu Ala Asp Gly Arg Arg
230                 235                 240                 245

cca gtg cgg ttg tta tgg aag aag gca aga gga gcc cca gtc cta gag      944
Pro Val Arg Leu Leu Trp Lys Lys Ala Arg Gly Ala Pro Val Leu Glu
                250                 255                 260

aaa aca ctt ggc tac aac ata tgg tac tat cca gaa agc aac act aac      992
Lys Thr Leu Gly Tyr Asn Ile Trp Tyr Tyr Pro Glu Ser Asn Thr Asn
            265                 270                 275

ctc aca gaa aca atg aac act act aac cag cag ctt gaa ctg cat ctg     1040
Leu Thr Glu Thr Met Asn Thr Thr Asn Gln Gln Leu Glu Leu His Leu
        280                 285                 290

gga ggc gag agc ttt tgg gtg tct atg att tct tat aat tct ctt ggg     1088
Gly Gly Glu Ser Phe Trp Val Ser Met Ile Ser Tyr Asn Ser Leu Gly
```

```
    295                 300                 305

aag tct cca gtg gcc acc ctg agg att cca gct att caa gaa aaa         1133
Lys Ser Pro Val Ala Thr Leu Arg Ile Pro Ala Ile Gln Glu Lys
310                 315                 320

tagaaacttt acagatgcta gtcccagaca taaaagaaaa taatgttctg gatgtgcacg   1193

atggctcacg cctgtaatcc cagcactttg aggccaagac gggtggatcg ctgagttcag   1253

gagttcaaga caagtccagg caacatagtg aaaccttgtt tctaca                  1299


<210> SEQ ID NO 18
<211> LENGTH: 324
<212> TYPE: PRT
<213> ORGANISM: Homo sapiens

<400> SEQUENCE: 18

Met Met Trp Thr Trp Ala Leu Trp Met Leu Pro Ser Leu Cys Lys Phe
 1               5                  10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320
```

```
Ile Gln Glu Lys


<210> SEQ ID NO 19
<211> LENGTH: 23
<212> TYPE: DNA
<213> ORGANISM: Artificial Sequence
<220> FEATURE:
<223> OTHER INFORMATION: Oligonucleotide primer ZC27897

<400> SEQUENCE: 19

caagctactt ctctggtgta tgg                                             23


<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer ZC28521

<400> SEQUENCE: 20

gagtagtagc tccaggattc ac                                              22


<210> SEQ ID NO 21
<211> LENGTH: 1476
<212> TYPE: DNA
<213> ORGANISM: Homo sapiens
<220> FEATURE:
<221> NAME/KEY: CDS
<222> LOCATION: (162)...(878)

<400> SEQUENCE: 21

tgtgtgtgca gtatgaaaat tgagacagga aggcagagtg tcagcttgtt ccacctcagc     60

tgggaatgtg catcaggcaa ctcaagtttt tcaccacggc atgtgtctgt gaatgtccgc    120

aaaacattct ctctccccag ccttcatgtg ttaacctggg g atg atg tgg acc tgg    176
                                              Met Met Trp Thr Trp
                                               1               5

gca ctg tgg atg ctc ccc tca ctc tgc aaa ttc agc ctg gca gct ctg      224
Ala Leu Trp Met Leu Pro Ser Leu Cys Lys Phe Ser Leu Ala Ala Leu
                 10                  15                  20

cca gct aag cct gag aac att tcc tgt gtc tac tac tat agg aaa aat      272
Pro Ala Lys Pro Glu Asn Ile Ser Cys Val Tyr Tyr Tyr Arg Lys Asn
             25                  30                  35

tta acc tgc act tgg agt cca gga aag gaa acc agt tat acc cag tac      320
Leu Thr Cys Thr Trp Ser Pro Gly Lys Glu Thr Ser Tyr Thr Gln Tyr
         40                  45                  50

aca gtt aag aga act tac gct ttt gga gaa aaa cat gat aat tgt aca      368
Thr Val Lys Arg Thr Tyr Ala Phe Gly Glu Lys His Asp Asn Cys Thr
     55                  60                  65

acc aat agt tct aca agt gaa aat cgt gct tcg tgc tct ttt ttc ctt      416
Thr Asn Ser Ser Thr Ser Glu Asn Arg Ala Ser Cys Ser Phe Phe Leu
 70                  75                  80                  85

cca aga ata acg atc cca gat aat tat acc att gag gtg gaa gct gaa      464
Pro Arg Ile Thr Ile Pro Asp Asn Tyr Thr Ile Glu Val Glu Ala Glu
                 90                  95                 100

aat gga gat ggt gta att aaa tct cat atg aca tac tgg aga tta gag      512
Asn Gly Asp Gly Val Ile Lys Ser His Met Thr Tyr Trp Arg Leu Glu
            105                 110                 115

aac ata gcg aaa act gaa cca cct aag att ttc cgt gtg aaa cca gtt      560
Asn Ile Ala Lys Thr Glu Pro Pro Lys Ile Phe Arg Val Lys Pro Val
        120                 125                 130

ttg ggc atc aaa cga atg att caa att gaa tgg ata aag cct gag ttg      608
Leu Gly Ile Lys Arg Met Ile Gln Ile Glu Trp Ile Lys Pro Glu Leu
    135                 140                 145
```

```
gcg cct gtt tca tct gat tta aaa tac aca ctt cga ttc agg aca gtc      656
Ala Pro Val Ser Ser Asp Leu Lys Tyr Thr Leu Arg Phe Arg Thr Val
150                 155                 160                 165

aac agt acc agc tgg atg gaa gtc aac ttc gct aag aac cgt aag gat      704
Asn Ser Thr Ser Trp Met Glu Val Asn Phe Ala Lys Asn Arg Lys Asp
                170                 175                 180

aaa aac caa acg tac aac ctc acg ggg ctg cag cct ttt aca gaa tat      752
Lys Asn Gln Thr Tyr Asn Leu Thr Gly Leu Gln Pro Phe Thr Glu Tyr
            185                 190                 195

gtc ata gct ctg cga tgt gcg gtc aag gag tca aag ttc tgg agt gac      800
Val Ile Ala Leu Arg Cys Ala Val Lys Glu Ser Lys Phe Trp Ser Asp
        200                 205                 210

tgg agc caa gaa aaa atg gga atg act gag gaa gaa ggc aag cta ctc      848
Trp Ser Gln Glu Lys Met Gly Met Thr Glu Glu Glu Gly Lys Leu Leu
    215                 220                 225

cct gcg att ccc gtc ctg tct gct ctg gtg tagggctgct ttgggctaga        898
Pro Ala Ile Pro Val Leu Ser Ala Leu Val
230                 235

cttggtgggg tttgtcacca cctggttggg aatcatggaa tctcatgacc ccaggggccc    958

cctgtaccat cgagagtgag cctgcacaac tttgtgcccc aaaggcaaag gatcacattt   1018

taatactcat gaggttctta tactatacat gaaagggtat catatcattt gttttgtttt   1078

gttttgtttt tgagatggag tcttactctg tcacccagga tggagtgcag tgatgtgatc   1138

tcggctcact gccaccacca cctcccgagt tcaagcaatt cttgtgcctc agcctcccaa   1198

gtagctggga ttacaggggc ccacgaccat gcccggttga tttttgtatt tttagtagag   1258

aagggatatc accatgttgg ctaggctagt cttgaactcc tgacctcagg taatctgccc   1318

accttgacct cccaaagtgt tgggattaca ggcgtgagcc actgtgcccc gccagtatca   1378

tatcatctga aggtatcctg tgataaatta aagatacata ttgtgaatcc tggagctact   1438

actcaaaaaa taaataaagg tgtaactaat acaattta                           1476


<210> SEQ ID NO 22
<211> LENGTH: 239
<212> TYPE: PRT
<213> ORGANISM: Homo sapiens

<400> SEQUENCE: 22

Met Met Trp Thr Trp Ala Leu Trp Met Leu Pro Ser Leu Cys Lys Phe
 1               5                  10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140
```

```
Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Gly Lys Leu Leu Pro Ala Ile Pro Val Leu Ser Ala Leu Val
225                 230                 235
```

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer ZC28575

<400> SEQUENCE: 23
ccaggaaagg aaaccagtta tacc 24

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide primer ZC27899

<400> SEQUENCE: 24
ccagaacttt gactccttga ccg 23

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 25
caccagacat aatagctgac agact 25

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 26
ggtrttgctc agcatgcaca c 21

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 27
catgtaggcc atgaggtcca ccac 24

<210> SEQ ID NO 28

<211> LENGTH: 25
<212> TYPE: DNA
<213> ORGANISM: Artificial Sequence
<220> FEATURE:
<223> OTHER INFORMATION: Oligonucleotide primer ZC26358

<400> SEQUENCE: 28
aaaaccaaac gtacaacctc acggg 25

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer ZC26359

<400> SEQUENCE: 29
gagcagccat acaccagagc agaca 25

<210> SEQ ID NO 30
<211> LENGTH: 33
<212> TYPE: DNA
<213> ORGANISM: Artificial Sequence
<220> FEATURE:
<223> OTHER INFORMATION: Oligonucleotide primer ZC17212

<400> SEQUENCE: 30
ggggaattcg aagccatgcc ctcttgggcc ctc 33

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide primer ZC17313

<400> SEQUENCE: 31
caccctgcga agccttagca gcagtaggcc 30

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide primer ZC17205

<400> SEQUENCE: 32
cccgccccat ccccgtggat caccttggtg 30

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide primer ZC17206

<400> SEQUENCE: 33
gggtctagac cttcagggct gctgccaata 30

<210> SEQ ID NO 34
<211> LENGTH: 6
<212> TYPE: PRT
<213> ORGANISM: Artificial Sequence
<220> FEATURE:
<223> OTHER INFORMATION: Glu-Glu Tag peptide

<400> SEQUENCE: 34

```
Glu Tyr Met Pro Met Glu
 1               5


<210> SEQ ID NO 35
<211> LENGTH: 8
<212> TYPE: PRT
<213> ORGANISM: Artificial Sequence
<220> FEATURE:
<223> OTHER INFORMATION: FLAG tag peptide sequence

<400> SEQUENCE: 35

Asp Tyr Lys Asp Asp Asp Asp Lys
 1               5


<210> SEQ ID NO 36
<211> LENGTH: 699
<212> TYPE: DNA
<213> ORGANISM: Homo sapiens

<400> SEQUENCE: 36

gagcccagat cttcagacaa aactcacaca tgcccaccgt gcccagcacc tgaagccgag     60

ggggcaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc catcctccat cgagaaaacc    360

atctccaaag ccaaagggca gccccgagaa ccacaggtgt acaccctgcc cccatcccgg    420

gatgagctga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctacagca agctcaccgt ggacaagagc    600

aggtggcagc aggggaacgt cttctcatgc tccgtgatgc atgaggctct gcacaaccac    660

tacacgcaga agagcctctc cctgtctccg ggtaaataa                           699


<210> SEQ ID NO 37
<211> LENGTH: 990
<212> TYPE: DNA
<213> ORGANISM: Homo sapiens
<220> FEATURE:
<221> NAME/KEY: CDS
<222> LOCATION: (1)...(990)

<400> SEQUENCE: 37

gct agc acc aag ggc cca tcg gtc ttc ccc ctg gca ccc tcc tcc aag       48
Ala Ser Thr Lys Gly Pro Ser Val Phe Pro Leu Ala Pro Ser Ser Lys
 1               5                  10                  15

agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
             20                  25                  30

ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
         35                  40                  45

ggc gtg cac acc ttc ccg gct gtc cta cag tcc tca gga ctc tac tcc      192
Gly Val His Thr Phe Pro Ala Val Leu Gln Ser Ser Gly Leu Tyr Ser
     50                  55                  60

ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65                  70                  75                  80

tac atc tgc aac gtg aat cac aag ccc agc aac acc aag gtg gac aag      288
```

```
Tyr Ile Cys Asn Val Asn His Lys Pro Ser Asn Thr Lys Val Asp Lys
                 85                  90                  95

aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110

cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125

aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140

gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160

tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175

gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190

cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205

aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220

cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240

ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255

ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270

aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285

ctc tac agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300

gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320

cag aag agc ctc tcc ctg tct ccg ggt aaa                              990
Gln Lys Ser Leu Ser Leu Ser Pro Gly Lys
                325                 330


<210> SEQ ID NO 38
<211> LENGTH: 330
<212> TYPE: PRT
<213> ORGANISM: Homo sapiens

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 39

act gtg gct gca cca tct gtc ttc atc ttc ccg cca tct gat gag cag       48
Thr Val Ala Ala Pro Ser Val Phe Ile Phe Pro Pro Ser Asp Glu Gln
 1               5                  10                  15

ttg aaa tct ggt acc gcc tct gtt gtg tgc ctg ctg aat aac ttc tat       96
Leu Lys Ser Gly Thr Ala Ser Val Val Cys Leu Leu Asn Asn Phe Tyr
            20                  25                  30

ccc aga gag gcc aaa gta cag tgg aag gtg gat aac gcc ctc caa tcg      144
Pro Arg Glu Ala Lys Val Gln Trp Lys Val Asp Asn Ala Leu Gln Ser
        35                  40                  45

ggt aac tcc cag gag agt gtc aca gag cag gac agc aag gac agc acc      192
Gly Asn Ser Gln Glu Ser Val Thr Glu Gln Asp Ser Lys Asp Ser Thr
     50                  55                  60
```

```
tac agc ctc agc agc acc ctg acg ctg agc aaa gca gac tac gag aaa      240
Tyr Ser Leu Ser Ser Thr Leu Thr Leu Ser Lys Ala Asp Tyr Glu Lys
 65                  70                  75                  80

cac aaa gtc tac gcc tgc gaa gtc acc cat cag ggc ctg agc tcg ccc      288
His Lys Val Tyr Ala Cys Glu Val Thr His Gln Gly Leu Ser Ser Pro
                85                  90                  95

gtc aca aag agc ttc aac agg gga gag tgt tag                          321
Val Thr Lys Ser Phe Asn Arg Gly Glu Cys  *
            100                 105
```

<210> SEQ ID NO 40
<211> LENGTH: 106
<212> TYPE: PRT
<213> ORGANISM: Homo sapiens

<400> SEQUENCE: 40

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 41
<211> LENGTH: 8
<212> TYPE: DNA
<213> ORGANISM: Artificial Sequence
<220> FEATURE:
<223> OTHER INFORMATION: Oligonucleotide primer ZC11440

<400> SEQUENCE: 41

```
aattgaga                                                                8
```

<210> SEQ ID NO 42
<211> LENGTH: 8
<212> TYPE: DNA
<213> ORGANISM: Artificial Sequence
<220> FEATURE:
<223> OTHER INFORMATION: Oligonucleotide primer ZC11441

<400> SEQUENCE: 42

```
cgcgtctc                                                                8
```

<210> SEQ ID NO 43
<211> LENGTH: 100
<212> TYPE: DNA
<213> ORGANISM: Artificial Sequence
<220> FEATURE:
<223> OTHER INFORMATION: Oligonucleotide primer ZC12749

<400> SEQUENCE: 43

```
gtaccttccc gtaaatccct ccccttcccg gaattacacc cgcgtatttc ccagaaaagg      60

aactgtagat ttctaggaat tcaatccttg gccacgcgtc                           100
```

<210> SEQ ID NO 44
<211> LENGTH: 100
<212> TYPE: DNA
<213> ORGANISM: Artificial Sequence
<220> FEATURE:
<223> OTHER INFORMATION: Oligonucleotide primer ZC12748

<400> SEQUENCE: 44

```
tcgagacgcg tggccaagga ttgaattcct agaaatctac agttcctttt ctgggaaata     60

cgcgggtgta attccgggaa ggggagggat ttacgggaag                          100
```

<210> SEQ ID NO 45
<211> LENGTH: 2529
<212> TYPE: DNA
<213> ORGANISM: Homo sapiens
<220> FEATURE:
<221> NAME/KEY: CDS
<222> LOCATION: (162)...(2108)

<400> SEQUENCE: 45

```
tgtgtgtgca gtatgaaaat tgagacagga aggcagagtg tcagcttgtt ccacctcagc     60

tgggaatgtg catcaggcaa ctcaagtttt tcaccacggc atgtgtctgt gaatgtccgc    120

aaaacattct ctctccccag ccttcatgtg ttaacctggg g atg atg tgg acc tgg    176
                                           Met Met Trp Thr Trp
                                            1               5

gca ctg tgg atg ctc ccc tca ctc tgc aaa ttc agc ctg gca gct ctg      224
Ala Leu Trp Met Leu Pro Ser Leu Cys Lys Phe Ser Leu Ala Ala Leu
                10                  15                  20

cca gct aag cct gag aac att tcc tgt gtc tac tac tat agg aaa aat      272
Pro Ala Lys Pro Glu Asn Ile Ser Cys Val Tyr Tyr Tyr Arg Lys Asn
            25                  30                  35

tta acc tgc act tgg agt cca gga aag gaa acc agt tat acc cag tac      320
Leu Thr Cys Thr Trp Ser Pro Gly Lys Glu Thr Ser Tyr Thr Gln Tyr
        40                  45                  50

aca gtt aag aga act tac gct ttt gga gaa aaa cat gat aat tgt aca      368
Thr Val Lys Arg Thr Tyr Ala Phe Gly Glu Lys His Asp Asn Cys Thr
    55                  60                  65

acc aat agt tct aca agt gaa aat cgt gct tcg tgc tct ttt ttc ctt      416
Thr Asn Ser Ser Thr Ser Glu Asn Arg Ala Ser Cys Ser Phe Phe Leu
 70                  75                  80                  85

cca aga ata acg atc cca gat aat tat acc att gag gtg gaa gct gaa      464
Pro Arg Ile Thr Ile Pro Asp Asn Tyr Thr Ile Glu Val Glu Ala Glu
                90                  95                  100

aat gga gat ggt gta att aaa tct cat atg aca tac tgg aga tta gag      512
Asn Gly Asp Gly Val Ile Lys Ser His Met Thr Tyr Trp Arg Leu Glu
            105                 110                 115

aac ata gcg aaa act gaa cca cct aag att ttc cgt gtg aaa cca gtt      560
Asn Ile Ala Lys Thr Glu Pro Pro Lys Ile Phe Arg Val Lys Pro Val
        120                 125                 130

ttg ggc atc aaa cga atg att caa att gaa tgg ata aag cct gag ttg      608
Leu Gly Ile Lys Arg Met Ile Gln Ile Glu Trp Ile Lys Pro Glu Leu
    135                 140                 145

gcg cct gtt tca tct gat tta aaa tac aca ctt cga ttc agg aca gtc      656
Ala Pro Val Ser Ser Asp Leu Lys Tyr Thr Leu Arg Phe Arg Thr Val
150                 155                 160                 165

aac agt acc agc tgg atg gaa gtc aac ttc gct aag aac cgt aag gat      704
Asn Ser Thr Ser Trp Met Glu Val Asn Phe Ala Lys Asn Arg Lys Asp
                170                 175                 180

aaa aac caa acg tac aac ctc acg ggg ctg cag cct ttt aca gaa tat      752
Lys Asn Gln Thr Tyr Asn Leu Thr Gly Leu Gln Pro Phe Thr Glu Tyr
            185                 190                 195
```

```
gtc ata gct ctg cga tgt gcg gtc aag gag tca aag ttc tgg agt gac      800
Val Ile Ala Leu Arg Cys Ala Val Lys Glu Ser Lys Phe Trp Ser Asp
        200                 205                 210

tgg agc caa gaa aaa atg gga atg act gag gaa gaa gct cca tgt ggc      848
Trp Ser Gln Glu Lys Met Gly Met Thr Glu Glu Glu Ala Pro Cys Gly
    215                 220                 225

ctg gaa ctg tgg aga gtc ctg aaa cca gct gag gcg gat gga aga agg      896
Leu Glu Leu Trp Arg Val Leu Lys Pro Ala Glu Ala Asp Gly Arg Arg
230                 235                 240                 245

cca gtg cgg ttg tta tgg aag aag gca aga gga gcc cca gtc cta gag      944
Pro Val Arg Leu Leu Trp Lys Lys Ala Arg Gly Ala Pro Val Leu Glu
                250                 255                 260

aaa aca ctt ggc tac aac ata tgg tac tat cca gaa agc aac act aac      992
Lys Thr Leu Gly Tyr Asn Ile Trp Tyr Tyr Pro Glu Ser Asn Thr Asn
            265                 270                 275

ctc aca gaa aca atg aac act act aac cag cag ctt gaa ctg cat ctg     1040
Leu Thr Glu Thr Met Asn Thr Thr Asn Gln Gln Leu Glu Leu His Leu
        280                 285                 290

gga ggc gag agc ttt tgg gtg tct atg att tct tat aat tct ctt ggg     1088
Gly Gly Glu Ser Phe Trp Val Ser Met Ile Ser Tyr Asn Ser Leu Gly
    295                 300                 305

aag tct cca gtg gcc acc ctg agg att cca gct att caa gaa aaa tca     1136
Lys Ser Pro Val Ala Thr Leu Arg Ile Pro Ala Ile Gln Glu Lys Ser
310                 315                 320                 325

ttt cag tgc att gag gtc atg cag gcc tgc gtt gct gag gac cag cta     1184
Phe Gln Cys Ile Glu Val Met Gln Ala Cys Val Ala Glu Asp Gln Leu
                330                 335                 340

gtg gtg aag tgg caa agc tct gct cta gac gtg aac act tgg atg att     1232
Val Val Lys Trp Gln Ser Ser Ala Leu Asp Val Asn Thr Trp Met Ile
            345                 350                 355

gaa tgg ttt ccg gat gtg gac tca gag ccc acc acc ctt tcc tgg gaa     1280
Glu Trp Phe Pro Asp Val Asp Ser Glu Pro Thr Thr Leu Ser Trp Glu
        360                 365                 370

tct gtg tct cag gcc acg aac tgg acg atc cag caa gat aaa tta aaa     1328
Ser Val Ser Gln Ala Thr Asn Trp Thr Ile Gln Gln Asp Lys Leu Lys
    375                 380                 385

cct ttc tgg tgc tat aac atc tct gtg tat cca atg ttg cat gac aaa     1376
Pro Phe Trp Cys Tyr Asn Ile Ser Val Tyr Pro Met Leu His Asp Lys
390                 395                 400                 405

gtt ggc gag cca tat tcc atc cag gct tat gcc aaa gaa ggc gtt cca     1424
Val Gly Glu Pro Tyr Ser Ile Gln Ala Tyr Ala Lys Glu Gly Val Pro
                410                 415                 420

tca gaa ggt cct gag acc aag gtg gag aac att ggc gtg aag acg gtc     1472
Ser Glu Gly Pro Glu Thr Lys Val Glu Asn Ile Gly Val Lys Thr Val
            425                 430                 435

acg atc aca tgg aaa gag att ccc aag agt gag aga aag ggt atc atc     1520
Thr Ile Thr Trp Lys Glu Ile Pro Lys Ser Glu Arg Lys Gly Ile Ile
        440                 445                 450

tgc aac tac acc atc ttt tac caa gct gaa ggt gga aaa gga ttc tcc     1568
Cys Asn Tyr Thr Ile Phe Tyr Gln Ala Glu Gly Gly Lys Gly Phe Ser
    455                 460                 465

aag aca gtc aat tcc agc atc ttg cag tac ggc ctg gag tcc ctg aaa     1616
Lys Thr Val Asn Ser Ser Ile Leu Gln Tyr Gly Leu Glu Ser Leu Lys
470                 475                 480                 485

cga aag acc tct tac att gtt cag gtc atg gcc agc acc agt gct ggg     1664
Arg Lys Thr Ser Tyr Ile Val Gln Val Met Ala Ser Thr Ser Ala Gly
                490                 495                 500

gga acc aac ggg acc agc ata aat ttc aag aca ttg tca ttc agt gtc     1712
Gly Thr Asn Gly Thr Ser Ile Asn Phe Lys Thr Leu Ser Phe Ser Val
            505                 510                 515
```

```
ttt gag att atc ctc ata act tct ctg att ggt gga ggc ctt ctt att     1760
Phe Glu Ile Ile Leu Ile Thr Ser Leu Ile Gly Gly Gly Leu Leu Ile
        520                 525                 530

ctc att atc ctg aca gtg gca tat ggt ctc aaa aaa ccc aac aaa ttg     1808
Leu Ile Ile Leu Thr Val Ala Tyr Gly Leu Lys Lys Pro Asn Lys Leu
    535                 540                 545

act cat ctg tgt tgg ccc acc gtt ccc aac cct gct gaa agt agt ata     1856
Thr His Leu Cys Trp Pro Thr Val Pro Asn Pro Ala Glu Ser Ser Ile
550                 555                 560                 565

gcc aca tgg cat gga gat gat ttc aag gat aag cta aac ctg aag gag     1904
Ala Thr Trp His Gly Asp Asp Phe Lys Asp Lys Leu Asn Leu Lys Glu
                570                 575                 580

tct gat gac tct gtg aac aca gaa gac agg atc tta aaa cca tgt tcc     1952
Ser Asp Asp Ser Val Asn Thr Glu Asp Arg Ile Leu Lys Pro Cys Ser
            585                 590                 595

acc ccc agt gac aag ttg gtg att gac aag ttg gtg gtg aac ttt ggg     2000
Thr Pro Ser Asp Lys Leu Val Ile Asp Lys Leu Val Val Asn Phe Gly
        600                 605                 610

aat gtt ctg caa gaa att ttc aca gat gaa gcc aga acg ggt cag gaa     2048
Asn Val Leu Gln Glu Ile Phe Thr Asp Glu Ala Arg Thr Gly Gln Glu
    615                 620                 625

aac aat tta gga ggg gaa aag aat ggg act aga att ctg tct tcc tgc     2096
Asn Asn Leu Gly Gly Glu Lys Asn Gly Thr Arg Ile Leu Ser Ser Cys
630                 635                 640                 645

cca act tca ata taagtgtgga ctaaaatgcg agaaaggtgt cctgtggtct         2148
Pro Thr Ser Ile

atgcaaatta gaaaggacat gcagagtttt ccaactagga agactgaatc tgtggcccca   2208

agagaaccat ctctgaagac tgggtatgtg gtcttttcca cacatggacc acctacggat   2268

gcaatctgta atgcatgtgc atgagaagtc tgttattaag tagagtgtga aaacatggtt   2328

atggtaatag gaacagcttt taaaatgctt ttgtatttgg gcctttcata caaaaaagcc   2388

ataataccat tttcatgtaa tgctatactt ctatactatt ttcatgtaat actatacttc   2448

tatactattt tcatgtaata ctatacttct atactatttt catgtaatac tatacttcta   2508

tattaaagtt ttacccactc a                                              2529


<210> SEQ ID NO 46
<211> LENGTH: 649
<212> TYPE: PRT
<213> ORGANISM: Homo sapiens

<400> SEQUENCE: 46

Met Met Trp Thr Trp Ala Leu Trp Met Leu Pro Ser Leu Cys Lys Phe
 1               5                  10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
```

```
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540
```

Lys Pro Asn Lys Leu Thr His Leu Cys Trp Pro Thr Val Pro Asn Pro
545 550 555 560

Ala Glu Ser Ser Ile Ala Thr Trp His Gly Asp Asp Phe Lys Asp Lys
565 570 575

Leu Asn Leu Lys Glu Ser Asp Asp Ser Val Asn Thr Glu Asp Arg Ile
580 585 590

Leu Lys Pro Cys Ser Thr Pro Ser Asp Lys Leu Val Ile Asp Lys Leu
595 600 605

Val Val Asn Phe Gly Asn Val Leu Gln Glu Ile Phe Thr Asp Glu Ala
610 615 620

Arg Thr Gly Gln Glu Asn Asn Leu Gly Gly Glu Lys Asn Gly Thr Arg
625 630 635 640

Ile Leu Ser Ser Cys Pro Thr Ser Ile
645

<210> SEQ ID NO 47
<211> LENGTH: 1947
<212> TYPE: DNA
<213> ORGANISM: Artificial Sequence
<220> FEATURE:
<223> OTHER INFORMATION: Degenerate polynucleotide sequence of SEQ ID NO:46
<220> FEATURE:
<221> NAME/KEY: misc_feature
<222> LOCATION: (1)...(1947)
<223> OTHER INFORMATION: n = A,T,C or G

<400> SEQUENCE: 47
atgatgtgga cntgggcnyt ntggatgytn ccnwsnytnt gyaarttyws nytngcngcn 60
ytnccngcna arccngaraa yathwsntgy gtntaytayt aymgnaaraa yytnacntgy 120
acntggwsnc cnggnaarga racnwsntay acncartaya cngtnaarmg nacntaygcn 180
ttyggngara arcaygayaa ytgyacnacn aaywsnwsna cnwsngaraa ymgngcnwsn 240
tgywsnttyt tyytnccnmg nathacnath ccngayaayt ayacnathga rgtngargcn 300
garaayggng ayggngtnat haarwsncay atgacntayt ggmgnytnga raayathgcn 360
aaracngarc cnccnaarat httymgngtn aarccngtny tnggnathaa rmgnatgath 420
carathgart ggathaarcc ngarytngcn ccngtnwsnw sngayytnaa rtayacnytn 480
mgnttymgna cngtnaayws nacnwsntgg atggargtna ayttygcnaa raaymgnaar 540
gayaaraayc aracntayaa yytnacnggn ytncarccnt tyacngarta ygtnathgcn 600
ytnmgntgyg cngtnaarga rwsnaartty tggwsngayt ggwsncarga raaratgggn 660
atgacngarg argargcncc ntgyggnytn garytntggm gngtnytnaa rccngcngar 720
gcngayggnm gnmgnccngt nmgnytnytn tggaaraarg cnmgnggngc nccngtnytn 780
garaaracny tnggntayaa yathtggtay tayccngarw snaayacnaa yytnacngar 840
acnatgaaya cnacnaayca rcarytngar ytncayytng gnggngarws nttytgggtn 900
wsnatgathw sntayaayws nytnggnaar wsnccngtng cnacnytnmg nathccngcn 960
athcargara arwsnttyca rtgyathgar gtnatgcarg cntgygtngc ngargaycar 1020
ytngtngtna artggcarws nwsngcnytn gaygtnaaya cntggatgat hgartggtty 1080
ccngaygtng aywsngarcc nacnacnytn wsntgggarw sngtnwsnca rgcnacnaay 1140
tggacnathc arcargayaa rytnaarccn ttytggtgyt ayaayathws ngtntayccn 1200
atgytncayg ayaargtngg ngarccntay wsnathcarg cntaygcnaa rgarggngtn 1260
ccnwsngarg gnccngarac naargtngar aayathggng tnaaracngt nacnathacn 1320
tggaargara thccnaarws ngarmgnaar ggnathatht gyaaytayac nathttytay 1380
cargcngarg gnggnaargg nttywsnaar acngtnaayw snwsnathyt ncartayggn 1440
ytngarwsny tnaarmgnaa racnwsntay athgtncarg tnatggcnws nacnwsngcn 1500
ggnggnacna ayggnacnws nathaaytty aaracnytnw snttywsngt nttygarath 1560
athytnatha cnwsnytnat hggnggnggn ytnytnathy tnathathyt nacngtngcn 1620
tayggnytna araarccnaa yaarytnacn cayytntgyt ggccnacngt nccnaayccn 1680
gcngarwsnw snathgcnac ntggcayggn gaygayttya argayaaryt naayytnaar 1740
garwsngayg aywsngtnaa yacngargay mgnathytna arccntgyws nacnccnwsn 1800
gayaarytng tnathgayaa rytngtngtn aayttyggna aygtnytnca rgarathtty 1860
acngaygarg cnmgnacngg ncargaraay aayytnggng gngaraaraa yggnacnmgn 1920
athytnwsnw sntgyccnac nwsnath 1947

<210> SEQ ID NO 48
<211> LENGTH: 32
<212> TYPE: PRT
<213> ORGANISM: Homo sapiens

<400> SEQUENCE: 48

Met Cys Ile Arg Gln Leu Lys Phe Phe Thr Thr Ala Cys Val Cys Glu
1 5 10 15

Cys Pro Gln Asn Ile Leu Ser Pro Gln Pro Ser Cys Val Asn Leu Gly
20 25 30

<210> SEQ ID NO 49
<211> LENGTH: 23
<212> TYPE: DNA
<213> ORGANISM: Artificial Sequence
<220> FEATURE:
<223> OTHER INFORMATION: Oligonucloetide primer ZC21195

<400> SEQUENCE: 49
gaggagacca taaccccga cag 23

<210> SEQ ID NO 50
<211> LENGTH: 23
<212> TYPE: DNA
<213> ORGANISM: Artificial Sequence
<220> FEATURE:
<223> OTHER INFORMATION: Oligonucloetide primer ZC21196

<400> SEQUENCE: 50
catagctccc accacacgat ttt 23

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide primer ZC27900

<400> SEQUENCE: 51
gccccgtgag gttgtacgtt tgg 23

<210> SEQ ID NO 52
<211> LENGTH: 13
<212> TYPE: PRT
<213> ORGANISM: Homo sapiens

<400> SEQUENCE: 52

```
Met Lys Leu Ser Pro Gln Pro Ser Cys Val Asn Leu Gly
 1               5                  10


<210> SEQ ID NO 53
<211> LENGTH: 2903
<212> TYPE: DNA
<213> ORGANISM: Homo sapiens
<220> FEATURE:
<221> NAME/KEY: CDS
<222> LOCATION: (497)...(2482)

<400> SEQUENCE: 53

tgaaaagaca tgtgtgtgca gtatgaaaat tgagacagga aggcagagtg tcagcttgtt      60

ccacctcagc tgggaatgtg catcaggcaa ctcaagtttt tcaccacggc atgtgtctgt     120

gaatgtccgc aaaacattag tttcactctt gtcgccaggt tggagtacaa tggcacgatc     180

ttggctcact gcaacctctg cctcccgggt tcaagcgatt ctcctgcctc agcctcccga     240

gtagctggga ttacagttaa caataatgca atccatttcc cagcataagt gggtaagtgc     300

cactttgact tgggctgggc ttaaaagcac aagaaaagct cgcagacaat cagagtggaa     360

acactcccac atcttagtgt ggataaatta aagtccagat tgttcttcct gtcctgactt     420

gtgctgtggg aggtggagtt gcctttgatg caaatccttt gagccagcag aacatctgtg     480

gaacatcccc tgatac atg aag ctc tct ccc cag cct tca tgt gtt aac ctg     532
                  Met Lys Leu Ser Pro Gln Pro Ser Cys Val Asn Leu
                   1               5                  10

ggg atg atg tgg acc tgg gca ctg tgg atg ctc cct tca ctc tgc aaa      580
Gly Met Met Trp Thr Trp Ala Leu Trp Met Leu Pro Ser Leu Cys Lys
         15                  20                  25

ttc agc ctg gca gct ctg cca gct aag cct gag aac att tcc tgt gtc      628
Phe Ser Leu Ala Ala Leu Pro Ala Lys Pro Glu Asn Ile Ser Cys Val
     30                  35                  40

tac tac tat agg aaa aat tta acc tgc act tgg agt cca gga aag gaa      676
Tyr Tyr Tyr Arg Lys Asn Leu Thr Cys Thr Trp Ser Pro Gly Lys Glu
 45                  50                  55                  60

acc agt tat acc cag tac aca gtt aag aga act tac gct ttt gga gaa      724
Thr Ser Tyr Thr Gln Tyr Thr Val Lys Arg Thr Tyr Ala Phe Gly Glu
                 65                  70                  75

aaa cat gat aat tgt aca acc aat agt tct aca agt gaa aat cgt gct      772
Lys His Asp Asn Cys Thr Thr Asn Ser Ser Thr Ser Glu Asn Arg Ala
             80                  85                  90

tcg tgc tct ttt ttc ctt cca aga ata acg atc cca gat aat tat acc      820
Ser Cys Ser Phe Phe Leu Pro Arg Ile Thr Ile Pro Asp Asn Tyr Thr
         95                 100                 105

att gag gtg gaa gct gaa aat gga gat ggt gta att aaa tct cat atg      868
Ile Glu Val Glu Ala Glu Asn Gly Asp Gly Val Ile Lys Ser His Met
    110                 115                 120

aca tac tgg aga tta gag aac ata gcg aaa act gaa cca cct aag att      916
Thr Tyr Trp Arg Leu Glu Asn Ile Ala Lys Thr Glu Pro Pro Lys Ile
125                 130                 135                 140

ttc cgt gtg aaa cca gtt ttg ggc atc aaa cga atg att caa att gaa      964
Phe Arg Val Lys Pro Val Leu Gly Ile Lys Arg Met Ile Gln Ile Glu
                145                 150                 155

tgg ata aag cct gag ttg gcg cct gtt tca tct gat tta aaa tac aca     1012
Trp Ile Lys Pro Glu Leu Ala Pro Val Ser Ser Asp Leu Lys Tyr Thr
            160                 165                 170

ctt cga ttc agg aca gtc aac agt acc agc tgg atg gaa gtc aac ttc     1060
Leu Arg Phe Arg Thr Val Asn Ser Thr Ser Trp Met Glu Val Asn Phe
        175                 180                 185

gct aag aac cgt aag gat aaa aac caa acg tac aac ctc acg ggg ctg     1108
Ala Lys Asn Arg Lys Asp Lys Asn Gln Thr Tyr Asn Leu Thr Gly Leu
```

```
    190                 195                 200

cag cct ttt aca gaa tat gtc ata gct ctg cga tgt gcg gtc aag gag     1156
Gln Pro Phe Thr Glu Tyr Val Ile Ala Leu Arg Cys Ala Val Lys Glu
205                 210                 215                 220

tca aag ttc tgg agt gac tgg agc caa gaa aaa atg gga atg act gag     1204
Ser Lys Phe Trp Ser Asp Trp Ser Gln Glu Lys Met Gly Met Thr Glu
                225                 230                 235

gaa gaa gct cca tgt ggc ctg gaa ctg tgg aga gtc ctg aaa cca gct     1252
Glu Glu Ala Pro Cys Gly Leu Glu Leu Trp Arg Val Leu Lys Pro Ala
            240                 245                 250

gag gcg gat gga aga agg cca gtg cgg ttg tta tgg aag aag gca aga     1300
Glu Ala Asp Gly Arg Arg Pro Val Arg Leu Leu Trp Lys Lys Ala Arg
        255                 260                 265

gga gcc cca gtc cta gag aaa aca ctt ggc tac aac ata tgg tac tat     1348
Gly Ala Pro Val Leu Glu Lys Thr Leu Gly Tyr Asn Ile Trp Tyr Tyr
    270                 275                 280

cca gaa agc aac act aac ctc aca gaa aca atg aac act act aac cag     1396
Pro Glu Ser Asn Thr Asn Leu Thr Glu Thr Met Asn Thr Thr Asn Gln
285                 290                 295                 300

cag ctt gaa ctg cat ctg gga ggc gag agc ttt tgg gtg tct atg att     1444
Gln Leu Glu Leu His Leu Gly Gly Glu Ser Phe Trp Val Ser Met Ile
                305                 310                 315

tct tat aat tct ctt ggg aag tct cca gtg gcc acc ctg agg att cca     1492
Ser Tyr Asn Ser Leu Gly Lys Ser Pro Val Ala Thr Leu Arg Ile Pro
            320                 325                 330

gct att caa gaa aaa tca ttt cag tgc att gag gtc atg cag gcc tgc     1540
Ala Ile Gln Glu Lys Ser Phe Gln Cys Ile Glu Val Met Gln Ala Cys
        335                 340                 345

gtt gct gag gac cag cta gtg gtg aag tgg caa agc tct gct cta gac     1588
Val Ala Glu Asp Gln Leu Val Val Lys Trp Gln Ser Ser Ala Leu Asp
    350                 355                 360

gtg aac act tgg atg att gaa tgg ttt ccg gat gtg gac tca gag ccc     1636
Val Asn Thr Trp Met Ile Glu Trp Phe Pro Asp Val Asp Ser Glu Pro
365                 370                 375                 380

acc acc ctt tcc tgg gaa tct gtg tct cag gcc acg aac tgg acg atc     1684
Thr Thr Leu Ser Trp Glu Ser Val Ser Gln Ala Thr Asn Trp Thr Ile
                385                 390                 395

cag caa gat aaa tta aaa cct ttc tgg tgc tat aac atc tct gtg tat     1732
Gln Gln Asp Lys Leu Lys Pro Phe Trp Cys Tyr Asn Ile Ser Val Tyr
            400                 405                 410

cca atg ttg cat gac aaa gtt ggc gag cca tat tcc atc cag gct tat     1780
Pro Met Leu His Asp Lys Val Gly Glu Pro Tyr Ser Ile Gln Ala Tyr
        415                 420                 425

gcc aaa gaa ggc gtt cca tca gaa ggt cct gag acc aag gtg gag aac     1828
Ala Lys Glu Gly Val Pro Ser Glu Gly Pro Glu Thr Lys Val Glu Asn
    430                 435                 440

att ggc gtg aag acg gtc acg atc aca tgg aaa gag att ccc aag agt     1876
Ile Gly Val Lys Thr Val Thr Ile Thr Trp Lys Glu Ile Pro Lys Ser
445                 450                 455                 460

gag aga aag ggt atc atc tgc aac tac acc atc ttt tac caa gct gaa     1924
Glu Arg Lys Gly Ile Ile Cys Asn Tyr Thr Ile Phe Tyr Gln Ala Glu
                465                 470                 475

ggt gga aaa gga ttc tcc aag aca gtc aat tcc agc atc ttg cag tac     1972
Gly Gly Lys Gly Phe Ser Lys Thr Val Asn Ser Ser Ile Leu Gln Tyr
            480                 485                 490

ggc ctg gag tcc ctg aaa cga aag acc tct tac att gtt cag gtc atg     2020
Gly Leu Glu Ser Leu Lys Arg Lys Thr Ser Tyr Ile Val Gln Val Met
        495                 500                 505

gcc agc acc agt gct ggg gga acc aac ggg acc agc ata aat ttc aag     2068
Ala Ser Thr Ser Ala Gly Gly Thr Asn Gly Thr Ser Ile Asn Phe Lys
```

```
    510                 515                 520

aca ttg tca ttc agt gtc ttt gag att atc ctc ata act tct ctg att      2116
Thr Leu Ser Phe Ser Val Phe Glu Ile Ile Leu Ile Thr Ser Leu Ile
525                 530                 535                 540

ggt gga ggc ctt ctt att ctc att atc ctg aca gtg gca tat ggt ctc      2164
Gly Gly Gly Leu Leu Ile Leu Ile Ile Leu Thr Val Ala Tyr Gly Leu
                545                 550                 555

aaa aaa ccc aac aaa ttg act cat ctg tgt tgg ccc acc gtt ccc aac      2212
Lys Lys Pro Asn Lys Leu Thr His Leu Cys Trp Pro Thr Val Pro Asn
            560                 565                 570

cct gct gaa agt agt ata gcc aca tgg cat gga gat gat ttc aag gat      2260
Pro Ala Glu Ser Ser Ile Ala Thr Trp His Gly Asp Asp Phe Lys Asp
        575                 580                 585

aag cta aac ctg aag gag tct gat gac tct gtg aac aca gaa gac agg      2308
Lys Leu Asn Leu Lys Glu Ser Asp Asp Ser Val Asn Thr Glu Asp Arg
    590                 595                 600

atc tta aaa cca tgt tcc acc ccc agt gac aag ttg gtg att gac aag      2356
Ile Leu Lys Pro Cys Ser Thr Pro Ser Asp Lys Leu Val Ile Asp Lys
605                 610                 615                 620

ttg gtg gtg aac ttt ggg aat gtt ctg caa gaa att ttc aca gat gaa      2404
Leu Val Val Asn Phe Gly Asn Val Leu Gln Glu Ile Phe Thr Asp Glu
                625                 630                 635

gcc aga acg ggt cag gaa aac aat tta gga ggg gaa aag aat ggg act      2452
Ala Arg Thr Gly Gln Glu Asn Asn Leu Gly Gly Glu Lys Asn Gly Thr
            640                 645                 650

aga att ctg tct tcc tgc cca act tca ata taagtgtgga ctaaaatgcg      2502
Arg Ile Leu Ser Ser Cys Pro Thr Ser Ile
        655                 660

agaaaggtgt cctgtggtct atgcaaatta gaaaggacat gcagagtttt ccaactagga   2562

agactgaatc tgtggcccca agagaaccat ctctgaagac tgggtatgtg gtcttttcca   2622

cacatggacc acctacggat gcaatctgta atgcatgtgc atgagaagtc tgttattaag   2682

tagagtgtga aaacatggtt atggtaatag gaacagcttt taaaatgctt ttgtatttgg   2742

gcctttcata caaaaaagcc ataataccat tttcatgtaa tgctatactt ctatactatt   2802

ttcatgtaat actatacttc tatactattt tcatgtaata ctatacttct atactatttt   2862

catgtaatac tatacttcta tattaaagtt ttacccactc a                       2903


<210> SEQ ID NO 54
<211> LENGTH: 662
<212> TYPE: PRT
<213> ORGANISM: Homo sapiens

<400> SEQUENCE: 54

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110
```

```
Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
    370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
```

```
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
    610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660


<210> SEQ ID NO 55
<211> LENGTH: 1986
<212> TYPE: DNA
<213> ORGANISM: Artificial Sequence
<220> FEATURE:
<223> OTHER INFORMATION: Degenerate polynucleotide sequence of SEQ ID
      NO:54
<220> FEATURE:
<221> NAME/KEY: misc_feature
<222> LOCATION: (1)...(1986)
<223> OTHER INFORMATION: n = A,T,C or G

<400> SEQUENCE: 55

atgaarytnw snccncarcc nwsntgygtn aayytnggna tgatgtggac ntgggcnytn     60

tggatgytnc cnwsnytntg yaarttywsn ytngcngcny tnccngcnaa rccngaraay    120

athwsntgyg tntaytayta ymgnaaraay ytnacntgya cntggwsncc nggnaargar    180

acnwsntaya cncartayac ngtnaarmgn acntaygcnt tyggngaraa rcaygayaay    240

tgyacnacna aywsnwsnac nwsngaraay mgngcnwsnt gywsnttytt yytnccnmgn    300

athacnathc cngayaayta yacnathgar gtngargcng araayggnga yggngtnath    360

aarwsncaya tgacntaytg gmgnytngar aayathgcna aracngarcc nccnaarath    420

ttymgngtna arccngtnyt nggnathaar mgnatgathc arathgartg gathaarccn    480

garytngcnc cngtnwsnws ngayytnaar tayacnytnm gnttymgnac ngtnaaywsn    540

acnwsntgga tggargtnaa yttygcnaar aaymgnaarg ayaaraayca racntayaay    600

ytnacnggny tncarccntt yacngartay gtnathgcny tnmgntgygc ngtnaargar    660

wsnaarttyt ggwsngaytg gwsncargar aaratgggna tgacngarga rgargcnccn    720

tgyggnytng arytntggmg ngtnytnaar ccngcngarg cngayggnmg nmgnccngtn    780

mgnytnytnt ggaaraargc nmgnggngcn ccngtnytng araaracnyt nggntayaay    840

athtggtayt ayccngarws naayacnaay ytnacngara cnatgaayac nacnaaycar    900

carytngary tncayytngg nggngarwsn ttytgggtnw snatgathws ntayaaywsn    960

ytnggnaarw snccngtngc nacnytnmgn athccngcna thcargaraa rwsnttycar   1020

tgyathgarg tnatgcargc ntgygtngcn gargaycary tngtngtnaa rtggcarwsn   1080

wsngcnytng aygtnaayac ntggatgath gartggttyc cngaygtnga ywsngarccn   1140

acnacnytnw sntgggarws ngtnwsncar gcnacnaayt ggacnathca rcargayaar   1200
```

```
ytnaarccnt tytggtgyta yaayathwsn gtntayccna tgytncayga yaargtnggn   1260

garccntayw snathcargc ntaygcnaar garggngtnc cnwsngargg nccngaracn   1320

aargtngara ayathggngt naaracngtn acnathacnt ggaargarat hccnaarwsn   1380

garmgnaarg gnathathtg yaaytayacn athttytayc argcngargg nggnaarggn   1440

ttywsnaara cngtnaayws nwsnathytn cartayggny tngarwsnyt naarmgnaar   1500

acnwsntaya thgtncargt natggcnwsn acnwsngcng gnggnacnaa yggnacnwsn   1560

athaayttya aracnytnws nttywsngtn ttygaratha thytnathac nwsnytnath   1620

ggnggnggny tnytnathyt nathathytn acngtngcnt ayggnytnaa raarccnaay   1680

aarytnacnc ayytntgytg gccnacngtn ccnaayccng cngarwsnws nathgcnacn   1740

tggcayggng aygayttyaa rgayaarytn aayytnaarg arwsngayga ywsngtnaay   1800

acngargaym gnathytnaa rccntgywsn acnccnwsng ayaarytngt nathgayaar   1860

ytngtngtna ayttyggnaa ygtnytncar garathttya cngaygargc nmgnacnggn   1920

cargaraaya ayytnggngg ngaraaraay ggnacnmgna thytnwsnws ntgyccnacn   1980

wsnath                                                              1986
```

```
<210> SEQ ID NO 56
<211> LENGTH: 2748
<212> TYPE: DNA
<213> ORGANISM: mus musculus
<220> FEATURE:
<221> NAME/KEY: CDS
<222> LOCATION: (237)...(2222)

<400> SEQUENCE: 56

gatggggccc tgaatgttga tctgacagaa ttccagacca acctggtggt tattgtcctt     60

ttcatctggt catgctgaat atactctcaa gatgtgctgg agaaggtgct gctgtccggg    120

ctctcagaga aggcagtgct ggaggcgttc ctggcccggg tctcctccta ctgttcctgg    180

tagcccagcc ttctcggggt ggaaggagaa gctggccagg tgagctctga ggaagc atg    239
                                                              Met
                                                               1

ctg agc agc cag aag gga tcc tgc agc cag gaa cca ggg gca gcc cac      287
Leu Ser Ser Gln Lys Gly Ser Cys Ser Gln Glu Pro Gly Ala Ala His
            5                  10                  15

gtc cag cct ctg ggt gtg aac gct gga ata atg tgg acc ttg gca ctg      335
Val Gln Pro Leu Gly Val Asn Ala Gly Ile Met Trp Thr Leu Ala Leu
        20                  25                  30

tgg gca ttc tct ttc ctc tgc aaa ttc agc ctg gca gtc ctg ccg act      383
Trp Ala Phe Ser Phe Leu Cys Lys Phe Ser Leu Ala Val Leu Pro Thr
    35                  40                  45

aag cca gag aac att tcc tgc gtc ttt tac ttc gac aga aat ctg act      431
Lys Pro Glu Asn Ile Ser Cys Val Phe Tyr Phe Asp Arg Asn Leu Thr
 50                  55                  60                  65

tgc act tgg aga cca gag aag gaa acc aat gat acc agc tac att gtg      479
Cys Thr Trp Arg Pro Glu Lys Glu Thr Asn Asp Thr Ser Tyr Ile Val
                70                  75                  80

act ttg act tac tcc tat gga aaa agc aat tat agt gac aat gct aca      527
Thr Leu Thr Tyr Ser Tyr Gly Lys Ser Asn Tyr Ser Asp Asn Ala Thr
            85                  90                  95

gag gct tca tat tct ttt ccc cgt tcc tgt gca atg ccc cca gac atc      575
Glu Ala Ser Tyr Ser Phe Pro Arg Ser Cys Ala Met Pro Pro Asp Ile
        100                 105                 110

tgc agt gtt gaa gta caa gct caa aat gga gat ggt aaa gtt aaa tct      623
Cys Ser Val Glu Val Gln Ala Gln Asn Gly Asp Gly Lys Val Lys Ser
```

```
    115                 120                 125

gac atc aca tat tgg cat tta atc tcc ata gca aaa acc gaa cca cct      671
Asp Ile Thr Tyr Trp His Leu Ile Ser Ile Ala Lys Thr Glu Pro Pro
130                 135                 140                 145

ata att tta agt gtg aat cca att tgt aat aga atg ttc cag ata caa      719
Ile Ile Leu Ser Val Asn Pro Ile Cys Asn Arg Met Phe Gln Ile Gln
                150                 155                 160

tgg aaa ccg cgt gaa aag act cgt ggg ttt cct tta gta tgc atg ctt      767
Trp Lys Pro Arg Glu Lys Thr Arg Gly Phe Pro Leu Val Cys Met Leu
            165                 170                 175

cgg ttc aga act gtc aac agt agc cgc tgg acg gaa gtc aat ttt gaa      815
Arg Phe Arg Thr Val Asn Ser Ser Arg Trp Thr Glu Val Asn Phe Glu
        180                 185                 190

aac tgt aaa cag gtc tgc aac ctc aca gga ctt cag gct ttc aca gaa      863
Asn Cys Lys Gln Val Cys Asn Leu Thr Gly Leu Gln Ala Phe Thr Glu
    195                 200                 205

tat gtc ctg gct cta cga ttc agg ttc aat gac tca aga tat tgg agc      911
Tyr Val Leu Ala Leu Arg Phe Arg Phe Asn Asp Ser Arg Tyr Trp Ser
210                 215                 220                 225

aag tgg agc aaa gaa gaa acc aga gtg act atg gag gaa gtt cca cat      959
Lys Trp Ser Lys Glu Glu Thr Arg Val Thr Met Glu Glu Val Pro His
                230                 235                 240

gtc ctg gac ctg tgg aga att ctg gaa cca gca gac atg aac gga gac     1007
Val Leu Asp Leu Trp Arg Ile Leu Glu Pro Ala Asp Met Asn Gly Asp
            245                 250                 255

agg aag gtg cga ttg ctg tgg aag aag gca aga gga gcc ccc gtc ttg     1055
Arg Lys Val Arg Leu Leu Trp Lys Lys Ala Arg Gly Ala Pro Val Leu
        260                 265                 270

gag aaa aca ttt ggc tac cac ata cag tac ttt gca gag aac agc act     1103
Glu Lys Thr Phe Gly Tyr His Ile Gln Tyr Phe Ala Glu Asn Ser Thr
    275                 280                 285

aac ctc aca gag ata aac aac atc acc acc cag cag tat gaa ctg ctt     1151
Asn Leu Thr Glu Ile Asn Asn Ile Thr Thr Gln Gln Tyr Glu Leu Leu
290                 295                 300                 305

ctg atg agc cag gca cac tct gtg tcc gtg act tct ttt aat tct ctt     1199
Leu Met Ser Gln Ala His Ser Val Ser Val Thr Ser Phe Asn Ser Leu
                310                 315                 320

ggc aag tcc caa gag acc atc ctg agg atc cca gat gtc cat gag aag     1247
Gly Lys Ser Gln Glu Thr Ile Leu Arg Ile Pro Asp Val His Glu Lys
            325                 330                 335

acc ttc cag tac att aag agc atg cag gcc tac ata gcc gag ccc ctg     1295
Thr Phe Gln Tyr Ile Lys Ser Met Gln Ala Tyr Ile Ala Glu Pro Leu
        340                 345                 350

ttg gtg gtg aac tgg caa agc tcc att cct gcg gtg gac act tgg ata     1343
Leu Val Val Asn Trp Gln Ser Ser Ile Pro Ala Val Asp Thr Trp Ile
    355                 360                 365

gtg gag tgg ctc cca gaa gct gcc atg tcg aag ttc cct gcc ctt tcc     1391
Val Glu Trp Leu Pro Glu Ala Ala Met Ser Lys Phe Pro Ala Leu Ser
370                 375                 380                 385

tgg gaa tct gtg tct cag gtc acg aac tgg acc atc gag caa gat aaa     1439
Trp Glu Ser Val Ser Gln Val Thr Asn Trp Thr Ile Glu Gln Asp Lys
                390                 395                 400

cta aaa cct ttc aca tgc tat aat ata tca gtg tat cca gtg ttg gga     1487
Leu Lys Pro Phe Thr Cys Tyr Asn Ile Ser Val Tyr Pro Val Leu Gly
            405                 410                 415

cac cga gtt gga gag ccg tat tca atc caa gct tat gcc aaa gaa gga     1535
His Arg Val Gly Glu Pro Tyr Ser Ile Gln Ala Tyr Ala Lys Glu Gly
        420                 425                 430

act cca tta aaa ggt cct gag acc agg gtg gag aac atc ggt ctg agg     1583
Thr Pro Leu Lys Gly Pro Glu Thr Arg Val Glu Asn Ile Gly Leu Arg
```

```
    435                 440                 445

aca gcc acg atc aca tgg aag gag att cct aag agt gct agg aat gga      1631
Thr Ala Thr Ile Thr Trp Lys Glu Ile Pro Lys Ser Ala Arg Asn Gly
450                 455                 460                 465

ttt atc aac aat tac act gta ttt tac caa gct gaa ggt gga aaa gaa      1679
Phe Ile Asn Asn Tyr Thr Val Phe Tyr Gln Ala Glu Gly Gly Lys Glu
                470                 475                 480

ctc tcc aag act gtt aac tct cat gcc ctg cag tgt gac ctg gag tct      1727
Leu Ser Lys Thr Val Asn Ser His Ala Leu Gln Cys Asp Leu Glu Ser
            485                 490                 495

ctg aca cga agg acc tct tat act gtt tgg gtc atg gcc agc acc aga      1775
Leu Thr Arg Arg Thr Ser Tyr Thr Val Trp Val Met Ala Ser Thr Arg
        500                 505                 510

gct gga ggt acc aac ggg gtg aga ata aac ttc aag aca ttg tca atc      1823
Ala Gly Gly Thr Asn Gly Val Arg Ile Asn Phe Lys Thr Leu Ser Ile
    515                 520                 525

agt gtg ttt gaa att gtc ctt cta aca tct cta gtt gga gga ggc ctt      1871
Ser Val Phe Glu Ile Val Leu Leu Thr Ser Leu Val Gly Gly Gly Leu
530                 535                 540                 545

ctt cta ctt agc atc aaa aca gtg act ttt ggc ctc aga aag cca aac      1919
Leu Leu Leu Ser Ile Lys Thr Val Thr Phe Gly Leu Arg Lys Pro Asn
                550                 555                 560

cgg ttg act ccc ctg tgt tgt cct gat gtt ccc aac cct gct gaa agt      1967
Arg Leu Thr Pro Leu Cys Cys Pro Asp Val Pro Asn Pro Ala Glu Ser
            565                 570                 575

agt tta gcc aca tgg ctc gga gat ggt ttc aag aag tca aat atg aag      2015
Ser Leu Ala Thr Trp Leu Gly Asp Gly Phe Lys Lys Ser Asn Met Lys
        580                 585                 590

gag act gga aac tct ggg aac aca gaa gac gtg gtc cta aaa cca tgt      2063
Glu Thr Gly Asn Ser Gly Asn Thr Glu Asp Val Val Leu Lys Pro Cys
    595                 600                 605

ccc gtc ccc gcg gat ctc att gac aag ctg gta gtg aac ttt gag aat      2111
Pro Val Pro Ala Asp Leu Ile Asp Lys Leu Val Val Asn Phe Glu Asn
610                 615                 620                 625

ttt ctg gaa gta gtt ttg aca gag gaa gct gga aag ggt cag gcg agc      2159
Phe Leu Glu Val Val Leu Thr Glu Glu Ala Gly Lys Gly Gln Ala Ser
                630                 635                 640

att ttg gga gga gaa gcg aat gag tat atc tta tcc cag gaa cca agc      2207
Ile Leu Gly Gly Glu Ala Asn Glu Tyr Ile Leu Ser Gln Glu Pro Ser
            645                 650                 655

tgt cct ggc cat tgc tgaagctacc ctcagggtcc aggacagctg tcttgttggc      2262
Cys Pro Gly His Cys
        660

acttgactct ggcaggaacc tgatctctac ttttcttctc cctgtctccg gacactttct   2322

ctccttcatg cagagaccag gactagagcg gattcctcat ggtttgccag gctcctcagt   2382

ccttgctcgg gctcaggatc ttcaacaatg ccctttctgg gacactccat catccactta   2442

tatttatttt ttgcaacatt gtggattgaa cccagggact tgtttatgcg cgcaacttca   2502

gtaactgtgg cagagactta ggaatggaga tctgaccctt tgcagaaggt ttctggacat   2562

ccgtccctgt gtgagcctca gacagcattg tctttacttt gaatcagctt ccaagttaat   2622

aaaagaaaaa cagagaggtg gcataacagc tcctgcttcc tgacctgctt gagttccagt   2682

tctgacttcc tttggtgatg aacagcaatg tgggaagtgt aagctgaata aacccttttcc  2742

tcccca                                                              2748

<210> SEQ ID NO 57
<211> LENGTH: 662
<212> TYPE: PRT
```

<213> ORGANISM: mus musculus

<400> SEQUENCE: 57

```
Met Leu Ser Ser Gln Lys Gly Ser Cys Ser Gln Glu Pro Gly Ala Ala
 1               5                  10                  15

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
    50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
```

```
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Val Phe Glu Ile Val Leu Leu Thr Ser Leu Val Gly Gly Gly
    530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
                565                 570                 575

Ser Ser Leu Ala Thr Trp Leu Gly Asp Gly Phe Lys Lys Ser Asn Met
            580                 585                 590

Lys Glu Thr Gly Asn Ser Gly Asn Thr Glu Asp Val Val Leu Lys Pro
        595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660


<210> SEQ ID NO 58
<211> LENGTH: 21
<212> TYPE: DNA
<213> ORGANISM: Artificial Sequence
<220> FEATURE:
<223> OTHER INFORMATION: Oligonucleotide primer ZC6673

<400> SEQUENCE: 58

gcgcaaggtg ccgttcacag c                                              21


<210> SEQ ID NO 59
<211> LENGTH: 36
<212> TYPE: DNA
<213> ORGANISM: Artificial Sequence
<220> FEATURE:
<223> OTHER INFORMATION: Oligonucleotide primer ZC29082

<400> SEQUENCE: 59

caatttgttg ggttttttta gcagcagtag gcccag                              36


<210> SEQ ID NO 60
<211> LENGTH: 36
<212> TYPE: DNA
<213> ORGANISM: Artificial Sequence
<220> FEATURE:
```

<223> OTHER INFORMATION: Oligonucleotide primer ZC29083

<400> SEQUENCE: 60
ctgggcctac tgctgctaaa aaaacccaac aaattg 36

<210> SEQ ID NO 61
<211> LENGTH: 36
<212> TYPE: DNA
<213> ORGANISM: Artificial Sequence
<220> FEATURE:
<223> OTHER INFORMATION: Oligonucleotide primer ZC29145

<400> SEQUENCE: 61
gcgtctagag ggttatattg aagttgggca ggaaga 36

<210> SEQ ID NO 62
<211> LENGTH: 33
<212> TYPE: DNA
<213> ORGANISM: Artificial Sequence
<220> FEATURE:
<223> OTHER INFORMATION: Oligonucleotide primer ZC29359

<400> SEQUENCE: 62
gcgggatcca tgaagctctc tccccagcct tca 33

<210> SEQ ID NO 63
<211> LENGTH: 23
<212> TYPE: DNA
<213> ORGANISM: Artificial Sequence
<220> FEATURE:
<223> OTHER INFORMATION: Oligonucleotide primer ZC27899

<400> SEQUENCE: 63
ccagaacttt gactccttga ccg 23

<210> SEQ ID NO 64
<211> LENGTH: 23
<212> TYPE: DNA
<213> ORGANISM: Artificial Sequence
<220> FEATURE:
<223> OTHER INFORMATION: Oligonucleotide primer ZC27895

<400> SEQUENCE: 64
gaagtcaact tcgctaagaa ccg 23

<210> SEQ ID NO 65
<211> LENGTH: 34
<212> TYPE: DNA
<213> ORGANISM: Artificial Sequence
<220> FEATURE:
<223> OTHER INFORMATION: Oligonucleotide primer ZC29122

<400> SEQUENCE: 65
ccgctcgagt tatattgaag ttgggcagga agac 34

<210> SEQ ID NO 66
<211> LENGTH: 33
<212> TYPE: DNA
<213> ORGANISM: Artificial Sequence
<220> FEATURE:
<223> OTHER INFORMATION: Oligonucleotide primer ZC29451

<400> SEQUENCE: 66
ccggaattcc cctgatacat gaagctctct ccc 33

<210> SEQ ID NO 67

```
<211> LENGTH: 33
<212> TYPE: DNA
<213> ORGANISM: Artificial Sequence
<220> FEATURE:
<223> OTHER INFORMATION: Oligonucleotide primer ZC29124

<400> SEQUENCE: 67

cgcggatccc tcaaagacac tgaatgacaa tgt                              33


<210> SEQ ID NO 68
<211> LENGTH: 2295
<212> TYPE: DNA
<213> ORGANISM: Artificial Sequence
<220> FEATURE:
<223> OTHER INFORMATION: Polynucleitide encoding human zcytor17-Fc4
      fusion
<220> FEATURE:
<221> NAME/KEY: CDS
<222> LOCATION: (1)...(2295)

<400> SEQUENCE: 68

atg aag ctc tct ccc cag cct tca tgt gtt aac ctg ggg atg atg tgg      48
Met Lys Leu Ser Pro Gln Pro Ser Cys Val Asn Leu Gly Met Met Trp
 1               5                  10                  15

acc tgg gca ctg tgg atg ctc cct tca ctc tgc aaa ttc agc ctg gca      96
Thr Trp Ala Leu Trp Met Leu Pro Ser Leu Cys Lys Phe Ser Leu Ala
            20                  25                  30

gct ctg cca gct aag cct gag aac att tcc tgt gtc tac tac tat agg     144
Ala Leu Pro Ala Lys Pro Glu Asn Ile Ser Cys Val Tyr Tyr Tyr Arg
        35                  40                  45

aaa aat tta acc tgc act tgg agt cca gga aag gaa acc agt tat acc     192
Lys Asn Leu Thr Cys Thr Trp Ser Pro Gly Lys Glu Thr Ser Tyr Thr
    50                  55                  60

cag tac aca gtt aag aga act tac gct ttt gga gaa aaa cat gat aat     240
Gln Tyr Thr Val Lys Arg Thr Tyr Ala Phe Gly Glu Lys His Asp Asn
 65                  70                  75                  80

tgt aca acc aat agt tct aca agt gaa aat cgt gct tcg tgc tct ttt     288
Cys Thr Thr Asn Ser Ser Thr Ser Glu Asn Arg Ala Ser Cys Ser Phe
                85                  90                  95

ttc ctt cca aga ata acg atc cca gat aat tat acc att gag gtg gaa     336
Phe Leu Pro Arg Ile Thr Ile Pro Asp Asn Tyr Thr Ile Glu Val Glu
            100                 105                 110

gct gaa aat gga gat ggt gta att aaa tct cat atg aca tac tgg aga     384
Ala Glu Asn Gly Asp Gly Val Ile Lys Ser His Met Thr Tyr Trp Arg
        115                 120                 125

tta gag aac ata gcg aaa act gaa cca cct aag att ttc cgt gtg aaa     432
Leu Glu Asn Ile Ala Lys Thr Glu Pro Pro Lys Ile Phe Arg Val Lys
    130                 135                 140

cca gtt ttg ggc atc aaa cga atg att caa att gaa tgg ata aag cct     480
Pro Val Leu Gly Ile Lys Arg Met Ile Gln Ile Glu Trp Ile Lys Pro
145                 150                 155                 160

gag ttg gcg cct gtt tca tct gat tta aaa tac aca ctt cga ttc agg     528
Glu Leu Ala Pro Val Ser Ser Asp Leu Lys Tyr Thr Leu Arg Phe Arg
                165                 170                 175

aca gtc aac agt acc agc tgg atg gaa gtc aac ttc gct aag aac cgt     576
Thr Val Asn Ser Thr Ser Trp Met Glu Val Asn Phe Ala Lys Asn Arg
            180                 185                 190

aag gat aaa aac caa acg tac aac ctc acg ggg ctg cag cct ttt aca     624
Lys Asp Lys Asn Gln Thr Tyr Asn Leu Thr Gly Leu Gln Pro Phe Thr
        195                 200                 205

gaa tat gtc ata gct ctg cga tgt gcg gtc aag gag tca aag ttc tgg     672
Glu Tyr Val Ile Ala Leu Arg Cys Ala Val Lys Glu Ser Lys Phe Trp
    210                 215                 220
```

```
agt gac tgg agc caa gaa aaa atg gga atg act gag gaa gaa gct cca      720
Ser Asp Trp Ser Gln Glu Lys Met Gly Met Thr Glu Glu Glu Ala Pro
225                 230                 235                 240

tgt ggc ctg gaa ctg tgg aga gtc ctg aaa cca gct gag gcg gat gga      768
Cys Gly Leu Glu Leu Trp Arg Val Leu Lys Pro Ala Glu Ala Asp Gly
                245                 250                 255

aga agg cca gtg cgg ttg tta tgg aag aag gca aga gga gcc cca gtc      816
Arg Arg Pro Val Arg Leu Leu Trp Lys Lys Ala Arg Gly Ala Pro Val
            260                 265                 270

cta gag aaa aca ctt ggc tac aac ata tgg tac tat cca gaa agc aac      864
Leu Glu Lys Thr Leu Gly Tyr Asn Ile Trp Tyr Tyr Pro Glu Ser Asn
        275                 280                 285

act aac ctc aca gaa aca atg aac act act aac cag cag ctt gaa ctg      912
Thr Asn Leu Thr Glu Thr Met Asn Thr Thr Asn Gln Gln Leu Glu Leu
    290                 295                 300

cat ctg gga ggc gag agc ttt tgg gtg tct atg att tct tat aat tct      960
His Leu Gly Gly Glu Ser Phe Trp Val Ser Met Ile Ser Tyr Asn Ser
305                 310                 315                 320

ctt ggg aag tct cca gtg gcc acc ctg agg att cca gct att caa gaa     1008
Leu Gly Lys Ser Pro Val Ala Thr Leu Arg Ile Pro Ala Ile Gln Glu
                325                 330                 335

aaa tca ttt cag tgc att gag gtc atg cag gcc tgc gtt gct gag gac     1056
Lys Ser Phe Gln Cys Ile Glu Val Met Gln Ala Cys Val Ala Glu Asp
            340                 345                 350

cag cta gtg gtg aag tgg caa agc tct gct cta gac gtg aac act tgg     1104
Gln Leu Val Val Lys Trp Gln Ser Ser Ala Leu Asp Val Asn Thr Trp
        355                 360                 365

atg att gaa tgg ttt ccg gat gtg gac tca gag ccc acc acc ctt tcc     1152
Met Ile Glu Trp Phe Pro Asp Val Asp Ser Glu Pro Thr Thr Leu Ser
    370                 375                 380

tgg gaa tct gtg tct cag gcc acg aac tgg acg atc cag caa gat aaa     1200
Trp Glu Ser Val Ser Gln Ala Thr Asn Trp Thr Ile Gln Gln Asp Lys
385                 390                 395                 400

tta aaa ccc ttc tgg tgc tat aac atc tct gtg tat cca atg ttg cat     1248
Leu Lys Pro Phe Trp Cys Tyr Asn Ile Ser Val Tyr Pro Met Leu His
                405                 410                 415

gac aaa gtt ggc gag cca tat tcc atc cag gct tat gcc aaa gaa ggc     1296
Asp Lys Val Gly Glu Pro Tyr Ser Ile Gln Ala Tyr Ala Lys Glu Gly
            420                 425                 430

gtt cca tca gaa ggt cct gag acc aag gtg gag aac att ggc gtg aag     1344
Val Pro Ser Glu Gly Pro Glu Thr Lys Val Glu Asn Ile Gly Val Lys
        435                 440                 445

acg gtc acg atc aca tgg aaa gag att ccc aag agt gag aga aag ggt     1392
Thr Val Thr Ile Thr Trp Lys Glu Ile Pro Lys Ser Glu Arg Lys Gly
    450                 455                 460

atc atc tgc aac tac acc atc ttt tac caa gct gaa ggt gga aaa gga     1440
Ile Ile Cys Asn Tyr Thr Ile Phe Tyr Gln Ala Glu Gly Gly Lys Gly
465                 470                 475                 480

ttc tcc aag aca gtc aat tcc agc atc ttg cag tac ggc ctg gag tcc     1488
Phe Ser Lys Thr Val Asn Ser Ser Ile Leu Gln Tyr Gly Leu Glu Ser
                485                 490                 495

ctg aaa cga aag acc tct tac att gtt cag gtc atg gcc agc acc agt     1536
Leu Lys Arg Lys Thr Ser Tyr Ile Val Gln Val Met Ala Ser Thr Ser
            500                 505                 510

gct ggg gga acc aac ggg acc agc ata aat ttc aag aca ttg tca ttc     1584
Ala Gly Gly Thr Asn Gly Thr Ser Ile Asn Phe Lys Thr Leu Ser Phe
        515                 520                 525

agt gtc ttt gag gag ccc aga tct tca gac aaa act cac aca tgc cca     1632
Ser Val Phe Glu Glu Pro Arg Ser Ser Asp Lys Thr His Thr Cys Pro
    530                 535                 540
```

```
ccg tgc cca gca cct gaa gcc gag ggg gca ccg tca gtc ttc ctc ttc      1680
Pro Cys Pro Ala Pro Glu Ala Glu Gly Ala Pro Ser Val Phe Leu Phe
545                 550                 555                 560

ccc cca aaa ccc aag gac acc ctc atg atc tcc cgg acc cct gag gtc      1728
Pro Pro Lys Pro Lys Asp Thr Leu Met Ile Ser Arg Thr Pro Glu Val
                565                 570                 575

aca tgc gtg gtg gtg gac gtg agc cac gaa gac cct gag gtc aag ttc      1776
Thr Cys Val Val Val Asp Val Ser His Glu Asp Pro Glu Val Lys Phe
            580                 585                 590

aac tgg tac gtg gac ggc gtg gag gtg cat aat gcc aag aca aag ccg      1824
Asn Trp Tyr Val Asp Gly Val Glu Val His Asn Ala Lys Thr Lys Pro
        595                 600                 605

cgg gag gag cag tac aac agc acg tac cgt gtg gtc agc gtc ctc acc      1872
Arg Glu Glu Gln Tyr Asn Ser Thr Tyr Arg Val Val Ser Val Leu Thr
    610                 615                 620

gtc ctg cac cag gac tgg ctg aat ggc aag gag tac aag tgc aag gtc      1920
Val Leu His Gln Asp Trp Leu Asn Gly Lys Glu Tyr Lys Cys Lys Val
625                 630                 635                 640

tcc aac aaa gcc ctc cca tcc tcc atc gag aaa acc atc tcc aaa gcc      1968
Ser Asn Lys Ala Leu Pro Ser Ser Ile Glu Lys Thr Ile Ser Lys Ala
                645                 650                 655

aaa ggg cag ccc cga gaa cca cag gtg tac acc ctg ccc cca tcc cgg      2016
Lys Gly Gln Pro Arg Glu Pro Gln Val Tyr Thr Leu Pro Pro Ser Arg
            660                 665                 670

gat gag ctg acc aag aac cag gtc agc ctg acc tgc ctg gtc aaa ggc      2064
Asp Glu Leu Thr Lys Asn Gln Val Ser Leu Thr Cys Leu Val Lys Gly
        675                 680                 685

ttc tat ccc agc gac atc gcc gtg gag tgg gag agc aat ggg cag ccg      2112
Phe Tyr Pro Ser Asp Ile Ala Val Glu Trp Glu Ser Asn Gly Gln Pro
    690                 695                 700

gag aac aac tac aag acc acg cct ccc gtg ctg gac tcc gac ggc tcc      2160
Glu Asn Asn Tyr Lys Thr Thr Pro Pro Val Leu Asp Ser Asp Gly Ser
705                 710                 715                 720

ttc ttc ctc tac agc aag ctc acc gtg gac aag agc agg tgg cag cag      2208
Phe Phe Leu Tyr Ser Lys Leu Thr Val Asp Lys Ser Arg Trp Gln Gln
                725                 730                 735

ggg aac gtc ttc tca tgc tcc gtg atg cat gag gct ctg cac aac cac      2256
Gly Asn Val Phe Ser Cys Ser Val Met His Glu Ala Leu His Asn His
            740                 745                 750

tac acg cag aag agc ctc tcc ctg tct ccg ggt aaa taa                  2295
Tyr Thr Gln Lys Ser Leu Ser Leu Ser Pro Gly Lys  *
        755                 760
```

<210> SEQ ID NO 69
<211> LENGTH: 764
<212> TYPE: PRT
<213> ORGANISM: Artificial Sequence
<220> FEATURE:
<223> OTHER INFORMATION: Human Zcytor17-Fc4 fusion polypeptide

<400> SEQUENCE: 69

```
Met Lys Leu Ser Pro Gln Pro Ser Cys Val Asn Leu Gly Met Met Trp
 1               5                  10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80
```

```
Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
    370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
```

```
            500                 505                 510

Ala Gly Gly Thr Asn Gly Thr Ser Ile Asn Phe Lys Thr Leu Ser Phe
        515                 520                 525

Ser Val Phe Glu Glu Pro Arg Ser Ser Asp Lys Thr His Thr Cys Pro
    530                 535                 540

Pro Cys Pro Ala Pro Glu Ala Glu Gly Ala Pro Ser Val Phe Leu Phe
545                 550                 555                 560

Pro Pro Lys Pro Lys Asp Thr Leu Met Ile Ser Arg Thr Pro Glu Val
                565                 570                 575

Thr Cys Val Val Val Asp Val Ser His Glu Asp Pro Glu Val Lys Phe
            580                 585                 590

Asn Trp Tyr Val Asp Gly Val Glu Val His Asn Ala Lys Thr Lys Pro
        595                 600                 605

Arg Glu Glu Gln Tyr Asn Ser Thr Tyr Arg Val Val Ser Val Leu Thr
    610                 615                 620

Val Leu His Gln Asp Trp Leu Asn Gly Lys Glu Tyr Lys Cys Lys Val
625                 630                 635                 640

Ser Asn Lys Ala Leu Pro Ser Ser Ile Glu Lys Thr Ile Ser Lys Ala
                645                 650                 655

Lys Gly Gln Pro Arg Glu Pro Gln Val Tyr Thr Leu Pro Pro Ser Arg
            660                 665                 670

Asp Glu Leu Thr Lys Asn Gln Val Ser Leu Thr Cys Leu Val Lys Gly
        675                 680                 685

Phe Tyr Pro Ser Asp Ile Ala Val Glu Trp Glu Ser Asn Gly Gln Pro
    690                 695                 700

Glu Asn Asn Tyr Lys Thr Thr Pro Pro Val Leu Asp Ser Asp Gly Ser
705                 710                 715                 720

Phe Phe Leu Tyr Ser Lys Leu Thr Val Asp Lys Ser Arg Trp Gln Gln
                725                 730                 735

Gly Asn Val Phe Ser Cys Ser Val Met His Glu Ala Leu His Asn His
            740                 745                 750

Tyr Thr Gln Lys Ser Leu Ser Leu Ser Pro Gly Lys
        755                 760
```

<210> SEQ ID NO 70
<211> LENGTH: 34
<212> TYPE: DNA
<213> ORGANISM: Artificial Sequence
<220> FEATURE:
<223> OTHER INFORMATION: Oligonucleotide primer ZC29157

<400> SEQUENCE: 70
ctagtatggc cggccatgaa gctctctccc cagc 34

<210> SEQ ID NO 71
<211> LENGTH: 41
<212> TYPE: DNA
<213> ORGANISM: Artificial Sequence
<220> FEATURE:
<223> OTHER INFORMATION: Oligonucleotide primer ZC29150

<400> SEQUENCE: 71
gtctgaagat ctgggctcct caaagacact gaatgacaat g 41

<210> SEQ ID NO 72
<211> LENGTH: 22
<212> TYPE: DNA
<213> ORGANISM: Artificial Sequence
<220> FEATURE:

<223> OTHER INFORMATION: Oligonucleotide primer ZC29180

<400> SEQUENCE: 72
cctggagtcc ctgaaacgaa ag 22

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer ZC28917

<400> SEQUENCE: 73
tgcaagatgc tggaattgac 20

<210> SEQ ID NO 74
<211> LENGTH: 19
<212> TYPE: DNA
<213> ORGANISM: Artificial Sequence
<220> FEATURE:
<223> OTHER INFORMATION: Oligonucleotide primer ZC29179

<400> SEQUENCE: 74
gcagggttgg gaacggtgg 19

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer ZC28916

<400> SEQUENCE: 75
agtcaattcc agcatcttgc 20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide primer ZC28918

<400> SEQUENCE: 76
tcacagagtc atcagactcc 20

<210> SEQ ID NO 77
<211> LENGTH: 21
<212> TYPE: DNA
<213> ORGANISM: Artificial Sequence
<220> FEATURE:
<223> OTHER INFORMATION: Oligonucleotide primer ZC38065

<400> SEQUENCE: 77
ctttcctggg aatctgtgtc t 21

<210> SEQ ID NO 78
<211> LENGTH: 18
<212> TYPE: DNA
<213> ORGANISM: Artificial Sequence
<220> FEATURE:
<223> OTHER INFORMATION: Oligonucleotide primer ZC38068

<400> SEQUENCE: 78
cctccagctc tggtgctg 18

<210> SEQ ID NO 79

<211> LENGTH: 20
<212> TYPE: DNA
<213> ORGANISM: Artificial Sequence
<220> FEATURE:
<223> OTHER INFORMATION: Oligonucleotide primer ZC10651

<400> SEQUENCE: 79
agcttttctg cagcagctct 20

<210> SEQ ID NO 80
<211> LENGTH: 23
<212> TYPE: DNA
<213> ORGANISM: Artificial Sequence
<220> FEATURE:
<223> OTHER INFORMATION: Oligonucleotide primer ZC10565

<400> SEQUENCE: 80
tttgcagaaa aggttgcaaa tgc 23

<210> SEQ ID NO 81
<211> LENGTH: 24
<212> TYPE: DNA
<213> ORGANISM: Artificial Sequence
<220> FEATURE:
<223> OTHER INFORMATION: Oligonucleotide primer ZC37877

<400> SEQUENCE: 81
caaaaaaccc aacaaattga ctca 24

<210> SEQ ID NO 82
<211> LENGTH: 25
<212> TYPE: DNA
<213> ORGANISM: Artificial Sequence
<220> FEATURE:
<223> OTHER INFORMATION: Oligonucleotide primer ZC37876

<400> SEQUENCE: 82
catgtggcta tactactttc agcag 25

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide primer ZC37776 zcytor17
TaqMan(r) probe

<400> SEQUENCE: 83
ctgtgttggc ccaccgttcc ca 22

<210> SEQ ID NO 84
<211> LENGTH: 20
<212> TYPE: DNA
<213> ORGANISM: Artificial Sequence
<220> FEATURE:
<223> OTHER INFORMATION: rRNA forward primer

<400> SEQUENCE: 84
cggctaccac atccaaggaa 20

<210> SEQ ID NO 85
<211> LENGTH: 18
<212> TYPE: DNA
<213> ORGANISM: Artificial Sequence
<220> FEATURE:
<223> OTHER INFORMATION: rRNA reverse primer

<400> SEQUENCE: 85
gctggaatta ccgcggct 18

<210> SEQ ID NO 86
<211> LENGTH: 22
<212> TYPE: DNA
<213> ORGANISM: Artificial Sequence
<220> FEATURE:
<223> OTHER INFORMATION: rRNA TaqMan(r) probe

<400> SEQUENCE: 86
tgctggcacc agacttgccc tc 22

<210> SEQ ID NO 87
<211> LENGTH: 21
<212> TYPE: DNA
<213> ORGANISM: Artificial Sequence
<220> FEATURE:
<223> OTHER INFORMATION: Oligonucleotide primer ZC22276

<400> SEQUENCE: 87
gcttgccctt cagcatgtag a 21

<210> SEQ ID NO 88
<211> LENGTH: 19
<212> TYPE: DNA
<213> ORGANISM: Artificial Sequence
<220> FEATURE:
<223> OTHER INFORMATION: Oligonucleotide primer ZC38239

<400> SEQUENCE: 88
gccgactaag ccagagaac 19

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide primer ZC38245

<400> SEQUENCE: 89
ctgttgacag ttctgaaccg 20

<210> SEQ ID NO 90
<211> LENGTH: 20
<212> TYPE: DNA
<213> ORGANISM: Artificial Sequence
<220> FEATURE:
<223> OTHER INFORMATION: Oligonucleotide primer ZC38238

<400> SEQUENCE: 90
cgcggtttcc attgtatctg 20

<210> SEQ ID NO 91
<211> LENGTH: 8
<212> TYPE: PRT
<213> ORGANISM: Artificial Sequence
<220> FEATURE:
<223> OTHER INFORMATION: Modified Glu-Glu tag peptide

<400> SEQUENCE: 91

Gly Ser Glu Tyr Met Pro Met Glu
1 5

<210> SEQ ID NO 92
<211> LENGTH: 2728
<212> TYPE: DNA

```
<213> ORGANISM: Mus musculus
<220> FEATURE:
<221> NAME/KEY: CDS
<222> LOCATION: (237)...(1877)

<400> SEQUENCE: 92

gatggggccc tgaatgttga tctgacagaa ttccagacca acctggtggt tattgtcctt      60

ttcatctggt catgctgaat atactctcaa gatgtgctgg agaaggtgct gctgtccggg     120

ctctcagaga aggcagtgct ggaggcgttc ctggcccggg tctcctccta ctgttcctgg     180

tagcccagcc ttctcggggt ggaaggagaa gctggccagg tgagctctga ggaagc atg     239
                                                              Met
                                                               1

ctg agc agc cag aag gga tcc tgc agc cag gaa cca ggg gca gcc cac       287
Leu Ser Ser Gln Lys Gly Ser Cys Ser Gln Glu Pro Gly Ala Ala His
            5                   10                  15

gtc cag cct ctg ggt gtg aac gct gga ata atg tgg acc ttg gca ctg       335
Val Gln Pro Leu Gly Val Asn Ala Gly Ile Met Trp Thr Leu Ala Leu
        20                  25                  30

tgg gca ttc tct ttc ctc tgc aaa ttc agc ctg gca gtc ctg ccg act       383
Trp Ala Phe Ser Phe Leu Cys Lys Phe Ser Leu Ala Val Leu Pro Thr
    35                  40                  45

aag cca gag aac att tcc tgc gtc ttt tac ttc gac aga aat ctg act       431
Lys Pro Glu Asn Ile Ser Cys Val Phe Tyr Phe Asp Arg Asn Leu Thr
 50                  55                  60                  65

tgc act tgg aga cca gag aag gaa acc aat gat acc agc tac att gtg       479
Cys Thr Trp Arg Pro Glu Lys Glu Thr Asn Asp Thr Ser Tyr Ile Val
                70                  75                  80

act ttg act tac tcc tat gga aaa agc aat tat agt gac aat gct aca       527
Thr Leu Thr Tyr Ser Tyr Gly Lys Ser Asn Tyr Ser Asp Asn Ala Thr
            85                  90                  95

gag gct tca tat tct ttt ccc cgt tcc tgt gca atg ccc cca gac atc       575
Glu Ala Ser Tyr Ser Phe Pro Arg Ser Cys Ala Met Pro Pro Asp Ile
        100                 105                 110

tgc agt gtt gaa gta caa gct caa aat gga gat ggt aaa gtt aaa tct       623
Cys Ser Val Glu Val Gln Ala Gln Asn Gly Asp Gly Lys Val Lys Ser
    115                 120                 125

gac atc aca tat tgg cat tta atc tcc ata gca aaa acc gaa cca cct       671
Asp Ile Thr Tyr Trp His Leu Ile Ser Ile Ala Lys Thr Glu Pro Pro
130                 135                 140                 145

ata att tta agt gtg aat cca att tgt aat aga atg ttc cag ata caa       719
Ile Ile Leu Ser Val Asn Pro Ile Cys Asn Arg Met Phe Gln Ile Gln
                150                 155                 160

tgg aaa ccg cgt gaa aag act cgt ggg ttt cct tta gta tgc atg ctt       767
Trp Lys Pro Arg Glu Lys Thr Arg Gly Phe Pro Leu Val Cys Met Leu
            165                 170                 175

cgg ttc aga act gtc aac agt agc cgc tgg acg gaa gtc aat ttt gaa       815
Arg Phe Arg Thr Val Asn Ser Ser Arg Trp Thr Glu Val Asn Phe Glu
        180                 185                 190

aac tgt aaa cag gtc tgc aac ctc aca gga ctt cag gct ttc aca gaa       863
Asn Cys Lys Gln Val Cys Asn Leu Thr Gly Leu Gln Ala Phe Thr Glu
    195                 200                 205

tat gtc ctg gct cta cga ttc agg ttc aat gac tca aga tat tgg agc       911
Tyr Val Leu Ala Leu Arg Phe Arg Phe Asn Asp Ser Arg Tyr Trp Ser
210                 215                 220                 225

aag tgg agc aaa gaa gaa acc aga gtg act atg gag gaa gtt cca cat       959
Lys Trp Ser Lys Glu Glu Thr Arg Val Thr Met Glu Glu Val Pro His
                230                 235                 240

gtc ctg gac ctg tgg aga att ctg gaa cca gca gac atg aac gga gac      1007
Val Leu Asp Leu Trp Arg Ile Leu Glu Pro Ala Asp Met Asn Gly Asp
            245                 250                 255
```

```
agg aag gtg cga ttg ctg tgg aag aag gca aga gga gcc ccc gtc ttg     1055
Arg Lys Val Arg Leu Leu Trp Lys Lys Ala Arg Gly Ala Pro Val Leu
        260                 265                 270

gag aaa aca ttt ggc tac cac ata cag tac ttt gca gag aac agc act     1103
Glu Lys Thr Phe Gly Tyr His Ile Gln Tyr Phe Ala Glu Asn Ser Thr
    275                 280                 285

aac ctc aca gag ata aac aac atc acc acc cag cag tat gaa ctg ctt     1151
Asn Leu Thr Glu Ile Asn Asn Ile Thr Thr Gln Gln Tyr Glu Leu Leu
290                 295                 300                 305

ctg atg agc cag gca cac tct gtg tcc gtg act tct ttt aat tct ctt     1199
Leu Met Ser Gln Ala His Ser Val Ser Val Thr Ser Phe Asn Ser Leu
                310                 315                 320

ggc aag tcc caa gag acc atc ctg agg atc cca gat gtc cat gag aag     1247
Gly Lys Ser Gln Glu Thr Ile Leu Arg Ile Pro Asp Val His Glu Lys
            325                 330                 335

acc ttc cag tac att aag agc atg cag gcc tac ata gcc gag ccc ctg     1295
Thr Phe Gln Tyr Ile Lys Ser Met Gln Ala Tyr Ile Ala Glu Pro Leu
        340                 345                 350

ttg gtg gtg aac tgg caa agc tcc att cct gcg gtg gac act tgg ata     1343
Leu Val Val Asn Trp Gln Ser Ser Ile Pro Ala Val Asp Thr Trp Ile
    355                 360                 365

gtg gag tgg ctc cca gaa gct gcc atg tcg aag ttc cct gcc ctt tcc     1391
Val Glu Trp Leu Pro Glu Ala Ala Met Ser Lys Phe Pro Ala Leu Ser
370                 375                 380                 385

tgg gaa tct gtg tct cag gtc acg aac tgg acc atc gag caa gat aaa     1439
Trp Glu Ser Val Ser Gln Val Thr Asn Trp Thr Ile Glu Gln Asp Lys
                390                 395                 400

cta aaa cct ttc aca tgc tat aat ata tca gtg tat cca gtg ttg gga     1487
Leu Lys Pro Phe Thr Cys Tyr Asn Ile Ser Val Tyr Pro Val Leu Gly
            405                 410                 415

cac cga gtt gga gag ccg tat tca atc caa gct tat gcc aaa gaa gga     1535
His Arg Val Gly Glu Pro Tyr Ser Ile Gln Ala Tyr Ala Lys Glu Gly
        420                 425                 430

act cca tta aaa ggt cct gag acc agg gtg gag aac atc ggt ctg agg     1583
Thr Pro Leu Lys Gly Pro Glu Thr Arg Val Glu Asn Ile Gly Leu Arg
    435                 440                 445

aca gcc acg atc aca tgg aag gag att cct aag agt gct agg aat gga     1631
Thr Ala Thr Ile Thr Trp Lys Glu Ile Pro Lys Ser Ala Arg Asn Gly
450                 455                 460                 465

ttt atc aac aat tac act gta ttt tac caa gct gaa ggt gga aaa gaa     1679
Phe Ile Asn Asn Tyr Thr Val Phe Tyr Gln Ala Glu Gly Gly Lys Glu
                470                 475                 480

ctc tcc aag act gtt aac tct cat gcc ctg cag tgt gac ctg gag tct     1727
Leu Ser Lys Thr Val Asn Ser His Ala Leu Gln Cys Asp Leu Glu Ser
            485                 490                 495

ctg aca cga agg acc tct tat act gtt tgg gtc atg gcc agc acc aga     1775
Leu Thr Arg Arg Thr Ser Tyr Thr Val Trp Val Met Ala Ser Thr Arg
        500                 505                 510

gct gga ggt acc aac ggg gtg aga ata aac ttc aag aca ttg tca atc     1823
Ala Gly Gly Thr Asn Gly Val Arg Ile Asn Phe Lys Thr Leu Ser Ile
    515                 520                 525

agt gag tac tgg ctt cag gcc tca ttc tgg agt tta ctt cgg gtt gga     1871
Ser Glu Tyr Trp Leu Gln Ala Ser Phe Trp Ser Leu Leu Arg Val Gly
530                 535                 540                 545

aat gtt tgacaggagc aaggagagcc agcagagggc agcagagcat ggcttctcct      1927
Asn Val

gctctctctg gctcactcac ctcccaggag ttactgagga gctggcaaag ggagggctga   1987

gttagaccaa caggccattt tgatccttgc tggtaagcag ccacaaataa tcttaagatg   2047
```

```
aagcaagcaa catccacttc agcctcagcc acgtcaaagg ctgttgcctg agctcacact   2107

ggccagttcc taaatgtcag gagttgtgca atagaacctg ggaaggaaca actggttgat   2167

cagaggtcac tgacaaggga cttaatgtta ccatctgcgg tggggctttt gtttcgtttt   2227

gtttgtttgt tatgtgtatt caacttatca gcttttacgt tgaaaacatg aaaagcaaga   2287

caaatttgtt agatatcaca tataatgtga aatataatag tttaataatt gagtaggaaa   2347

gctgagggca tgtaatagac agagggaaaa gaagaggaaa gccagtctgg tctacaaagt   2407

gagttccagg acagccaggg ctacatggag aaaccctgtc tcaatcaatc aatcaatcaa   2467

tcaatcagtc aatcaatcaa aattcaagca gcattgacaa gttttgcaat aactactata   2527

aaccaaaaaa gtcatcttga tgtatctcag aagccccttg ttatttatgt tcctgaagac   2587

taaagtagac cgtggctctg agaaccatga gcaagataac acgttctgtc ctgcagccta   2647

acaatgcctt cttggtattc tttttgatac aacttctaaa ataacttttt tttaaaaaaa   2707

ataaaaatca tgttacagct a                                              2728
```

<210> SEQ ID NO 93
<211> LENGTH: 547
<212> TYPE: PRT
<213> ORGANISM: Mus musculus

<400> SEQUENCE: 93

```
Met Leu Ser Ser Gln Lys Gly Ser Cys Ser Gln Glu Pro Gly Ala Ala
 1               5                  10                  15

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
    50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255
```

-continued

```
Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Glu Tyr Trp Leu Gln Ala Ser Phe Trp Ser Leu Leu Arg Val
    530                 535                 540

Gly Asn Val
545
```